(12) United States Patent
Quake et al.

(10) Patent No.: US 7,378,280 B2
(45) Date of Patent: May 27, 2008

(54) APPARATUS AND METHODS FOR CONDUCTING ASSAYS AND HIGH THROUGHPUT SCREENING

(75) Inventors: Stephen R. Quake, San Marino, CA (US); Marc A. Unger, South San Francisco, CA (US); Hou-Pu Chou, Sunnyvale, CA (US); Todd A. Thorsen, Pasadena, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 667 days.

(21) Appl. No.: 10/416,418

(22) PCT Filed: Nov. 16, 2001

(86) PCT No.: PCT/US01/44869

§ 371 (c)(1),
(2), (4) Date: Oct. 23, 2003

(87) PCT Pub. No.: WO02/40874

PCT Pub. Date: May 23, 2002

(65) Prior Publication Data

US 2004/0115838 A1    Jun. 17, 2004

Related U.S. Application Data

(60) Provisional application No. 60/281,948, filed on Apr. 6, 2001, provisional application No. 60/281,946, filed on Apr. 6, 2001, provisional application No. 60/249,327, filed on Nov. 16, 2000.

(51) Int. Cl.
*G01N 33/00* (2006.01)
*G01N 15/06* (2006.01)
*G01N 1/10* (2006.01)
*G01N 33/48* (2006.01)
*G01N 35/00* (2006.01)

(52) U.S. Cl. .......... 436/63; 422/50; 422/68.1; 422/81; 422/82; 422/100; 422/101; 422/103; 436/43; 436/174; 436/177; 436/180; 435/4; 435/325

(58) Field of Classification Search .......... 422/50, 422/68.1, 81, 82, 100, 101, 103; 436/43, 436/63, 174, 177, 180; 435/4, 325
See application file for complete search history.

(56) References Cited

U.S. PATENT DOCUMENTS 3,570,515 A    3/1971    Kinner
(Continued)

FOREIGN PATENT DOCUMENTS

DE    299 17 313 U1    2/2001
(Continued)

OTHER PUBLICATIONS

Axelrod, Daniel "Cell-Substrate Contacts Illuminated by Total Internal Reflection Fluorescence" Journal of Cell Biology, Apr. 1981, pp. 141-145, vol. 89.
(Continued)

*Primary Examiner*—Brian Sines
(74) *Attorney, Agent, or Firm*—Townsend and Townsend and Crew LLP

(57) ABSTRACT

The present invention provides microfluidic devices and methods for using the same. In particular, microfluidic devices of the present invention are useful in conducting a variety of assays and high throughput screening. Microfluidic devices of the present invention include elastomeric components and comprise a main flow channel; a plurality of branch flow channels; a plurality of control channels; and a plurality of valves. Preferably, each of the valves comprises one of the control channels and an elastomeric segment that is deflectable into or retractable from the main or branch flow channel upon which the valve operates in response to an actuation force applied to the control channel.

64 Claims, 18 Drawing Sheets

U.S. PATENT DOCUMENTS

| | | |
|---|---|---|
| 3,747,628 A | 7/1973 | Holster et al. |
| 4,046,159 A | 9/1977 | Pegourie |
| 4,119,368 A | 10/1978 | Yamakazi |
| 4,153,855 A | 5/1979 | Feingold |
| 4,245,673 A | 1/1981 | Bouteille et al. |
| 4,344,064 A | 8/1982 | Bitler et al. |
| 4,434,704 A | 3/1984 | Surjaatmadja |
| 4,707,237 A | 11/1987 | Lepp et al. |
| 4,898,582 A | 2/1990 | Faste |
| 4,992,312 A | 2/1991 | Frisch |
| 5,085,562 A | 2/1992 | Van Lintel |
| 5,088,515 A | 2/1992 | Kamen |
| 5,091,652 A | 2/1992 | Mathies et al. |
| 5,096,388 A | 3/1992 | Weinberg |
| 5,126,115 A | 6/1992 | Fujita et al. |
| 5,164,558 A | 11/1992 | Huff et al. |
| 5,171,132 A | 12/1992 | Miyazaki |
| 5,224,843 A | 7/1993 | Van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,304,487 A | 4/1994 | Wilding et al. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,423,287 A | 6/1995 | Usami et al. |
| 5,529,465 A | 6/1996 | Zengerle et al. |
| 5,593,130 A | 1/1997 | Hansson et al. |
| 5,639,423 A | 6/1997 | Northrup et al. |
| 5,642,015 A | 6/1997 | Whitehead et al. |
| 5,646,039 A | 7/1997 | Northrup et al. |
| 5,659,171 A | 8/1997 | Young et al. |
| 5,660,370 A | 8/1997 | Webster |
| 5,674,742 A | 10/1997 | Northrup et al. |
| 5,681,024 A | 10/1997 | Lisec et al. |
| 5,705,018 A | 1/1998 | Hartley |
| 5,759,014 A | 6/1998 | Van Lintel |
| 5,775,371 A | 7/1998 | Pan et al. |
| 5,788,468 A | 8/1998 | Dewa et al. |
| 5,802,856 A | 9/1998 | Schaper et al. |
| 5,832,165 A | 11/1998 | Reichert et al. |
| 5,836,750 A | 11/1998 | Cabuz |
| 5,842,787 A | 12/1998 | Kopf-Sill et al. |
| 5,846,396 A | 12/1998 | Zanzucchi et al. |
| 5,858,195 A | 1/1999 | Ramsey |
| 5,863,722 A | 1/1999 | Brenner |
| 5,875,817 A | 3/1999 | Carter |
| 5,876,187 A | 3/1999 | Forster et al. |
| 5,876,675 A | 3/1999 | Kennedy |
| 5,876,946 A | 3/1999 | Burbaum et al. |
| 5,888,778 A | 3/1999 | Shuber |
| 5,922,591 A | 7/1999 | Anderson et al. |
| 5,922,604 A | 7/1999 | Stapelton et al. |
| 5,928,880 A | 7/1999 | Wilding et al. |
| 5,932,799 A | 8/1999 | Moles |
| 5,942,443 A | 8/1999 | Parce et al. |
| 5,958,344 A | 9/1999 | Levine et al. |
| 5,972,639 A | 10/1999 | Parandoosh |
| 5,976,822 A | 11/1999 | Landrum et al. |
| 6,004,515 A | 12/1999 | Parce et al. |
| 6,007,309 A | 12/1999 | Hartley |
| 6,007,690 A | 12/1999 | Nelson et al. |
| 6,015,531 A | 1/2000 | Colin et al. |
| 6,018,616 A | 1/2000 | Schaper et al. |
| 6,043,080 A | 3/2000 | Lipshutz et al. |
| 6,046,056 A | 4/2000 | Parce et al. |
| 6,048,498 A | 4/2000 | Kennedy |
| 6,062,261 A | 5/2000 | Jacobson et al. |
| 6,094,274 A | 7/2000 | Yokoi |
| 6,103,537 A | 8/2000 | Ullman et al. |
| 6,107,044 A | 8/2000 | Nikiforov |
| 6,123,769 A | 9/2000 | Sanjoh |
| 6,132,580 A | 10/2000 | Mathies et al. |
| 6,132,685 A | 10/2000 | Kercso et al. |
| 6,136,212 A | 10/2000 | Mastrangelo et al. |
| 6,146,842 A | 11/2000 | Josiah et al. |
| 6,150,119 A | 11/2000 | Kopf-Sill et al. |
| 6,150,180 A | 11/2000 | Parce et al. |
| 6,155,282 A | 12/2000 | Zachary et al. |
| 6,165,694 A | 12/2000 | Liu |
| 6,167,910 B1 | 1/2001 | Chow |
| 6,171,850 B1 | 1/2001 | Nagle et al. |
| 6,174,365 B1 | 1/2001 | Sanjoh |
| 6,174,675 B1 | 1/2001 | Chow et al. |
| 6,197,595 B1 | 3/2001 | Anderson et al. |
| 6,214,246 B1 | 4/2001 | Craighead |
| 6,221,654 B1 | 4/2001 | Quake et al. |
| 6,225,109 B1 | 5/2001 | Juncosa et al. |
| 6,227,809 B1 | 5/2001 | Forster et al. |
| 6,235,471 B1 | 5/2001 | Knapp et al. |
| 6,296,673 B1 | 10/2001 | Santarsiero et al. |
| 6,306,659 B1 | 10/2001 | Parce et al. |
| 6,321,791 B1 | 11/2001 | Chow |
| 6,344,325 B1 | 2/2002 | Quake et al. |
| 6,345,502 B1 | 2/2002 | Tai et al. |
| 6,355,420 B1 | 3/2002 | Chan |
| 6,361,671 B1 | 3/2002 | Mathies et al. |
| 6,408,878 B2 | 6/2002 | Unger et al. |
| 6,409,832 B2 | 6/2002 | Weigl et al. |
| 6,540,895 B1 | 4/2003 | Spence et al. |
| 6,767,706 B2 | 7/2004 | Quake et al. |
| 2001/0041357 A1 | 11/2001 | Fouillet et al. |
| 2002/0124896 A1 | 9/2002 | O'Connor et al. |
| 2003/0008308 A1 | 1/2003 | Enzelberger et al. |
| 2003/0138829 A1 | 7/2003 | Unger et al. |
| 2003/0196695 A1 | 10/2003 | O'Connor et al. |

FOREIGN PATENT DOCUMENTS

| | | |
|---|---|---|
| EP | 0 579 997 A1 | 1/1994 |
| EP | 0 592 094 A2 | 4/1994 |
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 90/15070 A1 | 12/1990 |
| WO | WO 92/16657 A1 | 10/1992 |
| WO | WO 96/27025 A1 | 9/1996 |
| WO | WO 97/27324 A1 | 7/1997 |
| WO | WO 98/00231 A1 | 1/1998 |
| WO | WO 98/04742 A1 | 2/1998 |
| WO | WO 98/07069 A1 | 2/1998 |
| WO | WO 98/45481 A1 | 10/1998 |
| WO | WO 99/00655 A2 | 1/1999 |
| WO | WO 99/04361 A1 | 1/1999 |
| WO | WO 99/14311 A1 | 3/1999 |
| WO | WO 99/17093 A1 | 4/1999 |
| WO | WO 99/41015 A | 8/1999 |
| WO | WO 99/52633 A1 | 10/1999 |
| WO | WO 99/61888 A2 | 12/1999 |
| WO | WO 00/00678 A1 | 1/2000 |
| WO | WO 00/43748 A1 | 7/2000 |
| WO | WO 00/53801 A1 | 9/2000 |
| WO | WO 00/60345 A1 | 10/2000 |
| WO | WO 00/68414 A2 | 11/2000 |
| WO | WO 00/70082 A1 | 11/2000 |
| WO | WO 01/01025 A2 | 1/2001 |
| WO | WO 01/07061 A1 | 2/2001 |

| WO | WO 01/09595 A2 | 2/2001 |
|----|----------------|--------|
| WO | WO 01/09595 A3 | 2/2001 |
| WO | WO 01/24937 A2 | 4/2001 |
| WO | WO 01/32930 A1 | 5/2001 |
| WO | WO 02/00343 A2 | 1/2002 |
| WO | WO 02/29106 A2 | 4/2002 |
| WO | WO 02/30486 A2 | 4/2002 |
| WO | WO 02/40874 A1 | 5/2002 |
| WO | WO 02/43615 A2 | 6/2002 |
| WO | WO 02/065005 A1 | 8/2002 |
| WO | WO 02/072892 A1 | 9/2002 |
| WO | WO 02/081729 A2 | 10/2002 |
| WO | WO 02/081935 A2 | 10/2002 |
| WO | WO 03/048295 A1 | 6/2003 |

OTHER PUBLICATIONS

Benard et al., "A Titanium-Nickel Shape-Memory Alloy Actuated Micropump," Proceedings of Transducers '97, 1997 International Conference on Solid-State Sensors and Actuators, held in Chicago, IL., Jun. 16-19, 1997, 1:361-364 (1997).

Bryzek et al.; "Micromachines on the March", IEEE Spectrum, 1994, pp. 20-31, vol. 31, No. 5.

Buchaillot et al.; "Silicon nitride thin films Young's modulus determination by an optical non-destructive method", Jpn. J Appl Phys, 1995, pp. L794-L797, vol. 36, No. 2:6B.

Burns et al., "An Integrated Nanoliter DNA Analysis Device," Science, 282:484-487 (1998).

Chiu et al.; "Patterned Deposition of Cells and Proteins onto Surfaces by Using Three-Dimensional Microfluidic Systems", Proc. Natl. Acad. Sci., 2000, pp. 2408-2413, vol. 97, No. 6.

Chou, H. et al. "A microfabricated device for sizing and sorting DNA molecules", Applied Physical Sciences, Biophysics, Proc. Natl. Acad. Sci., 1999, pp. 11-13, vol. 96, U.S.A.

Chou, H. et al:, "A Microfabricated Rotary Pump," Biomedical Microdevices, 3(4):323-330 (2001).

Chou, H. et al., "Disposable Microdevices for DNA Analysis and Cell Sorting", Proc. Solid-State Sensor and Actuator Workshop, Hilton Head, SC, Jun. 8-11, 1998, pp. 11-14.

Chou, H. et al., "Integrated Elastomer Fluidic Lab-on-a-chip-Surface Patterning and DNA Diagnostics," Proceedings of the Solid State Actuator and Sensor Workshop, held in Hilton Head South Carolina in 2000.

Chou, H. et al., "Microfabricated devices for sizing DNA and sorting cells," In Micro- and Nanofabricated Structures and Devices for Biomedical Environmental Applications, Paul L. Gourley, Editor, Proceedings of SPIE, 1998, pp. 181-187, vol. 3258.

Delamarche et al.; "Patterned delivery of immunoglobulins to surfaces using microfluidic networks", Science, 1997, pp. 779-781, vol. 276.

Duffy et al. "Patterning Electroluminescence Materials with Feature Sizes as Small as 5 μm Using Elastomeric Membranes as Masks for Dry Lift-Off", Advanced Materials, 1999, pp. 546-552, vol. 11, No. 7.

Duffy et al. "Rapid Prototyping of Microfluidic Switches in Poly(dimethylsiloxane) and Their Actuation by Electro-Osmotic Flow" Journal of Microeng, 1999, pp. 211-217, vol. 9.

Duffy et al. "Rapid Prototyping of Microfluidic Systems in Poly(dimethylsiloxane)", Analytical Chemistry, 1998, pp. 4974-4984, vol. 70, No. 23.

Effenhauser et al.; "Integrated capillary electrophoresis on flexible silicone microdevices: Analysis of DNA restriction fragments and detection of single DNA molecules on microchips", Anal. Chem, 1997, pp. 3451-3457, vol. 69.

Effenhauser et al.; "Integrated chip-based capillary electrophoresis", Electrophoresis, 1997, pp. 2203-2213, vol. 18

Erlich, H.A.; *PCR Technology*, Basic Methodology: pp. 1-5, 1989, Stockton Press, New York.

Fahrenberg et al. "A microvalve system fabricated by thermoplastic molding", J Micromech Microeng, 1995, pp. 169-171, vol. 5.

Fu et al. "A microfabricated fluorescence-activated cell-sorter", Nature Biotechnology, 1999, pp. 1109-1111, vol. 17.

Gass et al., "Integrated flow-regulated silicon micropump," Sensors and Actuators A Physical, 1994, p. 335-338, vol. 43.

Gerlach, T., "Pumping Gases by a Silicon Micro Pump with Dynamic Passive Valves," Proceedings of Transducers '97, 1997 International Conference on Solid-State Sensors and Actuators, held in Chicago, II., Jun. 16-19, 1997, 1:357-360 (1997).

Goll et al., "Microvalves with bistable buckled polymer diaphragms," J. Micromech. Microeng., 1996, pp. 77-79, vol. 6.

Gonzalez, J.E. & Tsien, R. "Improved indicators of cell membrane potential that use fluorescence resonance energy transfer", *Chem. Biol.*, 1997, pp. 269-277, vol. 4, No. 4.

Gravesen et al.; "Microfluids- A Review", Journal of Micromech Microeng; 1993, pp. 168-192, vol. 3.

Harrison et al., "Micromachining a Miniaturized Capillary Electrophoresis-Based Chemical Analysis System on a Chip," Science, 1993, pp. 895-897, vol. 261.

Hermanson, G.T. et al. *Immobilized Affinity Ligand Technologies*, 1992, Chapter 2, Academic Press, San Diego, U.S.A.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, 1988, Optical Society of America, pp. 107-110.

Hosokawa et al.; "Handling of Picoliter Liquid Samples in a Poly(dimethylsiloxane)-Based Microfluidic Device," Anal. Chem., 1999, 71(20):4781-4785.

Ikuta et al., "Three dimensional micro integrated fluid systems (MIFS) fabricated by stereo lithography," IEEE Kyushu Institute of Technology, 1994, pp. 1-6.

Jacobson et al., "High-speed separations on a microchip," Anal. Chem., 1994, 66(7):1114-1118.

Jacobson et al., "Microfluidic Devices for Electrokinetically Driven Parallel and Serial Mixing," Anal. Chem., 1999, 71(20):4455-4459.

Jerman, H., "Electrically-Activated, Normally-Closed Diaphragm Valves," Proceedings of Transducers '91, 1991 International Conference on Solid-State Sensors and Actuators, pp. 1045-1048 (1991).

Khandurina et al., "Integrated System for Rapid PCR-Based DNA Analysis in Microfluidic Devices," Anal. Chem., 72:2995-3000 (2000).

Kim, E. et al., "Micromolding in Capillaries: Applications in Material Science," J. American Chemical Society, 118:5722-5731 (1996).

Lagally et al., "Single-Molecule DNA Amplification and Analysis in an Integrated Microfluidic Device," Anal. Chem., 73:565-570 (2001).

Levine, L.M. et al. "Measurement of specific protease activity utilizing fluorescence polarization", *Anal. Biochem.*, 1997, pp. 83-88, vol. 247, No. 1.

Llopis, J. et al. "Ligand-dependent interactions of coactivators steroid receptor coactivator-1 and peroxisome proliferator-activated receptor binding protein with nuclear hormone receptors can be imaged in live cells and are required for transcription", *Proc. Natl. Acad. Sci. U.S.A.*, 2000, pp. 4363-4368, vol. 97, No. 8.

Lötters et al. "The mechanical properties of the rubber elastic polymer polydimethylsiloxane for sensor applications," J. Micromech. Microeng., 1997, 7:145-147.

Mahajan, N.P. et al. "Novel mutant green fluorescent protein protease substrates reveal the activation of specific caspases during apoptosis", *Chem. Biol.*, 1999, pp. 401-409, vol. 6, No. 6.

Moreno Davila, H. "Molecular and functional diversity of voltage-gated calcuim channels", *Molecular and Functional Diversity of Ion Channels and Receptors, Ann N. Y. Acad. Sci.*, 1999, pp. 102-117, vol. 868.

Muller et al., "Surface-Micromachined Microoptical Elements and Systems," Proceedings of IEEE, 1998, 86(8): 1705-1720.

Nagai, Y. et al. "A fluorescent indicator for visualizing cAMP-induced phosphorylation in vivo." *Nat Biotechnol.*, 2000, pp. 313-316, vol. 18, No. 3.

Olsson et al., "Simulation Studies of Diffuser and Nozzle Elements for Valve-less Micropumps," Proceedings of Transducers '97, 1997 International Conference on Solid-State Sensors and Actuators, held in Chicago, Il., Jun. 16-19, 1997, 2:1039-1042 (1997).

Parker, G.J. et al. "Development of high throughput screening assays using fluorescence polarization: nuclear receptor-ligand-binding and kinase/phophatase assays", *J. Biomol. Screen.*, 2000, pp. 77-88, vol. 5, No. 2.

Qin et al., "Elastomeric Light Valves", Adv. Mater., 1997, pp. 407-410, vol. 9, No. 5.

Quake S.R. and Scherer A.; "From micro- to nanofabrication with soft materials", Science, Nov. 24, 2000; pp. 1536-1540, vol. 290, No. 5496.

Rapp. R., "LIGA micropump for gases and liquids," Sensors and Actuators A, 1994, pp. 57-61, vol. 40.

Schasfoort et al., "Field-Effect Flow Control for Microfabricated Fluidic Networks," Science, 1999, 286:942-945.

Schueller et al., "Fabrication of glassy carbon microstructures by soft lithography," Sensors and Actuators; 72(2):125-139 (1999).

Seethala, R. & Menzel, R. "A fluorescence polarization competition immunoassay for tyrosine kinases", *Anal. Biochem.*, 1998, pp. 257-262, vol. 255, No. 2.

Shoji et al.; "Smallest Dead Volume Microvalves for Integrated Chemical Analyzing Systems", Proceedings of Transducers '91, 1991, pp. 1052-1055, San Francisco.

Shoji, S.; "Fluids for Sensor Systems", Topics in Current Chemistry, 1998, pp. 162-188, vol. 194, Springer Verlag Berlin Heidelberg.

Smits, J.G., "Piezoelectric Micropump with Three Valves Working Peristatically", Sensors and Actuators, 1990, pp. 203-206, vol. A21-A23.

Sohn et al., "Capacitance cytometry: Measuring biological cells one by one," PNAS, 97(20):10687-10690 (2000).

Takahashi, A. et al. "Measurement of Intracellular Calcium", *Physiol. Rev.*, 1999, pp. 1089-1125, vol. 79, No. 4.

Tufte et al., "Silicon Diffused-Element Piezoresistive Diaphragms," J. Appl. Phys., Nov. 1962, pp. 3322-3327, vol. 33, No. 11.

Unger et al.; "Monolithic Microfabricated Valves and Pumps by Multilayer Soft Lithography", Science, Apr. 2000, pp. 113-116, vol. 288.

Unger et al.; "Single-molecule fluorescence observed with mercury lamp illumination", Biotechniques, Nov. 1999, p. 1008-1014, vol. 27, No. 5.

Van De Pol et al., "Micro Liquid Handling Devices—A Review", Micro Systems Technologies, 1990, pp. 799-805, vol. 90.

Vieider et al.; "A Pneumatically Actuated Micro Valve with a Silicon Rubber Membrane for Integration with Fluid Handling Systems", Proceedings of Transducers '95, the 8th International Conference on Solid-State Sensors and Actuators and Eurosensors IX, held in Stockholm, Sweden, on Jun. 25-29, 1995, pp. 284-286, Stockholm, Sweden.

Washizu et al., "Molecular Dielectrophoresis of Biopolymers," IEEE Transactions on Industry Applications, 1994, 30(4):835-843.

Wooley et al., "Functional Integration of PCR Amplification and Capillary Electrophoresis in a Microfabricated DNA Analysis Device," Anal. Chem., 68:4081-4086 (1996).

Xia et al., "Complex Optical Surfaces Formed by Replica Molding Against Elastomeric Masters," Science, 1996, 273:347-349.

Xia et al., "Micromolding of Polymers in Capillaries: Applications in Microfabrication," Chemistry of Materials, 8(7):1558-1567 (1996).

Xia et al., "Soft Lithography," Angew. Chem. Int. Ed., 1998, 37:551-575.

Xu, X. et al. "Detection of programmed cell death using fluorescence energy transfer", *Nucleic Acids Res.*, 1998, pp. 2034-2035, vol. 26, No. 8.

Yang et al. "A Mems Thermopneumatic Silicone Membrane Valve", Proceedings of IEEE 10th Annual International Workshop on MicroElectro Mechanical Systems, Sensors and Actuators, 1998, A64(1):101-108.

Yang et al., "A MEMS Thermopneumatic silicone Membrane Valve," Proceedings of the IEEE 10th Annual Workshop on Micro Electro Mechanical Systems Workshop (MEMS '97), held Jan. 26-30, 1997 in Nagoya, Japan, pp. 114-118 (1997).

Young et al. "Contoured elastic-membrane microvalves for microfluidic network integration," J. Biomechanical Engineering, 1999, 121:2-6.

Zaccolo, M. et al. "A genetically encoded, fluorescent indicator for cyclic AMP in living cells", *Nat Cell Biol*, 2000, pp. 25-29, vol. 2, No. 1.

Zdeblick et al. "A Microminiature Electric-to-Fluidic Valve", *Transducers '87, The 4th International Conference on Solid-State Sensors and Actuators*. Reprinted in *Micromechanics and MEMS Classic and Seminal Papers to 1990*, 1997, pp. 437-439, IEEE Press, USA.

Kenis et al. "Microfabriation Inside Capillaries Using Multiphase Laminar Flow Patterning," Science, 1999, 285:83-85.

Ahn et al., "Fluid Micropumps Based on Rotary Magnetic Actuators," Proceedings of 1995 IEEE Micro Electro Mechanical Systems Workshop (MEMS '95), held in Amsterdam, Netherlands on Jan. 29-Feb. 2, 1995, pp. 408-412.

Belgrader et al., "PCR Detection of Bacteria in Seven Minutes," Science, 284(5413):449-450 (1999).

Bretchel et al.; "Control of the electroosmotic flow by metal-salt-containing buffers", J Chromatography A, 1995, pp. 97-105, vol. 716.

Chaudhari et al., "Transient Liquid Crystal Thermometry of Microfabricated PCR Vessel Arrays," J. Microelectromechanical Systems, 7(4):345-355 (1998).

Ibrahim et al., "Real-Time Microchip PCT for Detecting single-Base Differences in Viral and Human DNA," Anal. Chem., 70:2013-2017 (1998).

Jacobson, K. et al.; "International Workshop on the Application of Fluorescence Photobleaching Techniques to Problems in Cell Biology", Workshop Summary, Federation Proceedings, 1983, pp. 72-79, vol. 42.

Jung et al., "Chemical and Physical Interactions at Metal/Self-Assmbled Organic Monolayer Interfaces," Critical Reviews in Solid State and Material Sciences, 1994, pp. 2-10, vol. 19, No. 1.

Kopp et al. "Chemical Amplification: Continuous-Flow PCR on a Chip", Science, 1998, 280:1046-1048.

Kuhn et al. "Silicon Charge Electrode Array for Ink Jet Printing", IEEE Transactions on Electron Devices, 1978, pp. 1257-1260, vol. ED-25, No. 10.

Lin et al. "Free-Space Micromachined Optical Switches for Optical Networking," IEEE J. Selected Topics in Quantum Electronics, 1999, pp. 4-9, vol. 5, No. 1.

Lucy et al., "Characterization of the Cationic Surfactant Induced Reversal of Electroosmotic Flow in Capillary Electrophoresis," Anal. Chem., 1996, pp. 300-305, vol. 68.

Maluf, N., An Introduction to Microelectromechanical Systems Engineering, Artech House Publishers, Boston London pp. 42-45.

Nakano et al., "High Speed Polymerase Chain Reaction in Constant Flow," Biosci. Biotech. Biochem., 58(2):349-352 (1994).

Pethig & Markx "Applications of dielectrophoresis in biotechnology," Tibtech, 15:426-432 (1997).

Qin et al., "Photolithography with transparent reflective photomasks," J. Vac.Sci. Technology, 16(1):98-103 (1998).

Roylance et al., "A Batch-Fabricated Silicon Accelerometer", IEEE Transactions on Electron Devices, Dec. 1979, pp. 1911-1917, vol. ED-26, No. 12.

Tyagi et al., "Molecular Beacons: Probes that Fluoresce upon Hybridization," Nature Biotechnology, 14:303-308 (1996).

Ullmann's Encyclopedia of Industrial Chemistry, Sections 6 to 6.3, Topic: Carbon Black, Sixth Edition, 1999.

Van De Pol, F.C.M. et al. "A Thermo-Pneumatic Actuation Principle for a Microminiature Pump and Other Micromechanical Devices" Sensors and Actuators, May 3, 1989, pp. 139-143, vol. 17, Nos. 1-2.

Yazoi et al. "Micromachined Inertial Sensors," Proceedings of IEEE, 1998, 86(8): 1640-1659.

Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.

Zengerle et al., "Performance Simulation of Microminiaturized Membrane Pumps," from 7th International Conference on Solid-State Sensors and Actuators held Jun. 7-10, 1993 in Yokohama Japan, pp. 106-109.

"Biochips," Nature Biotechnology, vol. 18, Supplement 2000, pp. IT43-IT44, 2000.

"Chapter 9: Microfluidic Devices," Micromachined Transducers Sourcebook, pp. 779-882, 1998.

"Electro Microfluidic Dual In-Line Package (EMDIP)," Sandia National Laboratories, 2 pages, no date.

"Last Chance For Micromachines," The Economist Technology Quarterly, printed from website http://www.economist.com/science/displayStory.cfm?Story_ID=442930 on Jan. 25, 2001, 8 pages, Dec. 7, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ashkin, A. et al., "Optical Trapping And Manipulation Of Single Cells Using Infrared Laser Beams," Nature, vol. 330, No. 24, pp. 769-771, Dec. 31, 1987.

Ashkin, A. et al., "Optical Trapping And Manipulation of Viruses And Bacteria," Science, vol. 235, pp. 1517-1520, Mar. 20, 1987.

Ballantyne, J. P. et al., "Selective Area Metallization By Electro-Beam Controlled Direct Metallic Deposition," J. Vac. Sci. Technol., vol. 10, No. 6, pp. 1094-1097, Nov. 1973.

Belgrader, Phillip et al., "Rapid Pathogen Detecting Using A Microchip PCR Array Instrument," Clinical Chemistry, vol. 44, No. 10, pp. 2191-2194, 1998.

Black, Harvey, "Tiny Technology Promises Tremendous Profits," The Scientist, vol. 15, No. 21, 4 pages, Oct. 29, 2001.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brush, Michael, "Automated Laboratories," The Scientist, vol. 13, No. 4, 10 pages, Feb. 15, 1999.

Buican, Tudor N. et al., "Automated Single-Cell Manipulation And Sorting By Light Trapping," Applied Optics, vol. 26, No. 24, pp. 5311-5316, Dec. 15, 1987.

Burbaum, Jonathan J. et al., "New Technologies For High-Throughput Screening," Current Opinion in Chemical Biology, vol. 1, pp. 72-78, 1997.

Cai, Weiwen, et al., "High-Resolution Restriction Maps of Bacterial Artificial Chromosomes Constructed By Optical Mapping," Proc. Natl. Acad. Sci. USA, vol. 95, pp. 3390-3395, Mar. 1998.

Calkins, Kathryn, "Mycometrix: Rubber Chips," BioCentury, 2 pages, Oct. 16, 2000.

Castro, Alonso et al., "Fluorescence Detection And Size Measurement Of Single DNA Molecules," Analytical Chemistry, vol. 85, No. 7, pp. 849-852, Apr. 1, 1993.

Chiu, Chi-Sung et al., "Single Molecule Measurements Calibrate Green Fluorescent Protein Surface Densities On Transparent Beads For Use With 'Knock-In' Animals And Other Expression Systems," Journal of Neuroscience Methods, vol. 105, pp. 55-63, 2001.

Chou, Hou-Pu et al., "Multiple Disease Diagnostics On A Single Chip," Biophysics Lab, Caltech, pp. 1-4, Mar. 1, 2000.

Fettinger, J. C. et al., "Stacked Modules For Micro Flow Systems In Chemical Analyis: Concept And Studies Using An Enlarged Model," Sensors and Actuators B, vol. 17, pp. 19-25, 1993.

Fitzgerald, Deborah A., "Making Every Nanoliter Count," The Scientist, vol. 15, No. 21, 8 pages, Oct. 29, 2001.

Folch, A. et al., "Molding of Deep Polydimethylsiloxane Microstructures For Microfluidics And Biological Applications," Journal of Biomechnical Engineer, vol. 121, pp. 28-34, Feb. 1999.

Galambos, Paul et al., "Electrical And Fluidic Packaging Of Surface Micromachined Electro-Microfluidic Devices," 8 pages, no date.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Goodwin, Peter M. et al., "Rapid Sizing Of Individual Fluorescently Stained DNA Fragments By Flow Cytometry," Nucleic Acids Research, vol. 21, No. 4, pp. 803-806, 1993.

Greene, Chana, "Characterizing The Properties Of PDMS," pp. 1-11, Summer 2000.

Guérin, L. J. et al., "Simple and Low Cost Fabrication Of Embedded Micro-Channels By Using A New Thick-Flim Photoplastic," Transducers '97, 1997 International Conference on Solid-State Sensors and Actuators, Chicago, Illinois, pp. 1419-1422, Jun. 18-19, 1997.

Hicks, Jennifer, "Genetics And Drug Discovery Dominate Microarray Research," R&D Magazine, pp. 28-33, Feb. 1999.

Hofmann, Oliver et al., "Modular Approach To Fabrication Of Three-Dimensional Microchannel Systems in PDMS—Application To Sheath Flow Microchips," Lap on a Chip, vol. 1, pp. 108-114, 2001.

Horn, Howard, "Lab Chips Sector: Microtechnologies Are Changing Healthcare And More," Life Sciences, pp. 19-21, Mar. 20, 2001.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Kagan, C. R., "Organic-Inorganic Hybrid Materials As Semiconducting Channels In Thin-Film Field-Effect Transistors," Science, vol. 286, pp. 945-947, Oct. 29, 1999.

Kamentsky, Louis A. et al., "Spectrophotometer: New Instrument For Ultrarapid Cell Analysis," Science, vol. 150, pp. 630-631, Oct. 29, 1965.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Keller, Richard A. et al., "Single-Molecule Fluorescence Analysis In Solution," Applied Spectroscopy, vol. 50, No. 7, pp. 12A-30A, Jul. 1996.

Khoo, Melvin et al., "A Novel Micromachined Magnetic Membrane Microfluid Pump," pp. 1-4, no date.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Fully Integrated PCR-Capillary Electrophoresis Microsystems For DNA Analysis," Lab On A Chip, vol. 1, pp. 102-107, 2001.

Lagally, Eric T. et al., "Monolithic Integrated Microfluidic DNA Amplification And Capillary Electrophoresis Analysis System," Sensors and Actuators B, vol. 63, pp. 138-146, 2000.

Lammerink, T. S. J. et al., "Modular Concept For Fluid Handling Systems," IEEE, pp. 389-394, 1996.

Lessard, Guillaume A. et al., "A Scanning Apertureless Fluorescence Microscope," 8 pages, no date.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, Sid, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems In Poly(dimethylsiloxane)," Electrophoresis, vol. 21, pp. 27-40, 2000.

Oleschuk, Richard D. et al., "Analytical Microdevices For Mass Spectrometry," Trends In Analytical Chemistry, vol. 19, No. 6., pp. 379-388, 2000.

Samad, Akhtar et al., "Optical Mapping: A Novel, Single-Molecule Approach To Genomic Analysis," Genome Research, pp. 1-4, 1995.

Sanjoh, Akira et al., "Spatiotemporal Protein Crystal Growth Studies Using Microfluidic Silicon Devices," Journal of Crystal Growth, vol. 196, pp. 691-702, 1999.

Sklar, Larry A. et al., Sample Handling For Kinetics And Molecular Assembly In Flow Cytometry, SPIE, vol. 3256, pp. 144-153, 1998.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Van Den Berg, A. et al., "Micro Total Analysis Systems," Proceedings of the µTAS '94 Workshop, University of Twente, The Netherlands, 17 pages, Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vogelstein, Bert et al., "Digital PCR," Proc. Natl. Acad. Sci. USA, vol. 96, pp. 9236-9241, Aug. 1999.

Whelen, A. Christian et al., "The Role Of Nucleic Acid Amplification And Detection In The Clinical Microbiology Laboratory," Annu. Rev. Microbiol., vol. 50, pp. 349-373, 1996.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Wilbur, James L. et al., "Lithographic Molding: A Convenient Route To Structures With Sub-Micrometer Dimensions," Adv. Mater., vol. 7, No. 7, pp. 649-652, 1995.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xu, Bing et al., "Making Negative Poisson's Ratio Microstructures By Soft Lithography," Adv. Mater., vol. 11, No. 14, pp. 1186-1189, 1999.

Yang, T. J. et al., "An Apertureless Near-Field Microscope For Fluorescence Imaging," Applied Physics Letters, vol. 76, No. 3, pp. 378-380, Jan. 17, 2000.

Yang, Xing et al., "A Lower Power MEMS Silicone/Parylene Valve," Solid-State Sensor and Actuator Workshop, Hilton Head Island, South Carolina, 4 pages, Jun. 7-11, 1998.

Fig. 1A
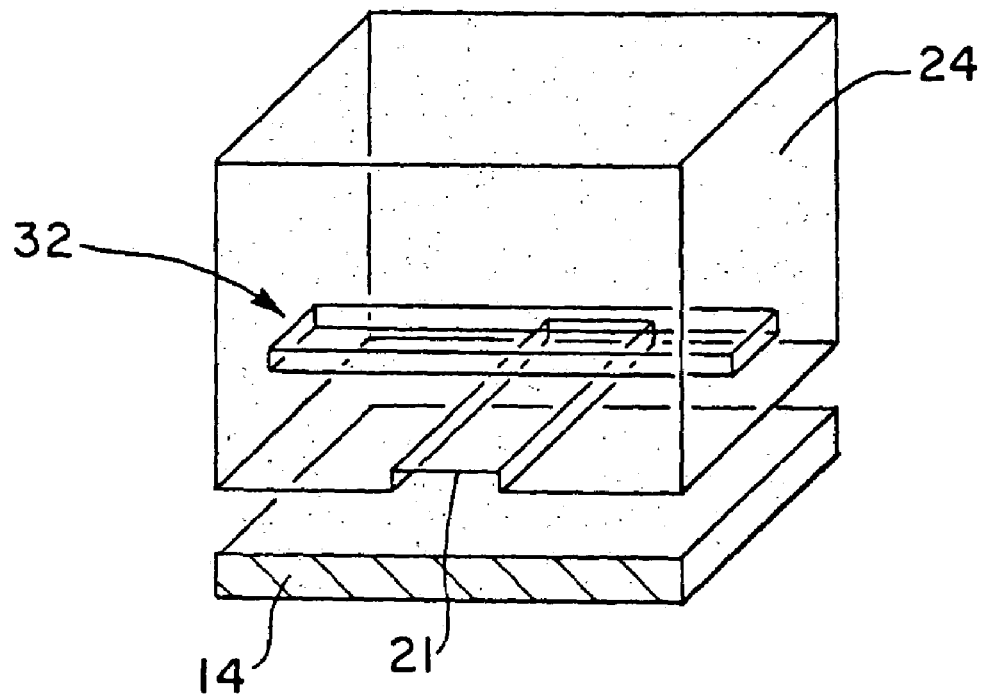
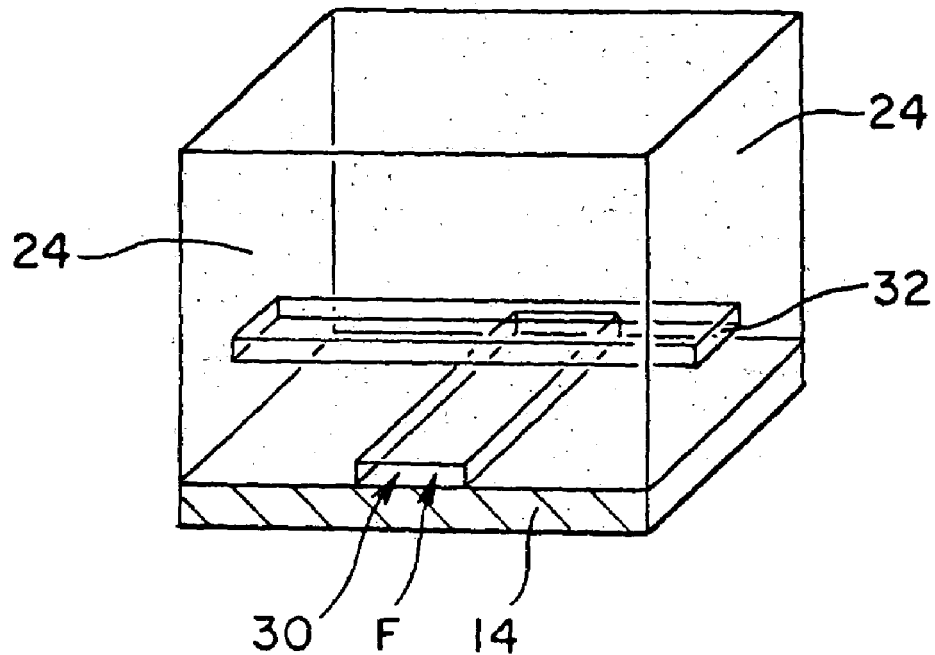
Fig. 1B

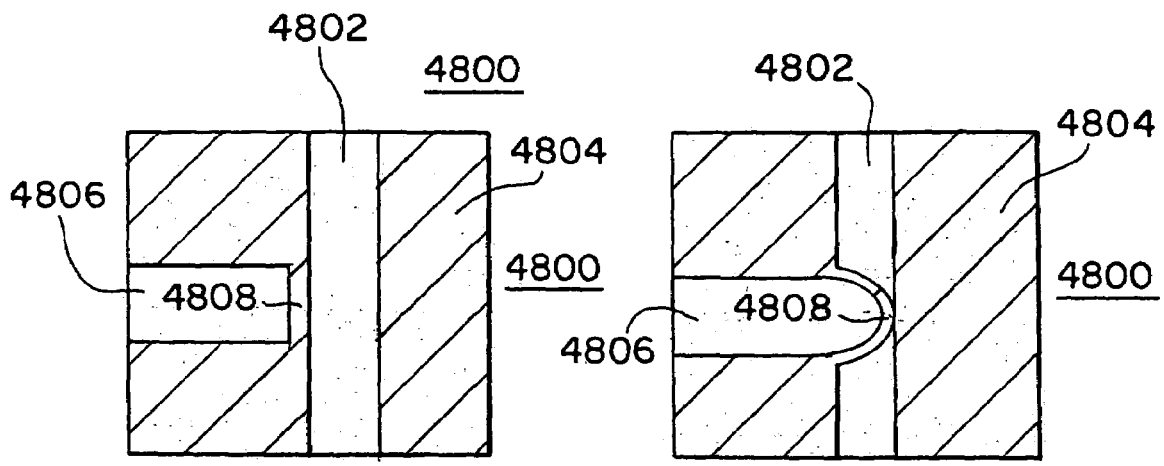
*Fig. 3A*  *Fig. 3B*
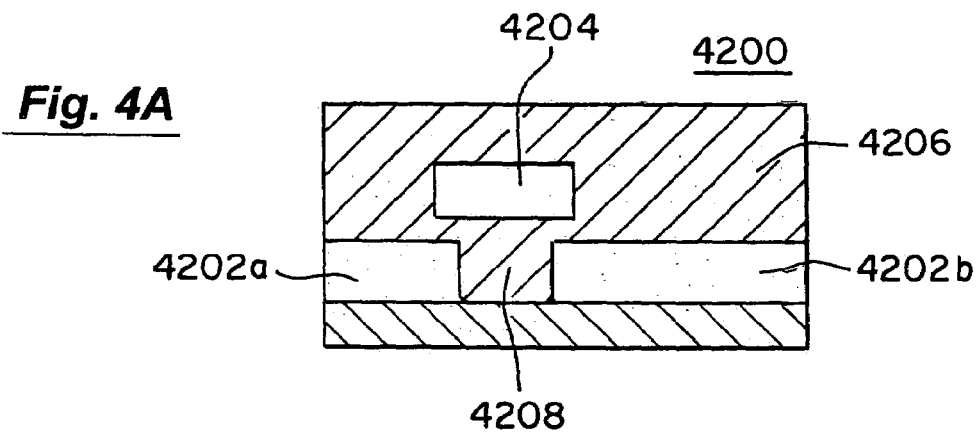
*Fig. 4A*
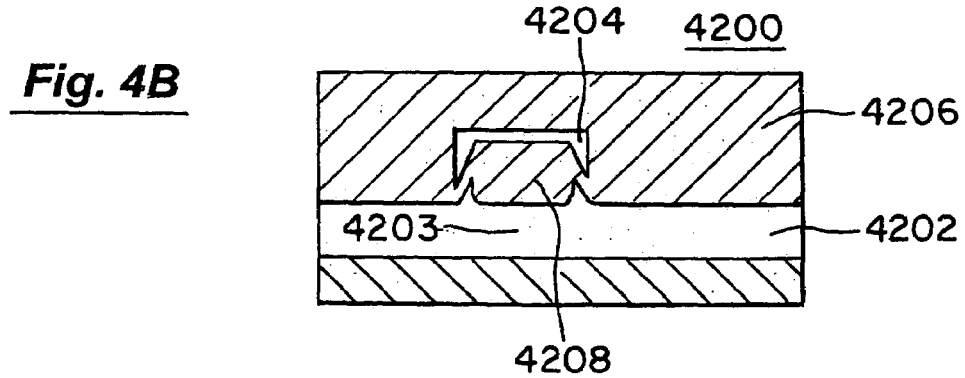
*Fig. 4B*

APPARATUS AND METHODS FOR CONDUCTING ASSAYS AND HIGH THROUGHPUT SCREENING

CROSS-REFERENCES TO RELATED APPLICATIONS

This application is the U.S. National Stage of International Application No. PCT/US01/44869, filed Nov. 16, 2001, which claims the benefit of U.S. Provisional Patent Application Nos. 60/249,327, filed Nov. 16, 2000, 60/281,946, filed Apr. 6, 2001, and 60/281,948, filed Apr. 6, 2001, all of Which are incorporated herein by reference in their entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. HG-01642-02 awarded by the National Institutes of Health.

FIELD OF THE INVENTION

The present invention relates to microfluidic apparatus and methods for conducting a variety of assays and high throughput screening.

BACKGROUND OF THE INVENTION

There are several goals in the development of biological assays, including utilization of a minimal amount of assay components and sample, simplicity in operation and high throughput capability. Assays preferably require a minimal amount of assay components in order to minimize costs; this becomes a particular issue if certain assay components are expensive and/or a large number of assays are to be conducted. Ideally, assays require only a minimal amount of sample because often only a very limited amount of sample is available. The goal of simplicity of operation often means that the assay is preferably conducted in an integrated format in which all or most aspects of the assay can be conducted with a single device and minimal instrumentation. The goal of high throughput has become increasingly important in view of the trend in current research and drug discovery efforts to screen huge libraries of compounds to identify those that have a desired activity.

To address some of these problems, particularly the issue of minimizing the amount of sample and assay agents required to conduct an analysis, considerable effort has been invested in the development of microfluidic devices to conduct assays. These devices are characterized by using minute channels for the introduction, transport and mixing of the samples and agents necessary to conduct an assay. Unfortunately, current microfluidic devices suffer from a number of shortcomings that limit their usefulness. For example, current microfluidic devices often are manufactured from silicon chips with channels being etched into different silicon layers using established semi-conductor technologies. Such chips, however, are brittle and the stiffness of the material often necessitates high actuation forces. These forces and stresses can cause layers in a multilayer chip to separate from one another. The stiffness of the devices also imposes significant constraints on options for controlling solution flow through the microchannels.

Furthermore, solution flow is controlled at least in part through the use of electrodes to generate electric fields to move molecules and solution via, electrophoresis and/or electroosmosis. Reliance on electrodes, however, creates several problems. One problem is that gas is often generated at the electrodes. This can increase pressure within the device potentially causing separation of microfabricated layers. The increased pressure and gas bubbles can also interfere with solution flow through the channels. Additionally, often an elaborate network of electrodes is required in order to achieve the desired level of control over solution transport. Fabrication of such a network can be complicated and increases the expense of the devices. The need for such networks also becomes particularly problematic if a device is to be prepared that includes a large number of branch channels to facilitate multiplexed and high through, put assay capabilities. Moreover, the use of electrical fields to control solution flow can be problematic for applications involving cells as application of the electric fields can negatively affect the cells, often killing them. Consequently, there remains a significant need for improved microfluidic devices, particularly those that are amendable to a wide range of cellular assays and that have high throughput capabilities.

BRIEF SUMMARY OF THE INVENTION

A variety of microfluidic devices and methods for conducting assays and syntheses are provided herein. Unlike conventional microfluidic devices, the devices disclosed herein include elastomeric components. In some instances, the entire device is manufactured from elastomeric materials. The devices can be utilized in a wide variety of applications, including cell assays and high throughput screening applications, as well as in the synthesis of a variety of compounds.

One aspect of the present invention provides a microfluidic device comprising: (a) a main flow channel adapted to allow the flow of a solution therethrough; (b) a plurality of branch flow channels, wherein each branch flow channel is in fluid communication with the main flow channel and comprises a detection region; (c) a plurality of control channels; and (d) a plurality of valves operatively disposed with respect to the main flow channel and/or the plurality of branch flow channels to regulate flow of the solution through the main and branch flow channels. Each of the valves comprises one of the control channels and an elastomeric segment that is deflectable into or retractable from the main or branch flow channel upon which the valve operates in response to an actuation force applied to the control channel. When the elastomeric segment is positioned in the flow channel, it restricts the flow of solution therethrough.

In one embodiment, the control channel of each valve is separated from the flow channel in which the valve operates by the elastomeric segment.

In another embodiment, the elastomeric segment is deflectable into the branch flow channel. While in another embodiment, the elastomeric segment is retractable from the branch flow channel.

Still in another embodiment, the microfluidic device further comprises a solution inlet in fluid communication with the main flow channel for introduction of the solution. In addition, the microfluidic device can further comprise a second solution inlet for each branch flow channel in fluid communication therewith for introduction of a second solution. Furthermore or alternatively, the microfluidic device can comprise an auxiliary inlet in fluid communication with the main flow channel. In addition, it can also comprise an inlet flow channel, in fluid communication with the main flow channel. Preferably, the solution inlet and the auxiliary inlet are in fluid communication with the inlet flow channel.

Yet in another embodiment, the microfluidic device comprises a detector operatively disposed with respect to at least one of the detection sections to detect an event or agent within the detection region. The detector can be a device which detects an optical signal from the detection region. In one particular embodiment, the detector can detect a fluorescence emission, fluorescence polarization or fluorescence resonance energy transfer. Preferably, the detector can perform time-resolved fluorescence measurements or fluorescence correlation spectroscopy. In another embodiment, the detection is an optical microscope, a confocal microscope or a laser scanning confocal microscope. Still in another particular embodiment, the detector is a non-optical sensor selected from the group consisting of a temperature sensor, a conductivity sensor, a potentiometric sensor and an amperometric sensor.

Still in another embodiment, each branch flow channel is adapted to allow the flow of a second solution therethrough. In this manner, the solution, which flows through the main fluid channel can contain assay components for an assay that is conducted in each of the different branch flow channels and the second solution can contain a test agent.

In another embodiment, the main flow channel is one of a plurality of main flow channels, each adapted to allow the flow of a first solution therethrough and in fluid communication with each of the branch flow channels.

In yet another embodiment, each of the branch flow channels intersect with the main flow channel at a different intersection, and further comprising a chamber located at each of the intersections, the chamber being adapted to collect solution therein.

Yet still in another embodiment, the microfluidic device further comprises a plurality of pumps. Preferably, each pump is operatively disposed with respect to one of the branch flow channels such that solution flow through each of the branch flow channels can be regulated by one of the pumps. In one particular embodiment, each of the plurality of pumps comprises at least three control channels each formed within an elastomeric material and separated from the branch flow channel by a section of an elastomeric membrane, the membrane being deflectable into the branch flow channel in response to an actuation force.

Still in another embodiment, the microfluidic device further comprises a plurality of mixers. Each mixer is operatively disposed with respect to one of the branch flow channels and is adapted to receive and mix different solutions flowing through one of the branch flow channels. Furthermore, an operatively disposed temperature controller can be present to regulate temperature within the mixer. Preferably, the mixer comprises (i) an inlet section and an outlet section
(ii) a looped flow channel in fluid communication with the inlet and outlet section; and
(iii) two sets of control channels, each set comprising at least three control channels, and each control channel separated from the looped flow channel by an elastomeric, membrane that is deflectable into the looped flow channel in response to an actuation force, and wherein the mixer is inserted into one of the branch flow channels such that solution from the branch flow channel can enter via the inlet section and reenter the branch flow channel via the outlet section, and solution within the mixer can be cycled through the looped flow channel by actuating the control channels with the actuation force which is applied to the control channels within a set in a repeating sequence. Moreover the detection section can also comprise the mixer.

In another embodiment, the microfluidic device, further comprises a plurality temperature controllers. Each temperature controller is operatively disposed with respect to one of the branch channels. Such temperature controller can be operative disposed within the microfluidic device to regulate temperature within the detection section.

Still in another embodiment, the microfluidic device further comprises a plurality of separation units, where each separation unit is operatively disposed with respect to one of the branch flow channels. Preferably, each, separation unit comprises a semi-permeable membrane that separates one of the branch flow channels and a collection channel. The membrane allows passage of certain agents in a solution flowing through the branch flow channel to pass through the semi-permeable membrane into the collection flow channel. Alternatively, the separation unit comprises a separation material that separates molecules on the basis of affinity, size, charge or mobility.

Yet in another embodiment, the microfluidic device further comprises (e) an inlet in fluid communication with the main flow channel for introduction of the first solution and an inlet for each branch flow channel in fluid communication therewith for introduction of the second solution, the first solution containing-assay components for an assay that is conducted in each of the different branch flow channels and the second solution containing a test agent; (f) a plurality of chambers positioned at points where the main flow channel and the branch flow channels intersect, the chambers being adapted to collect solution therein; (g) a plurality of pumps, each pump being operatively disposed with respect to one of the branch flow channels such that solution flow through each of the branch flow channels can be regulated by one of the pumps; and (h) plurality of mixers, each mixer being operatively disposed with respect to one of the branch flow channels and being adapted to receive and mix different solutions flowing through one of the branch flow channels.

In yet another embodiment, the microfluidic device further comprises a pair of valves operatively disposed with respect to each of the branch flow channels. The pair of valves are preferably disposed with respect to one another such that when the elastomeric segment of each valve of the pair extends into the branch flow channel a holding space is formed between the segments in which the solution can be retained. In addition, the microfluidic device can further comprises a plurality of control valves operatively disposed with respect to the main flow channel. Preferably, the control valves are positioned along the main flow channel such that by selectively actuating the control valves solution can be controllably introduced into the branch flow channels. Moreover, the control valves each comprise one of the control channels and an elastomeric segment that is deflectable into or retractable from the main flow channel in response to an actuation force applied to the control channel. Furthermore, the elastomeric segments of at least one pair of valves each comprise one or more protrusions. The protrusions are adapted to allow for the solution to flow through the holding space once the elastomeric segments are deflected into the branch flow channel while retaining a particle of a predetermined size that is present in the solution within the holding space of the at least one pair of valves. The particle can be any non-soluble material including cells.

Preferably, the branch flow channel is present within an elastomeric material. Moreover, a segment of the branch flow channel opposite the elastomeric segment of each valve of at least one pair of valves comprises one or more elastomeric protrusions. The protrusions adapted to allow for solution to flow through the holding space once the elastomeric segment is deflected into the branch flow channel while retaining a particle of a predetermined size that is present in the solution within the holding space of the at least one pair of valves.

In another embodiment, the branch flow channels are formed within an elastomeric material; the elastomeric segments of at least one pair of valves comprise one or more protrusions; a segment of the branch flow channel opposite the elastomeric segments of the at least one valve pair comprises one or more protrusions, and wherein the protrusions of the elastomeric segment and the protrusions of the branch flow channel are adapted to allow for solution to flow through the holding space of the at least one valve pair once the elastomeric segments are deflected into the branch flow channel while retaining a particle of a predetermined size that is present in the solution within the holding space.

Still in another embodiment, the microfluidic device further comprises a plurality of chambers positioned at points where an inlet flow channel and the branch flow channels intersect, the chambers adapted for storing solution.

Yet in another embodiment, the microfluidic device further comprises a plurality of branch control valves, wherein a branch control valve is operatively disposed with respect to each of the branch flow channels and each branch control valve comprises an elastomeric segment that separates one of the branch flow channels and one of the control channels and that is deflectable into or retractable from the branch flow channel upon which the valve operates in response to an actuation force applied to the control channel.

In one embodiment, each branch flow channel is in communication with a pump. Preferably, the pump comprises at least three control channels, each formed within an elastomeric material and separated from one of the branch flow channels by an elastomeric membrane, the membrane being deflectable into the branch flow channel in response to an actuation force.

In another embodiment, each branch flow channel comprises a particle, enrichment section that selectively retains particles of interest. Preferably, the enrichment section contains a ligand that specifically binds to particle(s) that are present in the solution. In addition, the detection region, preferably, includes the holding space and a detector is disposed to detect particle(s) within the holding spaces within the plurality of branch channels.

In one particular embodiment, the detection region includes the hold space.

In another embodiment, the detection region is located at a section of the branch flow channel other than the holding space.

Another aspect of the present invention provides a microfluidic device for conducting cellular assays, comprising (a) a main flow channel, (b) an input adapted to receive a first solution and in fluid communication with the main flow channel, whereby solution introduced into the input can flow into the main flow channel; (d) a plurality of control channels; (e) a plurality of chambers positioned along the main flow channel and in fluid communication therewith, such that solution flowing through the main flow channel can be stored in the chambers; (f) a plurality of branch flow channels, wherein each branch flow channel is in fluid communication with a branch inlet, each branch inlet adapted to receive a second solution and in fluid communication with one of the chambers, different branch flow channels being in fluid communication with different chambers; (g) a plurality of storage valves, wherein a pair of storage valves are operatively disposed with respect to each of the branch flow channels, and wherein each of the storage valves comprises an elastomeric segment that separates one of the branch flow channels and one of the control channels and that is deflectable into or retractable from the flow channel upon which the valve operates in response to an actuation force applied to the control channel, the storage valves of a pair being disposed with respect to one another such that when the elastomeric segment of each storage valve of the pair extends into the branch flow channel a holding space is formed between the segments in which one or more cells can be retained; and (h) one or more pumps to transport the first and/or second solution through the branch flow channels. Preferably, each pump comprises at least three control channels, each formed within an elastomeric material and separated from one of the branch flow channels by a section of an elastomeric membrane, the membrane being deflectable into the branch flow channel in response to an actuation force.

Still another aspect of the present invention provides a method of conducting a cellular analysis, comprising
   (a) providing a microfluidic device comprising
      (i) a flow channel comprising a detection region;
      (ii) a plurality of control channels; and
      (iii) a pair of storage valves operatively disposed with respect to the flow channel, wherein each storage valve comprises one of the control channels, which control channel is separated from the flow channel by an elastomeric membrane, the elastomeric membrane being deflectable into the flow channel in response to an actuation force applied to the control channel, the two control channels of the storage valves being disposed relative to one another such that deflection of the elastomeric membrane of the respective control channels into the flow channel forms a holding space within the flow channel;
   (b) introducing a sample containing one or more cells into the flow channel;
   (c) actuating the storage valves to hold at least one of the cells within the holding space; and
   (d) performing an assay by contacting the cells within the holding space with a solution containing one or more assay agents.

Preferably, the elastomeric membranes of the storage valves each comprise one or more protrusions. The protrusions are adapted to allow for solution to flow through the holding space once the elastomeric membranes are deflected into the flow channel while retaining the cell(s) within the holding space.

In one embodiment, the flow channel is formed within an elastomeric, material and a segment of the flow channel opposite the elastomeric membrane of the storage valves comprises one or more elastomeric protrusions, the protrusions adapted to allow for solution to flow through the holding space once the elastomeric membranes are deflected into the flow channel while retaining the cell(s) within the holding space.

In another embodiment, the flow channel is formed within an elastomeric material; the elastomeric segments of the storage valves comprise one or more protrusions; a segment of the flow channel opposite the elastomeric membrane of each storage valve comprises one or more protrusions, and wherein the protrusions of the elastomeric membrane and the protrusions of the branch flow channel are adapted to allow for solution to flow through the holding space once the elastomeric membranes are deflected into the branch flow channel while retaining the cell(s) within the holding space.

Still in another embodiment, the microfluidic device further comprises a chamber adapted for storing solution in fluid communication with the flow channel and the method further comprises transporting solution and/or cells back and forth between the chamber and the holding space.

Preferably, the flow channel is in communication with a pump. And the sample is transported through the flow channel under the action of the pump. Preferably, the pump comprises at least three of the control channels, each formed within an elastomeric material and separated from the flow channel by an elastomeric membrane, each membrane being deflectable into the flow channel in response to an actuation force, whereby sample is transported along the flow channel.

In one embodiment, the flow channel comprises a cell enrichment section that selectively retains cells of interest, and the method further comprises transporting the sample through the enrichment section. Preferably, the enrichment section contains a ligand that specifically binds to a receptor on target cells.

In one embodiment of the present invention, the assaying step comprises detecting an event and/or agent within the detection section with a detector.

In another embodiment, the assay step comprises flowing a solution through the holding spaces after the storage valves have been actuated.

In one particular embodiment, the solution flowed through the holding spaces is culture medium for the cells within the holding space.

In another embodiment, the solution comprises a cellular stain.

Still in another embodiment, the assay comprises detecting cellular morphology.

Yet in another embodiment, the assay is a cell reporter assay.

In another embodiment, the assay comprises detecting binding between a ligand and a cell receptor.

In another embodiment, the assay comprises measuring cell membrane potential.

Still in another embodiment, the assay is an assay for detecting a toxic effect on cells or a cell death assay.

Yet in another embodiment, the assay is a cell proliferation assay, an assay for dysfunction of mitochondrial membrane potential, caspase activation, or cytochrome c release from cells.

In still yet another embodiment, the assay is a cell lysis assay.

In another embodiment, the assay is an antimicrobial assay.

Another aspect of the present invention provides a method of conducting a cellular analysis, comprising
 (a) providing a microfluidic device comprising
  (i) a main flow channel;
  (ii) a plurality of branch flow channels, each branch flow channel being in fluid communication with the main flow channel;
  (iii) a plurality of control channels; and
  (iv) a plurality of storage valves, wherein a pair of storage valves are operatively disposed with respect to each of the branch flow channels, and wherein each of the storage valves comprises an elastomeric segment that separates one of the branch flow channels and one of the control channels and that is deflectable into or retractable from the flow channel upon which the valve operates in response to an actuation force applied to the control channel, the storage valves of a pair being disposed with respect to one another such that when the elastomeric segment of each storage valve of the pair extends into the branch flow channel a holding space is formed between the segments in which one or more cells can be retained;
 (b) introducing a solution containing one or more cells into each of the branch flow channels;
 (c) actuating the storage valves within each of the branch flow channels to form the holding space to hold at least one of the cells within the sample introduced into the branch flow channel; and
 (d) performing an assay by contacting the cells within the holding space with a solution containing one or more assay agents.

In one particular embodiment, different cells are introduced into different branch flow channels and the assaying step comprises contacting the cells within each branch flow channel with the same assay solution.

In another embodiment, cells of the same type are introduced into each of the flow channels and the assaying step contacting the cells within different branch flow channels with different assay solutions.

Yet another aspect of the present invention provides a method for conducting an assay comprising, comprising:
 (a) providing a microfluidic device comprising
  (i) a main flow channel;
  (ii) a plurality of branch flow channels, each in fluid communication with the main flow channel and comprising a detection section;
  (iii) a plurality of control channels; and
  (iv) a plurality of valves operatively disposed with respect to the main flow channel and/or the plurality of branch flow channels to regulate flow of the first and second solutions therethrough wherein each of the valves comprises one of the control channels and an elastomeric segment that is deflectable into or retractable from the main or branch flow channel upon which the valve operates in response to an actuation force applied to the control channel, the elastomeric segment when positioned in the flow channel restricting solution flow therethrough
 (b) introducing a first assay solution into the main flow channel and a second assay solution into each of the plurality of branch flow channels;
 (c) actuating one or more of the valves to control flow of the first and second assay solutions through the main and branch flow channels, whereby the first and second assay solutions are brought into contact with one another to form an assay solution mixture; and
 (d) assaying each of the assay solution mixtures for a desired property within the detection section.

In one embodiment, the control channel of each valve is separated from the flow channel in which the valve operates by the elastomeric segment. In particular, the method is a method for screening a plurality of target agents for the desired property; the first assay solution is a solution comprising one or more assay agents and the second assay solution is a solution comprising one of the test compounds; the introducing step comprises introducing a different test compound into each of the plurality of branch flow channels; and the assaying step comprises identifying at least one test compound having the desired activity.

In another embodiment, the microfluidic device further comprises a first inlet in fluid communication with the main flow channel and a second inlet for each branch flow channel, and wherein the first assay solution is introduced via the first inlet and the second assay solution introduced via the second inlet.

Yet in another embodiment, the microfluidic device further comprises a plurality of pumps, each pump being operatively disposed with respect to one of the branch flow channels, and wherein the method further comprises actuating the pump of each branch channel to transport the first and/or second assay solution through the branch flow channel. Preferably, each of the plurality of pumps comprises a at least three control channels each formed within an elastomeric material and separated from one of the branch flow channels by a section of an elastomeric membrane, the membrane being deflectable into the branch flow channel from which it is separated in response to an actuation force.

Still in another embodiment, the microfluidic device further comprises a plurality of mixers, each mixer being operatively disposed with respect to one of the branch flow channels, and wherein the method further comprises mixing the first assay solution and the second assay solution with the mixer to form the assay solution mixture prior to the assaying step. Preferably, the mixer comprises (i) an inlet section and an outlet section (ii) a looped flow channel in fluid communication with the inlet and outlet section; and (iii) two sets of control channels, each set comprising at least three control channels, and each control channel separated from the looped flow channel by an elastomeric membrane that is deflectable into the looped flow channel in response to an actuation force, and wherein the mixing step comprises transporting the first and second assay solution into the mixer via the inlet section and mixing the first and second solution in the looped flow channel by applying the actuation force to the control channels within a set as part of a repeating sequence.

In still another embodiment the microfluidic device further comprises a plurality of temperature controllers, each temperature controller being operatively disposed with respect to one of the branch channels, and the method further comprises actuating the temperature controller to regulate the temperature of the first assay solution, the second assay solution and/or the assay solution mixture. Preferably, the temperature controller is disposed to regulate the temperature of the assay solution mixture within the detection section.

Yet in another embodiment, the microfluidic device further comprises a plurality of mixers, each mixer being operatively disposed with respect to one of the branch flow channels, and wherein the method further comprises mixing the first assay solution and the second assay solution with the mixer to form the assay solution mixture prior to the assaying step and wherein the temperature controller is disposed to regulate the temperature of the assay solution mixture within the mixer.

Still in another embodiment, the microfluidic device further comprises a plurality of separation units, each separation unit being positioned within one of the branch flow channels, and wherein the method further comprises (e) transporting a mixture of the first and second assay solutions through the separation unit whereby one or more unwanted compounds are removed to form the assay solution mixture; and (f) transporting the assay solution mixture to the detection section.

Yet still in another embodiment, the microfluidic device further comprises a plurality of mixers and a plurality of separation units, each mixer being operatively disposed with respect to one of the branch flow channels; and each separations unit being positioned within one of the branch flow channels, and wherein the method further comprises (e) mixing the first assay solution and the second assay solution with the mixer; (f) transporting the mixture of the first and second as say solutions through the separation unit whereby one or more unwanted compounds are removed to form the assay solution mixture; and (g) transporting the assay solution mixture to the detection section. Preferably, each separation unit comprises a semi-permeable membrane that separates one of the branch flow channels and a collection channel, the membrane allowing passage of certain agents in the first or second assay solution or a mixture thereof flowing through the branch flow channel to pass through the membrane and into the collection flow channel. Alternatively, the separation unit comprises a separation material that separates molecules on the basis of affinity, size, charge or mobility.

Still in another embodiment, the microfluidic device further comprises a detector operatively disposed with respect to at least one of the detection sections, and the assaying step comprises detecting an event or agent within the detection section.

Yet in another embodiment, the desired property is the ability of the at least one test agent to promote or inhibit binding between a ligand and an antiligand. In one particular embodiment, the antiligand is a protein receptor and the ligand is the receptor's cognate ligand. In another particular embodiment, the ligand is an antigen and the antiligand is an antibody that specifically binds to the antigen. Still in another particular embodiment, the antiligand is an enzyme and the ligand is an enzyme substrate or inhibitor of the enzyme. Yet still in another particular embodiment, the ligand is a nucleic acid and the antiligand is a nucleic acid binding protein.

Still in another embodiment, the desired property is the ability of the at least one test agent to trigger a signal transduction pathway.

Still yet in another embodiment, the desired property is the ability of the at least one test agent to inhibit microbial growth.

In another embodiments the desired property is the ability of the at least one test agent to trigger cell death.

Yet in another embodiment, the desired property is the ability of the at least one test agent to trigger apoptosis in a cell.

Still in another embodiment, the assay comprises assaying for inhibition of cell proliferation, assaying for dysfunction of mitochondrial membrane function, assaying for caspase activation or assaying for cytochrome c release from a cell.

Yet in another embodiment, the assaying step comprises conducting an assay in a homogenous format.

In another embodiment, the assaying step comprises conducting an assay in a heterogenous format.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton. et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in U.S. application Ser. No. 09/605,520, filed Jun. 27, 2000, U.S. application Ser. No. 09/724,784, filed Nov. 28, 2000, and PCT publication WO 01/01025, each of which are incorporated herein by reference in their entirety.

A "ligand" generally refers to any molecule that binds to an antiligand to form a ligand/antiligand pair. Thus, a ligand is any molecule for which there exists another molecule (i.e., the antiligand) that specifically or non-specifically binds to the ligand, owing to recognition of some portion or feature of the ligand.

An "antiligand" is a molecule that specifically or nonspecifically interacts with another molecule (i.e., the ligand).

As used herein, the term "binding pair" or "binding partners" refers to first and second molecules that specifically bind to each other such as a ligand and an antiligand. In general, "specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Binding partners need not be limited to pairs of single molecules. For example, a single ligand can be bound by the coordinated action of two or more antiligands.

Binding between binding pairs or binding partners results in the formation of a binding complex, sometimes referred to as a ligand/antiligand complex or simply as ligand/antiligand. Exemplary binding pairs include, but are not limited to: (a) a haptenic or antigenic compound in combination with a corresponding antibody or binding portion or fragment thereof; (b) nonimmunological binding pairs (e.g., biotin-avidini, biotin-streptavidin, biotin-Neutravidin); (c) hormone-hormone binding protein; (d) receptor-receptor agonist or antagonist; (e) lectin-carbohydrate; (f) enzyme-enzyme cofactor; (g) enzyme-enzyme inhibitor; (h) and complementary, polynucleotide pairs capable of forming nucleic acid duplexes.

An "analyte" refers to the species whose presence, absence and/or concentration is being detected or assayed.

"Polypeptide," "peptides" and "protein" are used interchangeably herein and include a molecular chain of amino acids linked through peptide bonds. The terms do not refer to a specific length of the product. The terms include post translational modifications of the polypeptide, for example, glycosylations, acetylations, phosphorylations and the like, and also can include polypeptides that include amino acid analogs and modified peptide backbones.

The term "antibody" as used herein includes antibodies obtained from both polyclonal and monoclonal preparations, as well as the following: (i) hybrid (chimeric) antibody molecules (see, for example, Winter et al. (1991) Nature 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose) polyribonucleotides (containing D-ribose), any other type of polynucleotide which is an N—or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, OR., as Neugene) polymers, and other synthetic sequence-specific nucleic acid polymers providing that the polymers contain nucleobases in a configuration which allows for base pairing and base stacking, such as is found in DNA and RNA.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "stringent conditions" refers to conditions under which a probe or primer will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. In other instances, stringent conditions are chosen to be about 20° C. or 25° C. below the melting temperature of the sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) Methods in Enzymology, vol. 152: Guide to Molecular Cloning Techniques, San. Diego: Academic Press, Inc. and Sambrook et al. (1989) Molecular Cloning: A Laboratory Manual, 2nd ed., vols. 1-3, Cold Spring Harbor Laboratory), both incorporated herein by reference. As indicated by standard references, a simple estimate of the $T_m$ value can be calculated by the equation: $T_m=81.5+0.41(\% \text{ G+C})$, when a nucleic acid is in aqueous solution at 1 M NaCl (see e.g., Anderson and Young, "Quantitative Filter Hybridization," in *Nucleic Acid Hybridization* (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions can also be achieved with the addition of destabilizing agents such as formamide.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site directed mutagenesis are also useful for modifying a heterologous nucleic acid.

An "exogenous" species is refers to a species that is not normally present in a cell, but can be introduced into a cell by one or more genetic, biochemical or other methods. Normal presence in the cell is determined with respect to the particular developmental stage and environmental conditions of the cell. Thus, for example, a molecule that is present only during embryonic development is an exogenous molecule with respect to a corresponding adult cell. An exogenous species can be, among other things, a small molecule, such as is generated by a combinatorial chemistry process, or a macromolecule such as a protein, nucleic acid, carbohydrate, lipid, glycoprotein, lipoprotein, polysaccharide, or any modified derivative of the above molecules, or any complex comprising one or more of the above molecules.

By contrast, an "endogenous" species is one that is normally present in a particular cell at a particular developmental stage under particular environmental conditions.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

The term "naturally occurring" as applied to an object means that the object can be found in nature.

A "small molecule" means a synthetic molecule having a molecular weight of less than 1000 daltons, more typically 500 daltons or less. Such molecules include, for example, monosaccharides, polysaccharides, polypeptides, sterols, amino acids, lipids and nucleic acids.

The phrase "specifically binds" generally refers to binding of a ligand and an antiligand, or vice versa, with greater affinity and specificity than to other components in the sample. Thus, the term refers to a binding reaction which is determinative of the presence of the ligand in the presence of a heterogeneous population of other biological compounds. Thus, under designated conditions, a specified ligand binds preferentially to a particular antiligand and does not bind in a significant amount to other molecules present in the sample. Typically, a molecule or ligand (e.g., an antibody) that specifically binds to an antiligand has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, $10^{10}$ $M^{-1}$ to $10^{11}$ $M^{-1}$ or higher.

A difference is typically considered to be "statistically significant" if the difference is greater than the level of experimental error. More specifically, a difference is statistically significant if the probability of the observed difference occurring by chance (the p-value) is less than some predetermined level. As used herein a "statistically significant difference" refers to a p-value that is <0.05, preferably <0.01 and most preferably <0.001.

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. The term "detectably labeled" means that an agent has been conjugated with a label or that an agent has some inherent characteristic (e.g., size, shape or color) that allows it be detected without having to be conjugated to a separate label.

BRIEF DESCRIPTION OF THE DRAWINGS

In certain drawings, pumps are denoted with a group of three dashed lines and valves denoted by a single dashed line.

FIGS. 1A and 1B are illustrations of an elastomeric block and the arrangement of a control and flow channel therein.

FIGS. 3A and 3B are plan views illustrating the operation of an exemplary side-actuated valve structure.

FIGS. 4A and 4B show one example of a normally closed valve structure.

FIG. 6A is a top schematic of the peristaltic pump. FIG. 6B is a sectional elevation view along line 24B-24B in FIG. 6A.

DETAILED DESCRIPTION

I. Overview

Figure 2A:
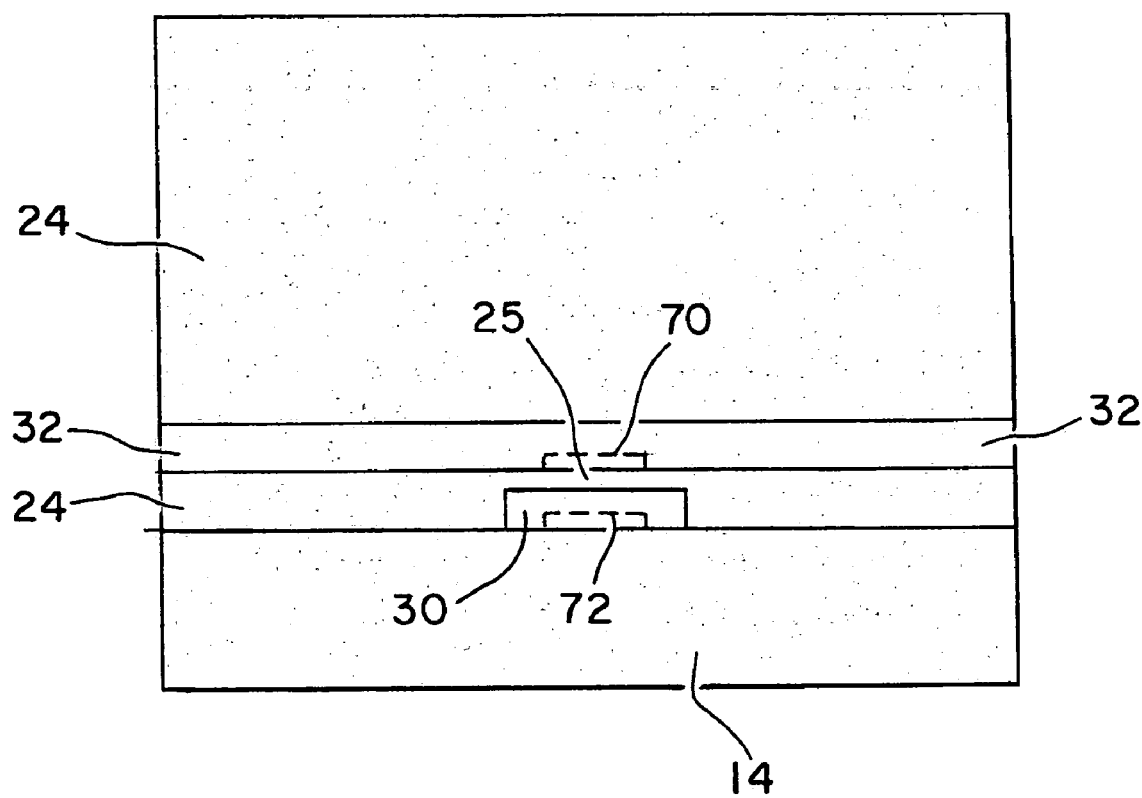
FIG. 2A is a sectional view of an elastomeric block showing the disposition of a flow and control channels with respect to one another in a valve and optional electrodes for actuating the valve.

Described herein are microfluidic devices and methods for conducting a variety of different assays, such as high throughput screening assays, cellular assays or assays involving cellular components, and syntheses, such as combinatorial syntheses. The microfluidic devices are characterized in part by including various components such as flow channels, control channels, valves and/or pumps, at least some of which are manufactured from elastomeric materials. This is in sharp contrast to conventional microfluidic devices that typically are based on silicon substrates (i.e., silicon chips).

The microfluidic devices in general include a main flow channel through which a solution (e.g., a solution containing one or more analytes or cells, or solutions containing various assay agents) can flow, one or more branch flow channels in fluid communication with the main flow channel and one or more valves operatively disposed with respect to the main and/or branch flow channels. The valves comprise a control channel separated from a flow channel by an elastomeric membrane or segment that can be deflected into or withdrawn from the flow channel upon actuation of the control channel (e.g., by applying pressure or a vacuum to the control channel). When the membrane extends into the flow channel, it blocks solution flow through the channel. The microfluidic devices also include a detection section within the flow channel(s) and can further include one or more detectors positioned to detect a signal associated with a particular agent or event within the detection section of the flow channel.

In some of the microfluidic systems, each of the branch flow channels includes a pair of valves for retaining a volume of solution therebetween. Accordingly, the valves are positioned relative to one another such that when the membranes of the two control channels associated with the valve pair extend into the branch channel, the membranes form a holding space within the flow channel that is bounded by the extended membranes. This holding space generally is of a size appropriate to hold one or more particles, e.g., cells. With certain devices the membrane includes teeth or a grate such that even when the valve is actuated solution containing assay reagents can flow into the space or a rinse solution can flow through the space to carry away agents, within the space while the particle(s), e.g., cell(s), within the space are retained. The microfluidic devices also usually include one or more detectors positioned to detect a signal associated with a particular agent or event within a detection section of the flow channel, which in some instances involves detection of a cell or other agent retained in the holding space.

The branch flow channels can have a variety of different configurations depending upon the nature of the application. The flow channels are usually formed within an elastomeric material; in some instances, the entire microfluidic device is part of a monolithic elastomeric block. In one embodiment of the present invention, the microfluidic devices include a plurality of branch flow channels branching off of the main flow channel. Each of the branch channels can include a set of valves as described herein to provide a holding space within each branch flow channel. In this way, different analyses or syntheses can be conducted in the different branch channels.

The microfluidic devices can include optional chambers or reservoirs. Such chambers or reservoirs can be positioned at the intersection between the main flow channel and the branch flow channels to provide a storage site for solutions introduced through the main flow channel and/or the branch flow channels. Additionally, the microfluidic devices can also optionally include one or more pumps for transporting solutions along and between the different flow channels. Certain pumps are characterized by including a plurality, preferably at least three, control channels that are separated from one of the flow channels by an elastomeric membrane that can be deflected into the flow channel when actuated. By actuating the control channels in a staggered fashion, a peristaltic effect can be induced.

In some devices, the branch channels can include a pair of valves for retaining a volume of solution therebetween. Accordingly, the valves are positioned relative to one another such that when the membranes of the two control channels of the valve pair extend into the branch flow channel, the membranes form a holding space within the flow channel. The branch channels can also includes optional mixers to mix and incubate solutions. Certain mixers include a looped flow path that includes a plurality of peristaltic pumps of the type just described to flow solution around the loop.

The microfluidic devices provided herein can be utilized in a number of different applications, for example, high throughput cellular assays. By controllably introducing different solutions into the different branch channels with the valves and transporting solutions between the main flow channel and branch channels (e.g., using the pumps described above), a number of different analyses or syntheses can be performed at the same time. Thus, the microfluidic devices can be used to conduct a number of different types of assays, including, for example, binding assays, cell reporter assays, toxicological assays, immunological assays, and single nucleotide polymorphism analysis.

The devices disclosed herein can be utilized to screen individual compounds and libraries of compounds to identify those having a desired effect in various in vitro model systems. For example, assays utilizing the microfluidic devices provided herein can be utilized to screen libraries of compounds for those capable of fully or partially inhibiting reactions or processes that have undesirable consequences. For instance, libraries can be screened to identify compounds that inhibit reactions or processes involved in the onset of disease or particular symptoms associated with the disease (e.g., bacterial and viral infections, hereditary diseases and cancer). Alternatively, individual compounds and libraries of compounds can be screened to identify particular compounds that activate or promoter reactions or processes of interest. Compounds showing activity in initial screening can then be subjected to other screens or modified and rescreened to identify compounds suitable for formulation as pharmaceutical agents in treating the disease or symptoms associated with the disease under investigation.

In general such screening methods involve introducing certain assay components (e.g., cells) into the different branch channels and then different test agents (e.g., from a combinatorial library) are selectively introduced into the different branch flow channels such that different agents are delivered to (different branch flow channels. The ability of the test agent to generate a particular response can be detected by monitoring the holding area within the branch flow channels. Similarly, the valves and pumps of the microfluidic devices can be utilized to controllably react different reactants in the different branch flow channels to perform combinatorial syntheses.

II. Microfluidic Elements

A number of elements that are commonly utilized in the microfluidic devices disclosed herein are described below. It should be recognized that these elements can be considered modules that can be combined in different ways to yield an essentially unlimited number of configurations. Further, using the following elements or modules one can tailor the microfluidic device to include those elements useful for the particular application(s) to be conducted with the device.

A. General

The microfluidic devices disclosed herein are typically constructed by single and multilayer soft lithography (MLSL) techniques and/or sacrificial layer encapsulation methods. Both of these methods are described in detail by Unger et al. (2000) Science 288:113-116, in U.S. patent application Ser. No. 09/605,520, filed Jun. 27, 2000, in U.S. patent application Ser. No. 09/724,784, filed Nov. 28, 2000, and in PCT publication WO 01/01025, all of which are incorporated herein in their entirety for all purposes. The microfluidic devices provided herein can include a variety of different components that are described in detail infra. These components can be arranged in a large number of different configurations depending upon the particular application. The following sections describe the general components that are utilized in the devices; these sections are followed with exemplary configurations that can be utilized in various types of assays, such as cellular assays and high throughput screening.

Although the devices can be manufactured exclusively from elastomeric materials, this is not a requirement. Thus, the devices need not be monolithic in nature; hybrid devices fusing elastomers and other materials such as silicon, glass or plastic substrates can be utilized. As described in further detail below, the elastomeric materials can be tailored to the particular application by modifying the internal surfaces of the channels of the microfluidic device.

B. Channels

The channels through which solution is transported in the microfluidic devices are typically formed at least in part if not entirely from elastomeric compounds. Separated from the flow channels by an elastomeric membrane are control channels which can be actuated to control or regulate solution, flow through the flow channels. As described in greater detail below in the section on valves, actuation of the control channel (e.g., pressurization or pressure reduction within the flow channel) causes the elastomeric membrane separating the flow and control channel to be extended into the flow channel, thus forming a valve that blocks solution flow in the flow channel. Typically, the flow and control channels cross one another at an angle.

The flow and control channels can be manufactured from two primary techniques. One approach is to cast a series of elastomeric layers on a micro-machined mold and then fuse the layers together. The second primary method is to form patterns of photoresist on an elastomeric layer in a desired configuration; in particular, photoresist is deposited wherever a channel is desired. These two different methods of forming the desired configuration of flow and control channels, as well as other details regarding channel. dimensions and shape, are described in considerable detail in PCT publication WO 01/01025, U.S. application Ser. No. 09/605,520, filed Jun. 27, 2000, U.S. application Ser. No. 09/724,784, filed Nov. 28, 2000, and by Unger et al. (2000) Science 288:113-116, each of which is incorporated herein by reference in its entirety.

C. Sample Inputs

There are a number of different options for introducing a solution into a flow channel. One option is to simply inject solution into a flow channel using a needle, for example. One can also pressurize a container of solution to force solution from the container into a flow channel. A related approach involves reducing pressure at one end of a flow channel to pull solution into a distal opening in the flow channel.

Individual input/inlet lines can be formed that can be loaded manually using single channel micropipettors. The microfluidic devices can be sized according to industry size-specifications (e.g., footprint is 127.76 0.12×85.47 0.12 mm) for plate readers and robotics and are designed to interface with generic multichannel robotic pipettors/samplers with standardized interwell spacings (pitch). Dimensional standards for these types of plate/devices are described at http://www.tomtec.com/Pages/platstan.hmtl and http://www.sbsonline.com. Custom micropipettors that do not conform to this standard can also be utilized. In some systems, an electropipettor that is in fluid communication with a sample input channel is utilized. Micropipettors of this type are described, for example, in U.S. Pat. No. 6,150,180.

Inlets to the microfluidic devices disclosed herein can be holes or apertures that are punched, drilled or molded into the elastomeric matrix. Such apertures are sometimes referred to as "vias." The vias can also be formed using photoresist techniques. For example, metal etch blocking layers used in combination with patterning of photoresist masks and the use of solvents to remove etch blocking layers can be utilized to create vias. Vertical vias between channels in successive elastomer layers can be formed utilizing negative mask techniques. Vias can also be formed by ablation of elastomer material through application of an applied laser beam. All of these techniques are described in greater detail in U.S. application Ser. No. 09/605,520.

Inlets can optionally be lined with couplings (e.g., made of Teflon) to provide a seal with the pipette tips or syringe tip used to inject a solution.

As described further below, pumps formed from elastomeric materials can be used to transport solution through the flow channels. For channels of known dimensions, one can precisely regulate the volume introduced through an inlet from based upon the number of strokes of the pump.

Any sample or solution that is chemically compatible with the elastomeric material from which the microfluidic device is fabricated and which does not contain agents that are too large to pass through the flow channels can be introduced into the device. Examples of suitable samples include, but are not limited to, aqueous buffers or media containing cells, bacteria, viruses, phage, proteins, nucleic acids, small molecules, serum, whole blood or subfractions of blood, organic solvents containing dissolved solutes, oils and mixtures of organic and aqueous solvents.

D. Valves

1. Structure

The valves of the microfluidic devices provided herein are formed of elastomeric material and include a membrane or separating portion that separates a control channel and a flow channel. The valves have two general designs: those that are typically open and those that are normally closed. Valves that are typically open are actuated to block flow through a flow channel by applying pressure to the control channel, thereby deflecting the membrane into the flow channel to restrict flow. In the case of valves that are normally closed, the membrane or separating portion normally extends into the flow channel. However, upon reduction of pressure in the control channel relative to the flow channel, the membrane/separating portion is pulled into the control channel, thus removing the blockage in the flow channel.

Figure 2B:
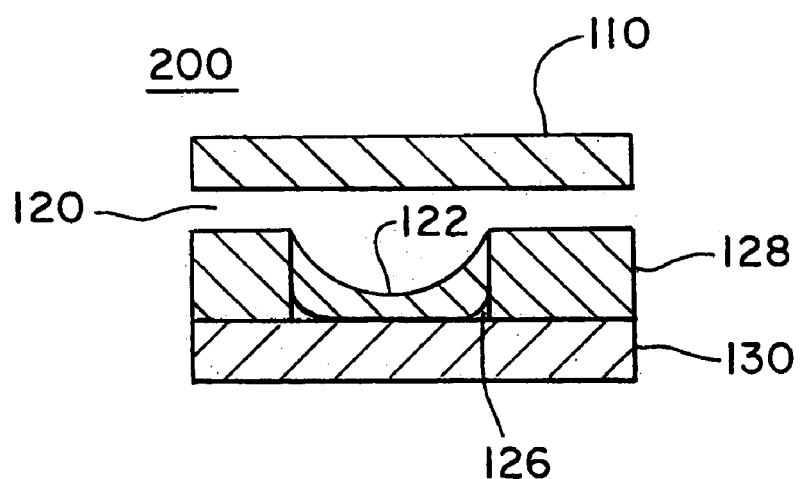
FIG. 2B is a sectional view of an elastomeric block showing blockage of a flow channel when a normally open valve is actuated.

FIGS. 1A and 1B illustrate the general elements of a valve that is typically open. As can be seen, elastomeric structure 24 contains a control channel 32 overlying recess 21 formed from a raised portion of a mold. When the recess in this elastomeric structure is sealed at its bottom surface to planar substrate 14 recess 21 forms a flow channel 30. As can be seen in FIG. 1B and FIG. 2A, flow channel 30 and control channel 32 are preferably disposed at an angle to one another with a small membrane 25 of elastomeric block 24 separating the top of flow channel 30 from the bottom of control channel 32. While these figures show control channels that extend across the device, it should be understood that this need not be the case. The control channel can be a recess sufficiently large such that the membrane is able to provide the desired level of blockage in the flow channel. FIG. 2B illustrates the situation for a normally open elastomeric valve structure 200 in which the valve has been actuated and the flow channel is blocked. In particular, the structure includes a control channel 120 formed within one elastomeric layer 110 that overlays another elastomeric layer 128 which includes a flow channel 126. Elastomeric layer 110 is attached to substrate 130. Because the control channel has been pressurized, the membrane 122 separating the control channel 120 and the flow channel 126 is deflected down into the flow channel 126, thereby effectively blocking solution flow therethrough. Once pressure is released, membrane—122 deflects back up from the flow channel 126 to allow solution flow.

In certain devices, planar substrate 14 is glass. The transparent properties of glass can be useful in that it allows for optical interrogation of elastomer channels and reservoirs. Alternatively, the elastomeric structure can be bonded onto a flat elastomer layer, thereby forming a permanent and high strength bond. This can prove advantageous when higher back pressures are generated. Hence, the choice of substrate upon which a flow channel is formed (e.g., glass or elastomer) depends in part on the type of detection utilized, as well as the structural requirements of the device.

While the valve shown in FIGS. 1B and 2 involve a system in which a control channel overlays a flow channel, different configurations can be utilized. For example, FIGS. 3A and 3B illustrate a side actuated valve. More specifically, FIG. 3A shows side actuated valve structure 4800 in an unactuated position. Flow channel 4802 is formed in elastomeric layer 4804. Control channel 4806 abutting flow channel 4802 is also formed in elastomeric layer 4804. Control channel 4806 is separated from flow channel 4802 by elastomeric membrane portion 4808. A second elastomeric layer (not shown) is bonded over bottom elastomeric layer 4804 to enclose flow channel 4802 and control channel 4806. FIG. 3B shows side actuated valve structure 4800 in an actuated position. In response to a build up of pressure within control channel 4806, membrane 4808 deforms into flow channel 4802, blocking flow channel 4802. Upon release of pressure within control channel 4806, membrane 4808 relaxes back into control channel 4806 and opens flow channel 4802.

As noted above, the valves can also have a normally closed configuration. FIG. 4A illustrates one example of a normally closed valve 4200 in an unactuated state. Flow channel 4202 and control channel 4204 are formed in elastomeric block 4206. Flow channel 4202 includes a first portion 4202a and a second portion 4202b separated by separating portion 4208. Control channel 4204 overlies separating portion 4208. As shown in FIG. 4A, in its relaxed, unactuated position, separating portion 4208 remains positioned between flow channel portions 4202a and 4202b, interrupting flow channel 4202. FIG. 4B shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force, membrane 4208 projects into control channel 4204, thereby removing the obstacle to solution flow through flow channel 4202 and creating a passageway 4203. Upon elevation of pressure within control channel 4204, separating portion 4208 assumes its natural position, relaxing back into and obstructing flow channel 4202.

It is not necessary that the elastomeric layers that contain the flow and control channels be made of the same type of elastomeric material. For example, the membrane that separates the control and flow channels can be manufactured from an elastomeric material that differs from that in the remainder of the structure. A design of this type can be useful because the thickness and elastic properties of the membrane play a key role in operation of the valve.

2. Options for Actuating Valves

A variety of approaches can be utilized to open or close a valve. If a valve is actuated by increasing pressure m a control channel, in general this can be accomplished by pressurizing the control channel with either a gas (e.g., air) or a fluid (e.g., water or hydraulic oils). However, optional electrostatic and magnetic actuation systems can also be utilized. Electrostatic actuation can be accomplished by forming oppositely charged electrodes.(which tend to attract one another when a voltage differential is applied to them) directly into the monolithic elastomeric structure. For example, referring once again to FIG. 2, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e., closing flow channel 30).

Alternatively, magnetic actuation of the flow channels can be achieved by fabricating the membrane separating the flow channels with a magnetically polarizable material such as iron, or a permanently magnetized material such as polarized NdFeB. Where the membrane is fabricated with a magnetically polarizable material, the membrane can be actuated by attraction in response to an applied magnetic field.

Optional electrolytic and electrokinetic actuation systems can also be utilized. For example, actuation pressure on the membrane can be generated from an electrolytic reaction in a recess overlying the membrane. In such an embodiment, electrodes present in the recess are used to apply a voltage across an electrolyte in the recess. This potential difference causes an electrochemical reaction at the electrodes and results in the generation of gas species, thereby giving rise to a pressure differential in the recess. Alternatively, actuation pressure on the membrane can arise from an electrokinetic fluid flow in the control channel. In such an embodiment, electrodes present at opposite ends of the control channel are used to apply a potential difference across an electrolyte present in the control channel. Migration of charged species in the electrolyte to the respective electrodes can give rise to a pressure differential.

Finally, valves can be actuated the device by causing a fluid flow in the control channel based upon the application of thermal energy, either by thermal expansion or by production of gas from liquid. Similarly, chemical reactions generating gaseous products may produce an increase in pressure sufficient for membrane actuation.

3. Options for Selectively Actuating Valves

In order to facilitate fabrication and to reduce the number of control channels in a microfluidic device, often a control channel overlays a number of flow channels. In such instances, pressurization of such a control channel could cause blockage of all the flow channels. Often it is desired to block only selected flow channels, rather than all the flow channels which a control channel abuts. Selective actuation can be achieved in a number of different ways.

Figure 5:
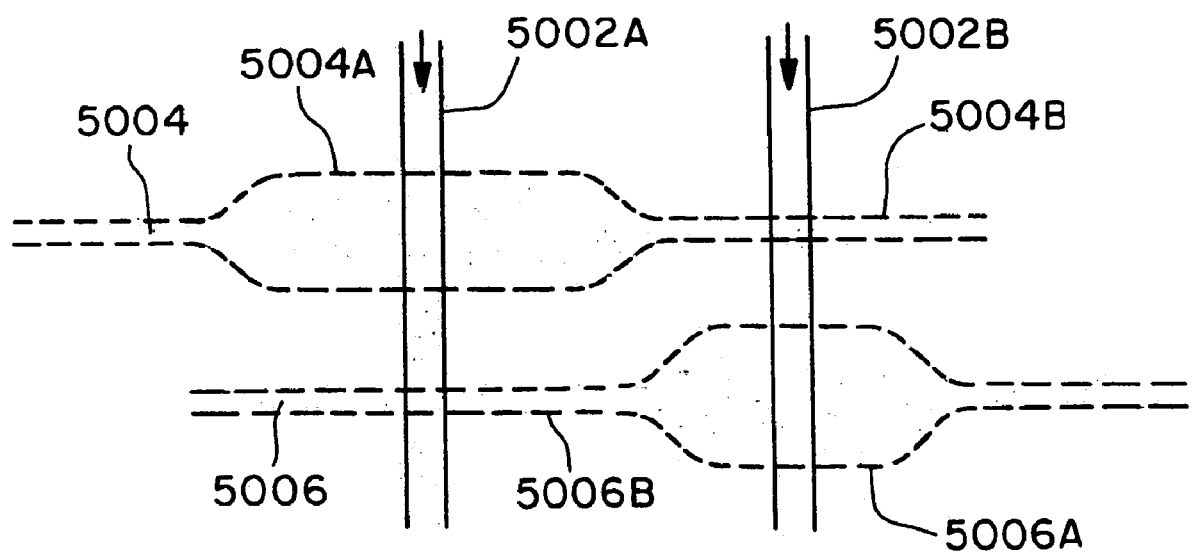
FIG. 5 illustrates one arrangement of control and flow channels that allow for selective blockage of certain flow channels.

One option illustrated in FIG. 5 is to control the width of the control channels 5004, 5006 at the point at which they extend across the flow channels 5002A and 5002B. In locations where the control channels are wide 5004A, 5006A, pressurization of the control channel 5004, 5006 causes the membrane separating the flow channel and the control channel to depress significantly into the flow channel 5002A, 5002B, thereby blocking the flow passage therethrough. Conversely, in the locations where the control line is narrow 5004B, 5006B, the membrane separating the channels is also narrow. Accordingly, the same degree, of pressurization will not result in membrane becoming depressed into the flow channel 5002A, 5002B. Therefore, fluid-passage thereunder will not be blocked.

The same general effect can be obtained by varying the width of the flow channel relative to the control channel. Incorporation of an elastomeric support in the section of the flow channel opposite the membrane that is deflected into the flow channel can also prevent complete stoppage of solution flow.

Valves in certain of the figures are represented by single dashed lines if the valve can be utilized to block solution flow through the flow channel. A control channel that crosses a flow channel but which does not act to block the flow channel (for the reasons just described) is represented by a solid arch that arches over a flow channel.

Various other methods of actuating valves are described in the above incorporated U.S. and PCT applications.

E. Pumps

Figure 6A:
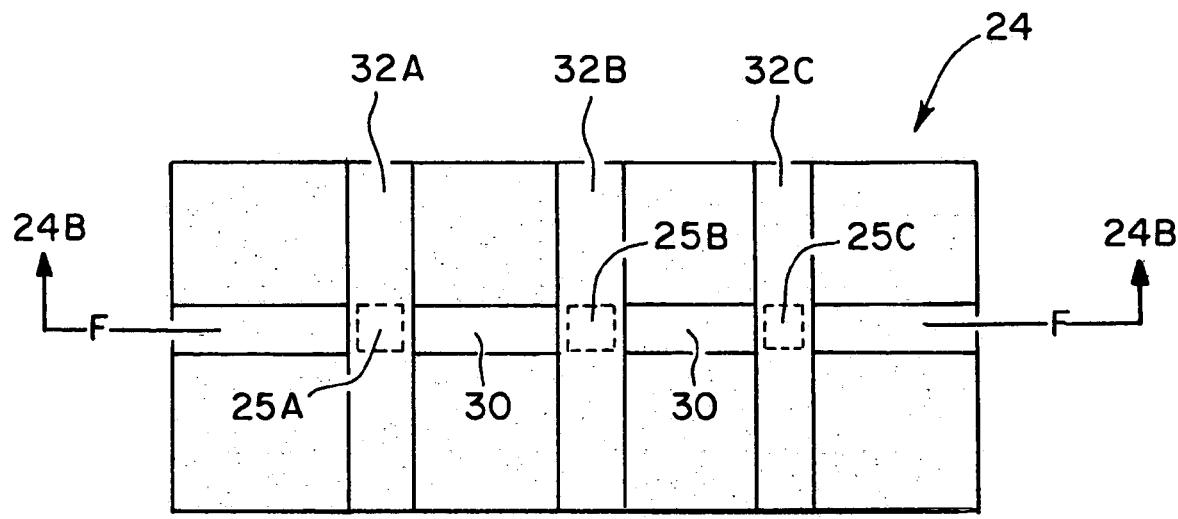
FIGS. 6A and 6B illustrate one example of a peristaltic pump.
Figure 6B:
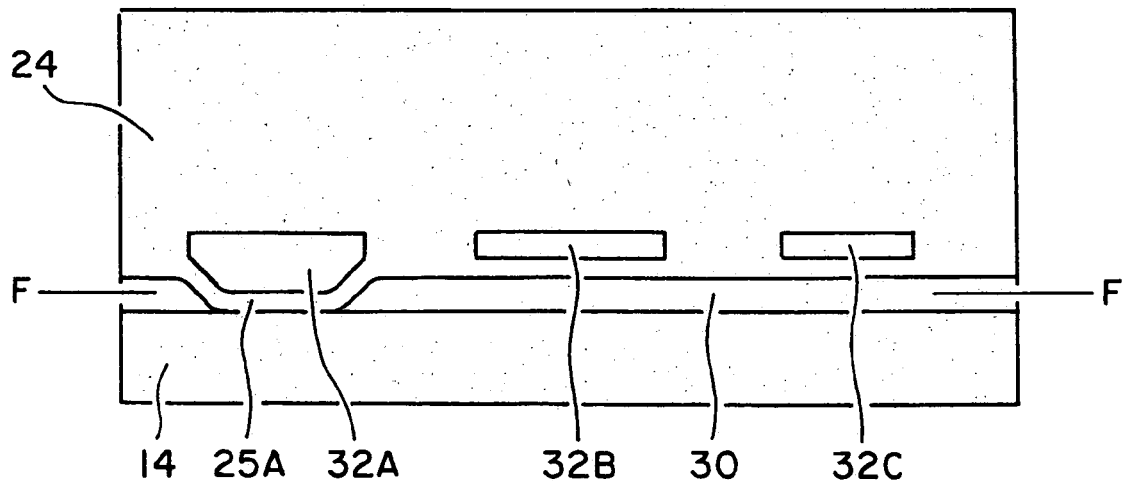

The pumps integrated within the microfluidic devices described herein can be formed from a plurality of control channels that overlay a flow channel. A specifier example of a system for peristaltic pumping is shown in FIGS. 6A and 6B. As can be seen, a flow channel 30 has a plurality of generally parallel control channels 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc. Each of control lines 32A, 32B, and 32C is separately addressable. Therefore, peristalsis can be actuated by the pattern of actuating 32A and 32C together, followed by 32A, followed by 32A and 32B together, followed by 32B, followed by 32B and C together, etc. Pumps of this type are denoted in shorthand form in certain of the figures with series of three parallel dashed lines.

External pumps can also be connected to a flow channel to transport solutions through a channel. Alternatively, a vacuum can be applied to a flow channel to direct fluid flow toward the region of reduced pressure.

F. Mixer Units

Figure 7A:
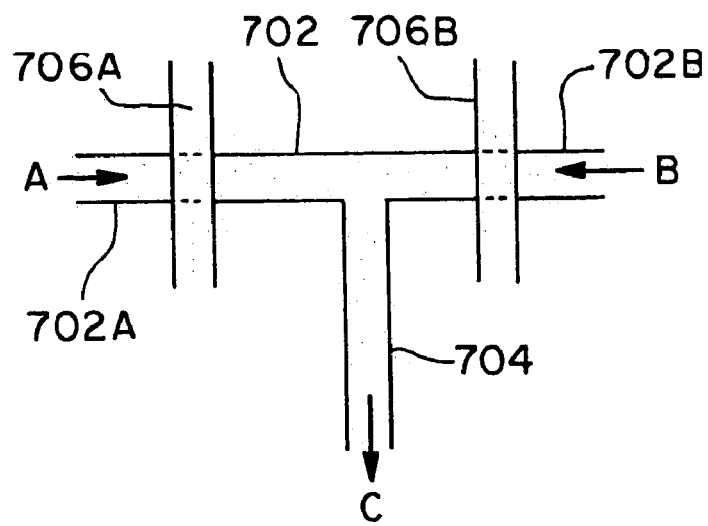
FIGS. 7A-7C are top schematic views of different configurations of flow channels that allow for mixing of solutions.
Figure 7B:
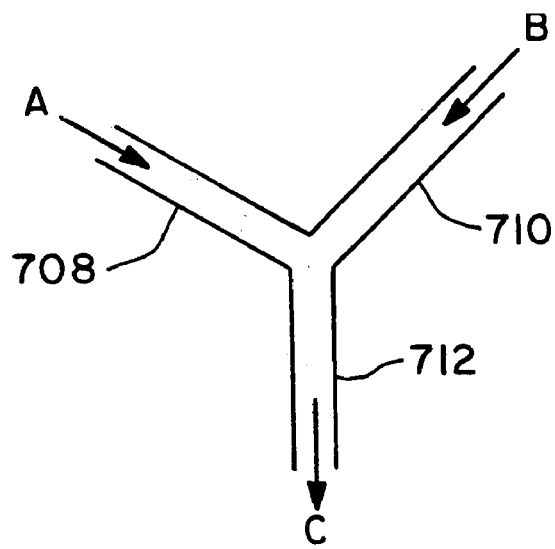

Units for mixing one or more fluids introduced the flow channels can be have a variety of different configurations. One simple way to rapidly mix fluids is simply to have two solutions flow into one another in a Y- or T-shaped junction. This is illustrated in FIG. 7A where solution A flows through section 702A of flow channel 702, with solution B flowing through section 702B. Optional control channels can overlay each section to control solution flow into the junction if desired. At the intersection of flow channel 702 with flow channel 704, solutions A and B are mixed to form solution C. Similarly, in the Y-shaped junction depicted in FIG. 7B, solution A flowing through branch channel 708 and solution B flowing through channel 710 converge at flow channel 712 to form solution C.

Figure 7C:
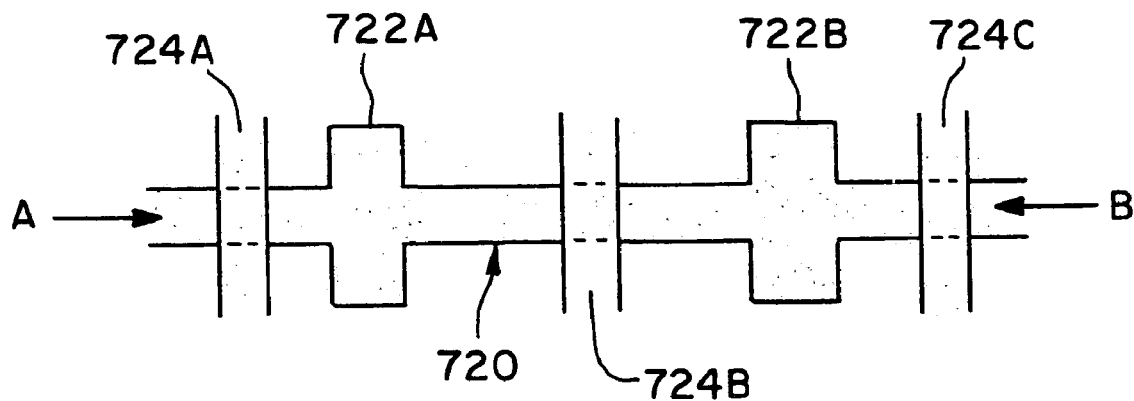

Another mixing option is to flow solutions repeatedly back and forth between two reservoirs or chambers. Such an arrangement is depicted in FIG. 7C where a flow channel 720 include two expanded regions 722A, 722B to form two reservoirs in which solution can collect. Control channels 724A, 724B, and 724C can be placed on either side of the reservoirs 722A, 722B to control fluid flow therebetween. Solution A can be introduced into reservoir 722A and solution B introduced into reservoir 722B. By opening valve 724B located between the two reservoirs 722A, 722B, the two solutions can be mixed. Mixing and incubation can continue as the solutions are moved back and forth between the two reservoirs 722A, 722B. One way this can be accomplished is to open valve 724A and then move solution from reservoir 722A into reservoir 722B. The direction of flow is then reversed by closing valve 724A, opening valve 724C, and then transporting solution from reservoir 722B back to reservoir 722B.

Figure 8:
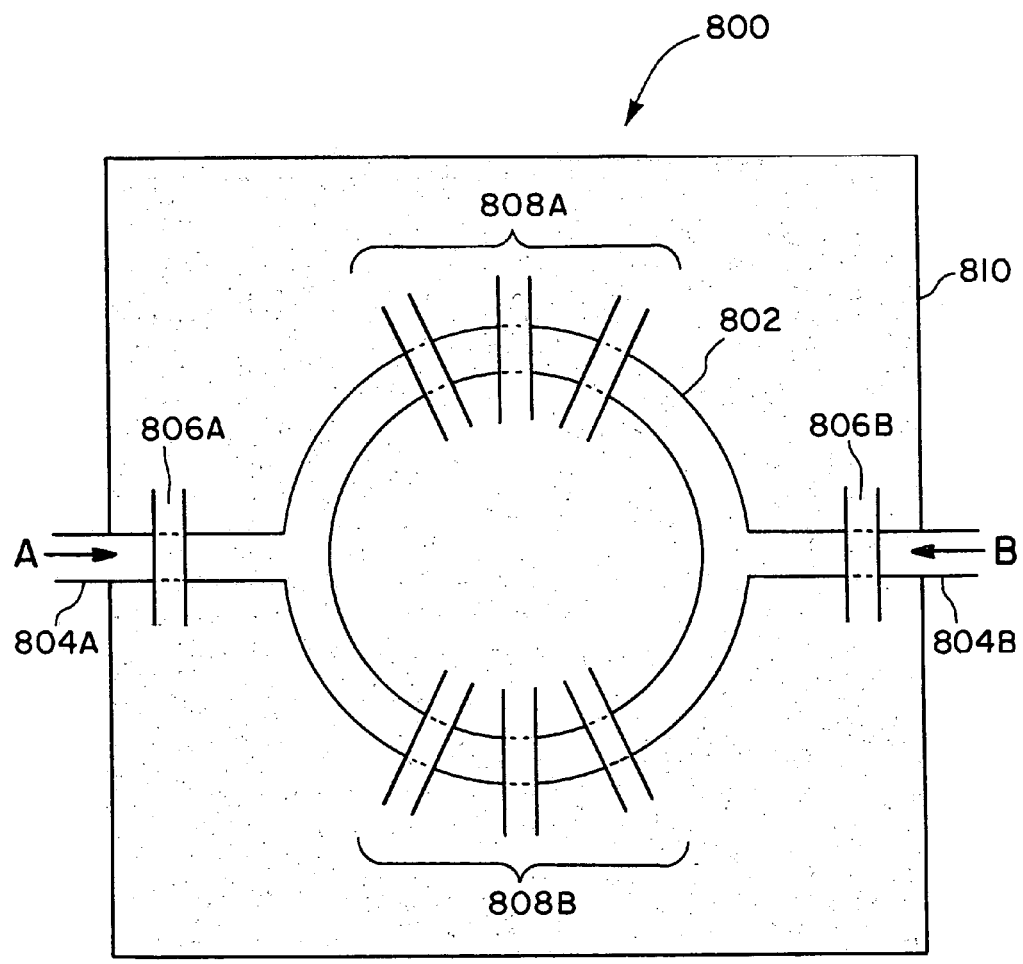
FIG. 8 is a top schematic view of an exemplary rotary pump.

A rotary pump can also be utilized to mix and incubate solutions. This system involves the use of one or more pumps to flow solution around a circular flow channel. FIG. 8 depicts one such pump 800. This particular rotary pump 800 includes a closed loop flow channel 802. Two inlet/outlet flow channels 804A, 804B are in fluid communication with the circular flow channel 802. Valves 806A, 806B are located within the inlet/outlet flow channels 804A, 804B to control fluid flow into and out of the circular flow channel 802. Pumps 808A, 808B of the design described supra (i.e., a plurality of control channels that overlay the flow channel) are located across from one another in the closed loop flow channel 802. The rotary pump 800 can be positioned adjacent a temperature control device 810 to regulate temperature of the mixture as it is pumped through the rotary pump.

In operation, valves 806A, 806B are both initially closed. Valve 806A is then opened to allow solution A to enter the circular flow channel 802. Valve 806A is then closed and valve 806B opened to allow solution B to enter the circular flow channel 802. Valve 804B is then also closed and solutions A and B mixed and incubated by circulating the mixture under the action of pumps 808A, 808B. After the solutions have been mixed and incubated for the desired length of time, either of (or both) valves 806A, 806B are opened and the mixture withdrawn from the circular flow channel 802.

Although the particular pump FIG. 8 utilizes a circular flow channel, the actual shape of the flow channel can be essentially any shape so long as the loop is a closed loop. Thus, the flow channel can be circular, oblong, or serpentine in shape. Furthermore, the order and timing of solution introduction into the loop can also be varied.

G. Detection Units

1. General

The microfluidic devices provided can be utilized in combination with a wide variety of detection methodologies. Detection can involve the detection of particular events and/or particular entities such as particles, beads and cells. Detection can be accomplished using detection methodologies in use in flow cytometry and liquid chromatography. Examples of particular detection methods useful with the present microfluidic devices include, but are not limited to, light scattering, multichannel fluorescence detection, UV and visible wavelength absorption, luminescence, differential reflectivity, and confocal laser scanning. Applications can also utilize scintillation proximity assay techniques, radiochemical detection, fluorescence polarization, fluorescence correlation spectroscopy (FCS), time resolved energy transfer (TRET), fluorescence resonance energy transfer (FRET) and variations such as bioluminescence resonance energy transfer (BRET). Additional detection options include electrical resistance, resistivity, impedance, and voltage sensing.

Alternatively, fluids can be transported directly to a mass spectrometer interface (e.g., electrospray ionization, ESI) or directed onto a matrix of flow interface for analysis by Matrix-Assisted Laser Desorption Ionization Time of Flight Mass Spectrometry (MALDI-TOF). Detection and measurement based on these methodologies can be used to sort cells or direct cells, beads or, particles into new locations on or off the microfluidic device.

The term "detection section," "detection region," and other like terms refer to the portion of the microfluidic device at which detection occurs. In general, the detection section can be at essentially any point along one of the flow channels or at an intersection of flow channels. The detection region is in communication with one or more microscopes, diodes, light stimulating devices (e.g., lasers), photomultiplier tubes, processors and combinations of the foregoing, which cooperate to detect a signal associated with a particular event or agent. In some instances, the detection section is coincident with a holding space; in other instances the detection section includes a rotary pump, while in still other instances, the detection section is located adjacent to a rotary pump or holding space, with detection occurring following complete mixing of solutions in the mixer or release of solution from the holding space.

Often the signal being detected is an optical signal that is detected in the detection section by an optical detector. The optical detector can include one or more photodiodes (e.g., avalanche photodiodes), a fiber optic light guide leading, for example, to a photomultiplier tube, a microscope, and/or a video camera (e.g., a CCD camera).

The optical detector can be microfabricated within the microfluidic device, or can be a separate element. If the optical detector exists as a separate element and the microfluidic device includes a plurality of detection sections, detection can occur within a single detection section at any given moment. In other instances, an automated system is utilized which scans the light source relative to the microfluidic device, scans the emitted light over a detector, or includes a multichannel detector. For example, the microfluidic device can be attached to a translatable stage and scanned under a microscope objective. The acquired signal is routed to a processor for signal interpretation and processing. Arrays of photomultiplier tubes can also be utilized. Additionally, optical systems that have the capability of collecting signals from all the different detection sections simultaneously while determining the signal from each section can be utilized.

In some instances, the detection section includes a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections, or laser diodes can be microfabricated into the microfluidic device itself. Alternatively, laser diodes can be fabricated into another device that is placed adjacent to the microfluidic device being utilized to conduct an assay such that the laser light from the diode is directed into the detection section.

In some instances in which external radiation and/or detector are utilized, an substrate optically transparent at the wavelength being monitored is used to cover the detection section. However, by appropriate selection of elastomeric materials, monolithic elastomeric devices can still be utilized in conjunction with a wide variety of external optical detection methods.

Detection can involve a number of non optical approaches as well. For example, the detector can also include, for example, a temperature sensor, a conductivity sensor, a potentiometric sensor (e.g., pH electrode) and/or an amperometric sensor (e.g.,to monitor oxidation and reduction reactions).

In certain methods, solutions are transported from the microfluidic device to a separate external device for further analysis. The external device can be any of a number of analytical devices such as UV/VIS, IR, NMR and/or ESR spectrometers; chromatographic columns (e.g., HPLC); and/or mass spectrometry, for example.

2. Optical Microscope

Certain methods utilize an optical microscope to examine the different detection sections in the different flow channels. The objective lens of the microscope is directed towards the detection section. Typically, a mercury arc lamp or argon laser is utilized as the light source. The microfluidic device can be mounted on a translation stage such that the various detection sections can be positioned by translation over the objective lens. Additional details regarding the use of microscopes with microfluidic devices similar to those described herein are provided in PCT publication WO 99/61888.

3. Fluorescent Detection Systems

Detection methodologies that can be utilized in the screening process include, and are not limited to: (1) fluorescence intensity, (2) fluorescence polarization, (3) fluorescence resonance energy transfer (FRET), (4) heterogeneous time resolved fluorescence (HTRF) or time resolved energy transfer (TRET) (5) Fluorescence correlation spectroscopy (FCS) and related techniques (such as fluorescence intensity distribution analysis (FIDA). (see, e.g., Pope et al. (1999) Drug Discovery Today 4:350-362; Kask et al. (1999) Proc. Natl. Acad. Sci. USA 96:13756-61, Moore et al.(1999) J. Biomol. Screening 4:335-353; and Auer et al. (1999) Drug Discovery Today 3:457-465). A more detailed discussion of these detection options follows.

Fluorescence intensity: Measurement of the intensity of fluorescence of a sample provides a direct measurement of fluorophore concentration. This technique is often used in enzyme assays, where an enzyme activity is measured using a non-fluorescent substrate that is converted to a fluorescent product by the action of the enzyme (i.e., a fluorogenic substrate). Other assays that measure fluorescence directly include calcium binding assays, in which the fluorescence of the calcium binding dye is significantly increased upon binding calcium. Thus, the detector in certain systems is an instrument able to detect fluorescence intensity from the detection section of the microfluidic device.

Fluorescence polarization: Fluorescence polarization (FP) is another common detection technique that can be utilized with the microfluidic devices provided herein. The theory of FP is that when a fluorophore is excited with polarized light, the emitted light is also polarized. This occurs because excitation is dependent upon thee orientation of the fluorophore dipole to the excitation beam. The emitted light is depolarized upon rotational diffusion of the fluorophore. For a small molecule fluorophore, this occurs rapidly and the emitted light is isotropic. Changes in the rotational diffusion time of a small fluorophore occur when it becomes bound to a much larger molecule and lead to measurable anistropy in the emitted light. Thus, FP can be utilized in a wide variety of assays in which in certain circumstances a fluorescently labeled agent is part of a large molecule that tumbles relatively slowly, whereas in other circumstances the labeled agent is free in solution and able to tumble more rapidly. Examples of such assays include assays involving binding, of a labeled ligand to a cell surface receptor, ligand/antiligand binding (e.g., ligand/receptor binding) and a labeled protein substrate and a labeled cleavage product.

Fluorescence polarization is determined by measuring the vertical and horizontal components of fluorophore emission followings excitation with plane polarized light. Light from a monochromatic source (at an appropriate excitation wavelength) passes through a vertical polarizing filter to excite fluorescent molecules in the sample. Only those molecules that are orientated in the vertically polarized plane absorb light, become excited, and subsequently both emit light. The emission light intensity is measured both parallel and perpendicular to the exciting light. The fraction of the original incident vertical lights intensity that is emitted in the horizontal plane is a measure of the amount of rotation the fluorescently labeled molecule has undergone during the excited state and therefore is a measure of its relative size. Thus, the detector used to monitor FP in the microfluidic device includes the elements necessary to make the foregoing measurements (see FIG. 9 and discussion infra). A number of commercially available FP instruments can be used in conjunction with the present microfluidic devices (e.g., systems from Panvera Corp). Additional guidance regarding FP detection is provided, for example, by Chen et al. (1999) Genome Research 9:492-8; and in U.S. Pat. No. 5,593,867 to Walker, et al.

Fluorescence resonance energy transfer (FRET): This technique is dependent upon non-radiative transfer between two fluorophores (a donor and an acceptor) that occurs when they come into close proximity (<5 nm). The efficiency of transfer highly dependent upon the distance between the fluorophores, their physical properties and the spectral overlap between them. Under FRET conditions, excitation at the donor excitation maximum is efficiently transferred to the acceptor and emitted at the acceptor emission wavelength. This property can be exploited in many different types of assays that can either bring fluorophores together (increased FRET). or separate them (decreased FRET). Thus, FRET assays can be conducted by detecting an increase in the fluorescence intensity of the acceptor and a decrease in fluorescence intensity of the acceptor. Alternatively changes in the ratio of emission at the donor emission maximum to emission at the acceptor maximum can be used to follow increases or decreases in FRET. The present microfluidic devices can be utilized in FRET assays in conjunction with commercially available fluorescent readers. These systems include a source to activate the acceptor fluorophore and then detect alterations in the emissions from the donor and/or acceptor fluorophore.

A number of fluorophores suitable for conducting FRET assays are known. Specific examples include, 6-carboxy fluorescein (FAM), 5&6-carboxyrhodamine-110 (R110), 6-carboxyrhodamine-6G (R6G), N,N,N',N'-tetramethyl - 6-carboxyrhodamine (TAMRA), 6-carboxy-X-rhodamine (ROX), 6-carboxy-4',5'-dichloro-2',7'-dimethoxyfluorescein (JOE), ALEXA-Fluor™. Cy2, Texas Red and Rhodamine Red. Additional fluorescent dyes available from Applied Biosystems Division of Perkin Elmer Corporation (Foster City, Calif.) include, 6-carboxy-2',4,7,7'-tetrachlorofluorescein (TET), 6-carboxy-2',4,4',5',7,7'-hexachlorofluorescein (HEX), 5-carboxy-2',4',5',7'-tetrachlorofluorescein (ZOE), NAN, NED; fluorophores available from Amersham Pharmacia Biotech (Piscataway, N.J.) include, Cy3, Cy3.5, Cy5, Cy5.5, Cy7, and Cy7.5.

Further guidance regarding the selection of donor and acceptor pairs that can effectively be used in FRET-based assays include: Fluorescence Spectroscopy (Pesce et al., Eds.) Marcel Dekker, N.Y., (1971); White et al., Fluorescence Analysis: A Practical Approach, Marcel Dekker, N.Y., (1970); Berlman, Handbook of Fluorescence Spectra of Aromatic Molecules, 2nd ed., Academic Press, N.Y., (1971); Griffiths, Colour and Constitution of Organic Molecules, Academic Press, N.Y., (1976); Indicators (Bishop, Ed.). Pergamon Press, Oxford, 19723; and Haugland, Handbook of Fluorescent Probes and Research Chemicals, Molecular Probes, Eugene (1992).

Another option is to use various fluorescent proteins. Examples include green fluorescent protein (GFP), blue fluorescent protein (BFP), yellow fluorescent protein and ds Red (a red fluorescent protein).

Time-resolved techniques: A variety of time-resolved fluorescent techniques can be utilized. One such technique is heterogeneous time-resolved fluorescence (HTRF) or time resolved energy transfer (TRET). This method uses fluorescence resonance energy transfer between two fluorophores. The most commonly used donor is europium cryptate (EuK), which absorbs light at 337 nm and emits at 620 nm. Other commonly used long-lived donors are lanthanates ($Ln^{3+}$). EuK can transmit this energy in a non-radiative fashion to an appropriate acceptor, such as XL665 (a modified allophycocyanin) when the acceptor-donor pair are in close proximity (<5-10 nm). When excited at 620 nm, XL665 emits light with a slow decay at 665 nm. Detection is performed after a delay (usually ~50 μs) as the measured ratio of fluorescence at 665 nm to fluorescence at 620 nm ($F_{665}/F_{620}$). The advantage of using an acceptor-donor pair with long lifetimes is that background fluorescence decays more rapidly than the desired signal, and consequently HTRF is extremely sensitive.

Fluorescence correlation spectroscopy (FCS): This method is based upon the recognition that as a fluorescently labeled molecule passes through a confocal laser beam and is excited, it emits photons of fluorescent light. The length of each photon burst is dependent upon the time spent in the confocal beam, and is diffusion controlled. By measuring the time associated with each burst, diffusion coefficients can be calculated, allowing discrimination of fluorescent molecules, such as bound and free species in a solution. Quantitation of free and bound ligand therefore allows determination of absolute concentrations of fluorophores and degree of binding. FCS is insensitive to miniaturization and therefore useful for implementation in microfluidic devices. When utilized with the present devices, a confocal laser is oriented such that the beam it emits is directed towards the detection section. The fluorescent detector is positioned to receive the photons of emitted light received from the detection section.

Ligands in Detection Section: Certain detection methods involve immobilizing an antiligand within the detection section. In this way, ligands that specifically bind to the antiligand can be captured and detected within the detection section. Often the antiligand is an immunological agent such as an antibody. The use of this mode of detection is described in further detail infra.

4. Single Molecule and Single Cell Measurements

Certain detection units that can be utilized with the systems described herein permit the detection and measurement of single molecules or cells. This capability can enable one to study processes that might not be apparent when making measurements of ensemble averages of populations of molecules or cells. In particular, such measurements allow observation of subpopulations of events within apparently homogeneous systems, and the analysis of dynamic events occurring on different time scales that would be lost upon averaging (see, e.g., Ishii, Y. and Yanagida, T. (2000) Single Mol. 1:5-16 and Weiss S. (1999) Science 283:676-1683. Fluorescence Correlation Spectroscopy (FCS; described supra) is one example of an intrinsically single molecule detection technique in which such detection units are useful. However, with standard optics, one can readily detect events at the single molecule or single cell level in essentially all of the modes described above (fluorescence intensity, fluorescence polarization, fluorescence resonance energy transfer (FRET), and fluorescence correlation spectroscopy (FCS)). Optical systems for the detection of single DNA molecules and cells in microfluidic devices are described in PCT Publication WO 99/61888, which is incorporated by reference in their entirety for all purposes.

Figure 9:
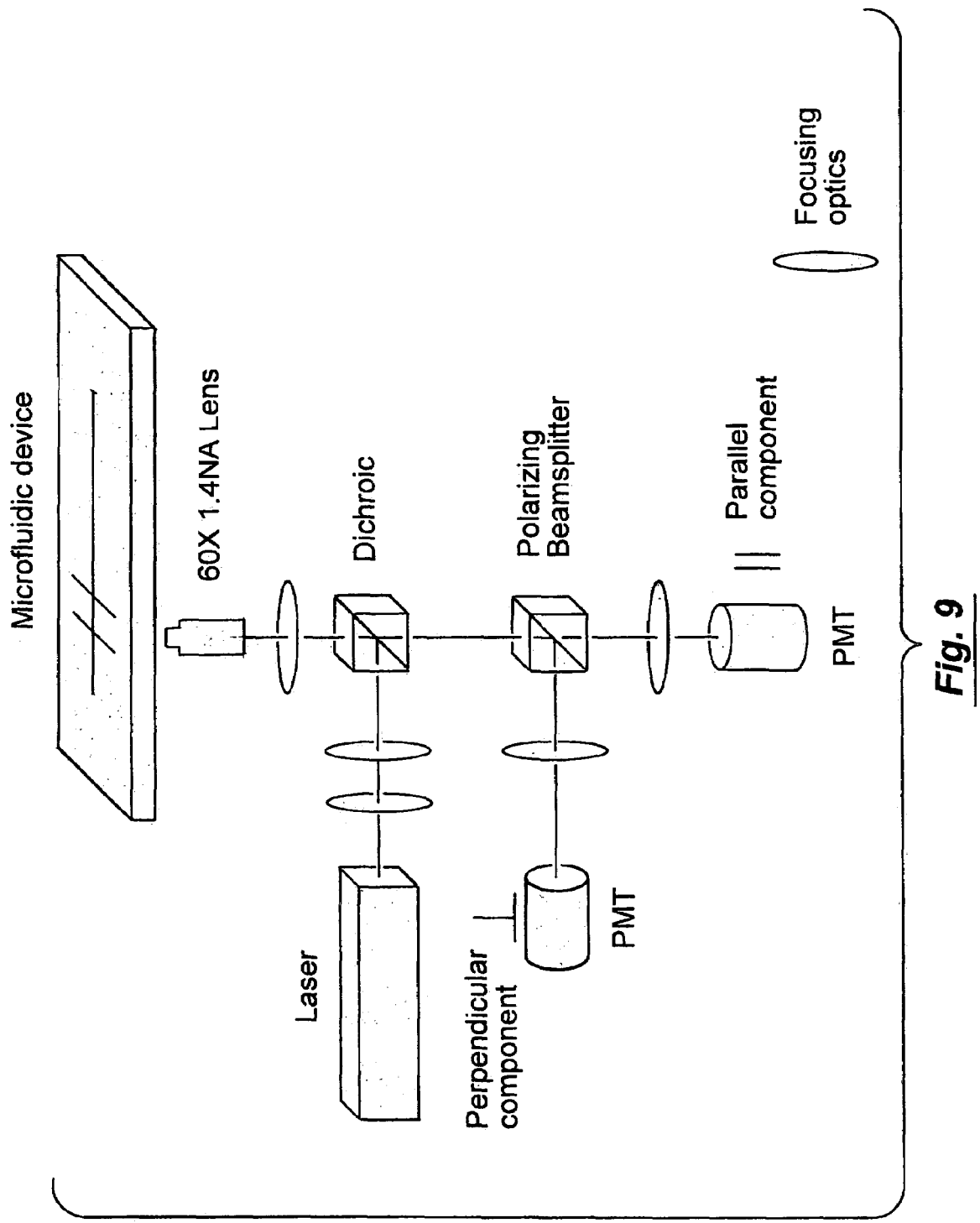
FIG. 9 depicts an exemplary optical system for conducting single molecule or single cell measurements.

The optical arrangement discussed in these publications can be modified to determine multiple signals from a detection section. For instance, using commercially available components (such as described at http://www.newport.com; 2001 Catalog), polarization optics can be utilized to prepare a device in which relative polarized signal strength is determined. One example of such a system is illustrated in FIG. 9. As shown, the optical system includes a laser that generates a laser beam that is directed towards the detection section of the microfluidic device by a dichroic mirror. Light emission from species (e.g., fluorescently labeled compounds) within the detection section are collected by a lens positioned adjacent to the detection section. The collected light passes through the dichroic mirror and is then split by a polarizing beam splitter cube into a plurality of light beams. The split polarized light is focused with focusing optics and the resulting signals are detected with a plurality of detectors, the system including one detector for each polarization component separated by the polarizing beamsplitter. With an arrangement such as this, one can measure signal intensity for different components of polarized light. Thus, in a fluorescence polarization experiment, for example, one can utilize such an arrangement to distinguish between an unbound molecule and the same type of molecule bound to a large species such as a cell. Because an unbound small molecule can tumble rapidly in solution, it emits non-polarized light. However, if the molecule becomes bound to the large species, the rate of tumbling slows dramatically and results in the emission of polarized light. One can detect a species that inhibits binding by contacting the complex with the test species and then determining whether there is a decrease in the emission of polarized light.

Various modifications of the optical system shown in FIG. 9 can be utilized. For instance, a polarized rotator (½ wave plate; see NewPort catalog) positioned in the excitation beam prior to the dichroic mirror, allows for variation of the polarization of the excitation light for purposes of measurement optimization. In another arrangement, a second PMT detector and appropriate dichroic mirrors and filters are positioned so as to detect the ratio of coupled (FRET) or uncoupled emissions at different wavelengths (see, e.g., Weiss S. (1999) Science,283:1676-1683).

III. High Throuput Screening Systems

A. General

As indicated supra, the foregoing elements or modules can be combined in a large number of configurations and utilized in a wide variety of applications. Exemplary designs useful for conducting certain types of assays are described in this section. It should be understood, however, that the microfluidic devices of the present invention are not limited to these particular configurations.

In general, the high throughput screening devices typically include a plurality of branch flow channels that intersect with, and are in fluid communication with, a main flow channel. The devices are designed such that common assay components (i.e., components utilized in each assay in the various branch flow channels such as cells, enzyme cofactors and buffers) are introduced into the main flow channel while blocking flow through the various branch flow channels. Once the common assay components have been introduced into the main flow channel, flow through the main flow channel is blocked. Different test agents or samples are subsequently introduced into the different branch flow channels, typically such that different test agents are introduced into different branch flow channels. Signal detection occurs within a detection region.

The microfluidic device can optionally include a holding space (e.g., a pen or cage). With such devices, one can initially introduce different samples into the branch flow channels and store a portion of the sample in the branch flow channels in the holding space. Assay components common to each assay are then introduced into the main flow channel. Retained solution in the branch flow channels is subsequently reacted with the assay components in the main flow channel. Typically, this is done by transporting retained solution back to the main flow channel for reaction with assay components therein.

Regardless of the particular design, a large number of test agents can be rapidly screened within a short time period because separate reactions can simultaneously be conducted in each of the flow channels.

Each branch flow channel can also optionally includes a mixer and/or a pump. The mixer can be used to mix and circulate solutions, typically after all the various solutions have been combined. The pumps are utilized for transporting fluids within the branch flow channel. The mixer and pump typically are elastomeric structures of the designs set forth supra.

B. Exemplary Devices

1. Configuration with a Single Main Flow Channel

Figure 12:
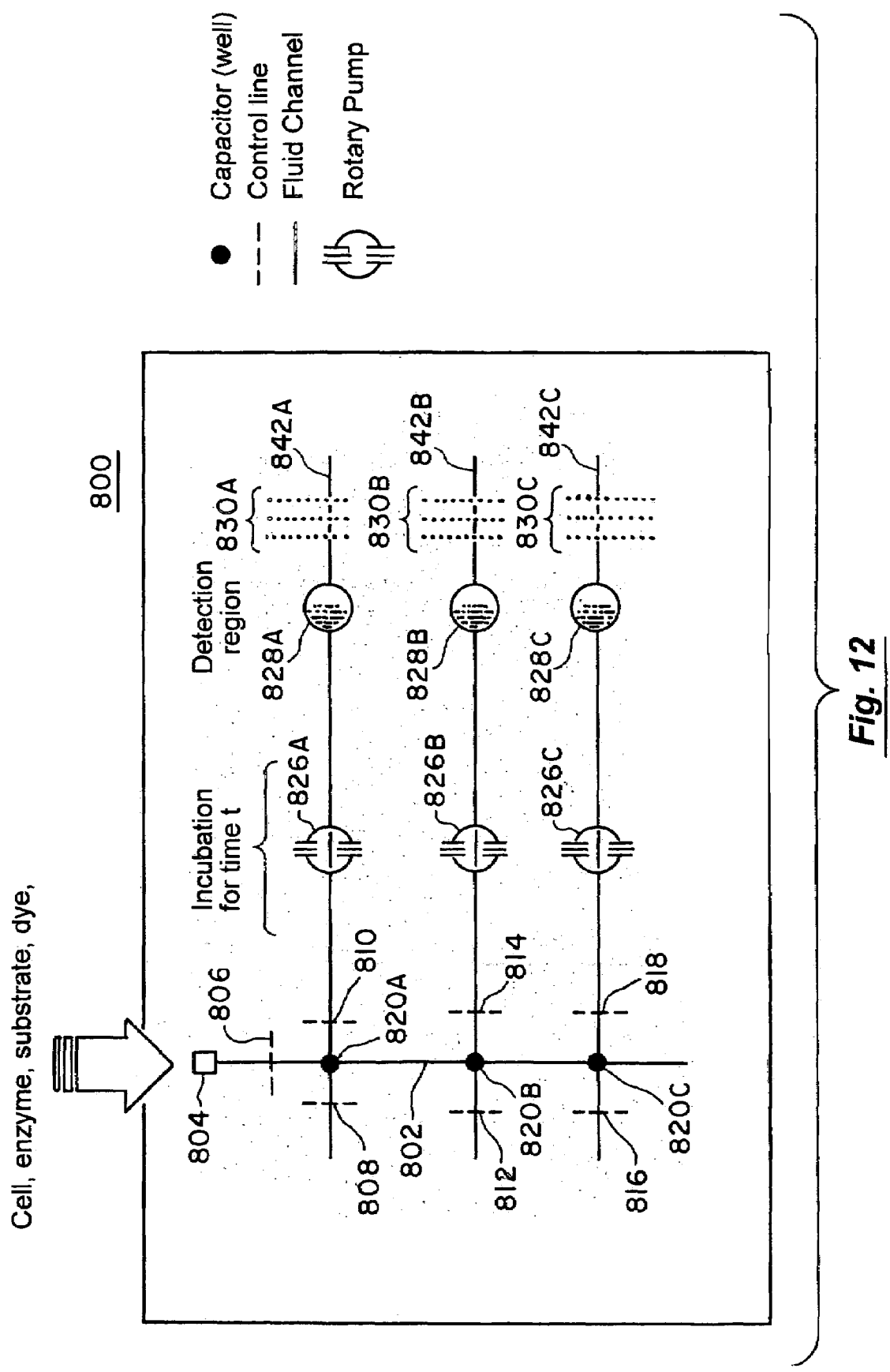
FIG. 12 depicts an exemplary microfluidic device useful for conducting high throughput screening assays among other types of assays.

A specific example of a microfluidic device that can be utilized in such high throughput screens is illustrated in FIG. 12. The device 800 includes a main flow channel 802 that is in fluid communication with a plurality of branch flow channels 842A, 842B, 842C. Each of the branch flow channels 842A, 842B, 842C intersect with the main flow channel 802 at a chamber (also called a capacitor or well) 820A, 820B, 820C that is sized to receive and store solution flowing within the main flow channel 802 and the branch flow channels 842A, 842B, 842C. The chambers 820A, 820B, 820C can include a depression formed into the elastomeric substrate into which the channels are formed. Other chambers consist of an expanded region of a flow channel. Each branch flow channel includes an optional mixer unit 826A, 826B, 826C, a detection region 828A, 828B, 828C and a pump 830A, 830B, 830C. Typically, the detection section 828A, 828B, 828C is located between the mixer unit 826A-C and pump 830A-C. In this way the pumps 830A-C can pull solution through the branch flow channel into the mixer unit 826A-C where solutions can be mixed and/or incubated and then, at the appropriate time, transported to the detection section 828A-C. The mixer unit 826A-C and pump 830A-C can be of the structure of described supra. The detection region 828A-C can be a section of the branch flow channel 842A-C that a detector is oriented to monitor. If an optical detector is utilized, then this section can include a material that is substantially optically transparent at the wavelength being monitored. The detection section 828A-C can also optionally include a holding space such as a pen or cage to retain a volume of solution that may also include cells or various supports (e.g., beads or particles).

In operation, to introduce assay components common to all the different assays, valve 806 is opened and assay solution introduced into the main flow channel 802 via inlet 804. Valves 810, 814, 818 in the branch flow channels typically are closed to block solution flow therethrough. Assay solution accumulates in the chambers 820A, 820B, 820C located along the main flow channel 802. An optional pump (not shown) located downstream of the last branch flow channel can be utilized to control the rate of solution flow through the main flow channel 802. Agents to be screened are introduced by closing valve 806 in the main flow channel 802 to restrict solution flow through the main flow channel while opening the branch flow channel valves 808, 812, 816.

Test agents or samples introduced into the branch flow channels 842A-C initially collect in the chambers 820A-C. Mixtures can be incubated/stored in the chambers 820A-C. Alternatively, valves 810, 814, 818 in the branch flow channels 842A-C are opened and mixtures from the chambers 820A-C withdrawn into the respective branch flow channels under the action of pumps 830A-C. Mixtures can be introduced into the mixing units 826A-C to allow further mixing and/or incubation. The resulting mixture is then pumped in a downstream direction towards the detection regions 828A-C where the solution can be assayed by an appropriate detector (not shown). Assays can be discrete, single time point (endpoint) assays, or involve sampling the mixture from the chamber or mixing units at various time periods (kinetic assays). In some assays pumps and branch flow valves are operated such that components can be moved back and forth within, a branch flow channel (e.g., between a holding space or mixer and the chambers), thereby promoting sequestration and mixing at the desired time.

As indicated supra, another option is to initially introduce the different test agents into the branch flow channels 842A-C. A portion of the solution containing the test agent is retained in the branch flow channels in a holding region located within the detection regions 828A-C. Common assay agents can then be introduced into the main flow channel 802 to introduce assay components into chambers 820A-C. Retained test agents in each of the branch flow channels 842A-C can then be flowed back to the chambers 820A-C to be mixed with the assay components. The resulting mixtures in the chambers 820A-C are then transported under action of the pumps 842A-C to their respective detection sections 828A-C for signal detection by a detector.

2. Configuration with Multiple Main Flow Channels

Figure 13:
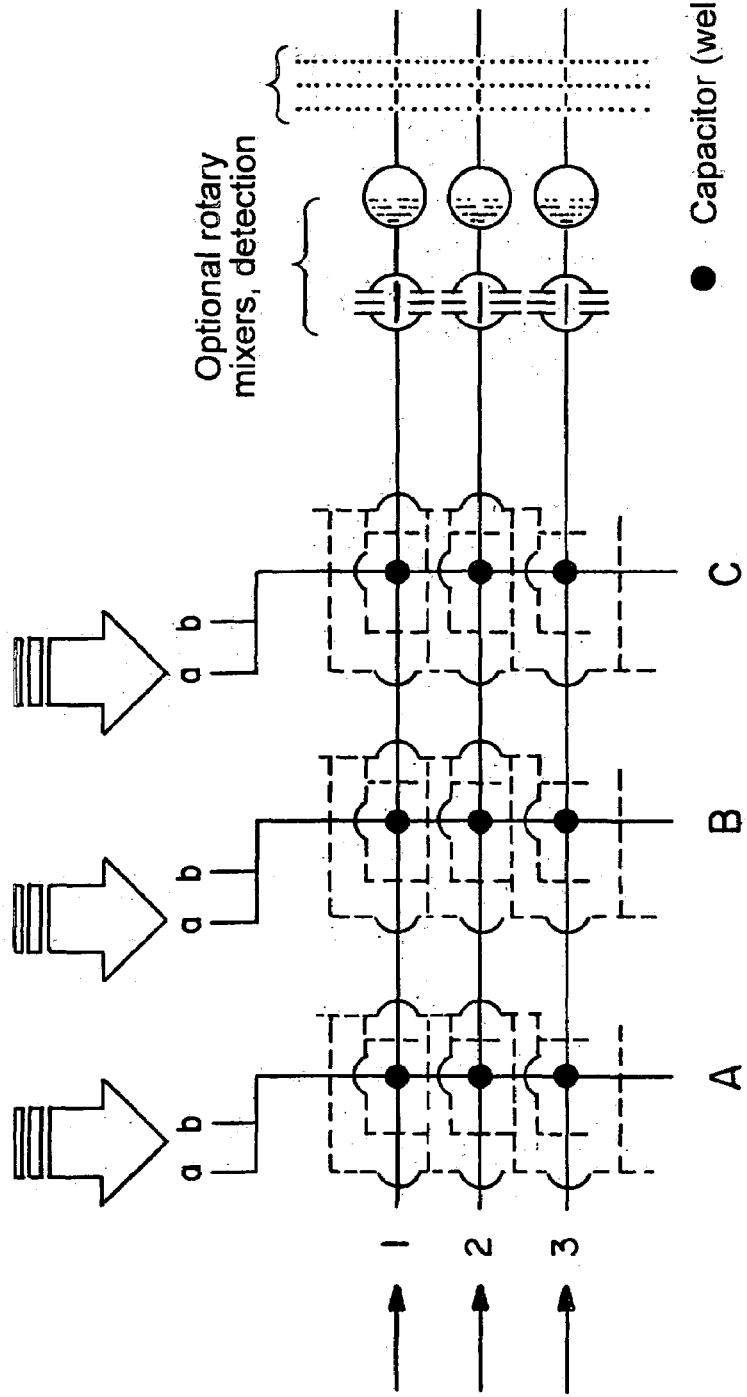
FIG. 13 depicts another exemplary microfluidic device useful for conducting high throughput screening assays among other types of assays.

Another specific example of a system that can be used, for example, in high throughput screening applications is illustrated in FIG. 13. As can be seen, this particular configuration is similar to the configuration just described and illustrated in FIG. 12, but differs in that it includes a plurality of main flow channels, indicated in FIG. 13 as A, B and C. Although this particular figure shows only three main flow channels (A, B, and C), it should be understood that related configurations including additional flow channels can also be utilized and are included in the present invention. Likewise, it should also be recognized that additional branch flow channels (indicated in FIG. 13 as 1, 2, 3) can be included. The inlet to each of the main flow channels, can include multiple injection ports, indicated in FIG. 13 as port (a) and (b). Of course additional ports could be include at each inlet.

In other respects, however, the configuration is similar to that shown in FIG. 12. For example, the device typically includes chambers at each intersection between a main flow channel (A, B, C) and branch channel (1, 2, 3). Additionally, each branch flow channel (1, 2, 3) can include an optional rotary mixer, detection region, and/or a pump. Detection can occur at each chamber and/or downstream of the main flow channels at a detection region separate from the chambers.

One situation in which the particular configuration depicted in FIG. 13 is useful is when a number of different assay components are to be added. In such situations, the multiple main flow channels can be utilized to separately introduce different assay components. This can be particularly useful when certain assay components need to be incubated before mixing with another assay component. For example, in a screen to identify compounds that inhibit the interaction between a protein and a ligand, cells expressing the receptor of interest can be introduced in main flow channel A such that cells are deposited in the different chambers along flow channel A. Different potential inhibitors can then be introduced into the different branch flow channels (1, 2, 3) and allowed to contact the cells in the respective chamber in the branch flow channel. The potential inhibitors and cells are then allowed to incubate to allow for the potential inhibitor to bind to the receptor. Subsequently, a known ligand for the receptor can be introduced into main flow channel B and into the chambers along flow channel B. The cell/potential inhibitor mixtures are then transported through the various branch flow channels into their respective chambers that include the known receptor ligand. After allowing a suitable time for binding between ligand and receptor, ligand/receptor binding is detected within the detection section to identify which, if any, of the potential inhibitors in fact prevent the ligand from binding to the receptor.

Another example of the usefulness of this configuration is when cells are contacted with a test agent in the chambers along main flow channel A and a wash cycle is needed before addition of other assay components. This can be facilitated by simply introducing the wash solution into main flow channel B and transporting the mixture in main flow channel A to the chambers in main flow channel B where washing occurs.

This configuration can also be arranged such that detection occurs at each of the chambers as assay solutions are transported along the branch flow channels (A, B, C). This can be useful to establish a baseline signal in upstream chambers before the final signal is detected at downstream chambers.

C. Test Compounds

The assay and screening methods described herein can be conducted with essentially any compound. In general terms, the test agent or test compound is potentially, capable of interacting with the component being assayed (e.g., cell, enzyme, receptor, antibody, cellular organelle). In cellular assays, for example, the component of the cell with which the test compound potentially interacts can be any molecule, macromolecule, organelle or combination of the foregoing that is located on the surface of the cell or located within the cell. For example, if one is screening for compounds capable of interacting with certain cellular receptors, the test agents are selected as potentially able to interact with the receptors of interest (e.g., binding at the binding site of the receptor or affecting binding at the binding site of the receptor, such as an agonist or antagonist). In certain two hybrid assays (see infra), the test agent is one that is potentially able to influence the binding interaction between the binding proteins of the two fusions (see below).

Consequently, test agents can be of a variety of general types including, but not limited to, polypeptides; carbohydrates such as oligosaccharides and polysaccharides; polynucleotides; lipids or phospholipids; fatty acids; steroids; or amino acid analogs. Further, the compounds can be growth factors, hormones, neurotransmitters and vasodilators, for example. Likewise, the compounds can be of a variety of chemical types including, but not limited to, heterocyclic compounds, carbocyclic compounds, β-lactams, polycarbamates, oligomeric-N-substituted glycines, benzodiazepines, thiazolidinones and imidizolidinones. Certain test agents are small molecules, including synthesized organic compounds.

Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

D. Sample Dilution

The ability to regulate solution flow within the branch channel between holding spaces, mixers and chambers allows for sample dilution. This feature of the system is useful in diluting samples. Often drug candidates in libraries are dissolved in 100% dimethylsulfoxide. Since this solvent is incompatible with many biochemical assays until it is diluted to 1% or less in an aqueous buffer, a multi-stage dilution process can be conducted, whereby different buffer solutions are introduced into the chambers to achieve the desired level of dilution.

E. Screens with Cells

1. Devices for Use in Cellular Assays

Certain of the microfluidic devices disclosed herein utilize certain elements to facilitate assays conducted with cells, cell components or various other types of supports. In general, such microfluidic devices include a main flow channel and one or more branch flow channels in fluid communication with the main flow channel. The device can include a plurality of branch flow channels so that multiple assays can be conducted at the same time. Typically, the main and branch flow channels are formed within an elastomeric block.

In addition, a number of elastomeric valves can optionally be disposed along the length of the main flow channel and positioned adjacent each of the branch flow lines to regulate solution flow into the different branch flow channels. For example, elastomeric valves can be positioned such that by selectively activating different valves different solutions are introduced into different branch flow channels. In this way different cells and/or different reagents can be introduced into different branch flow channels. For instance, cells of the same type can be introduced into the various branch flow channels but different reagents subsequently introduced into the different branch flow channels such that a variety of different cell assays are conducted in the different branch flow channels. Optional valves can also be located within the branch flow channels adjacent the point at which the branch flow channel and main flow channel intersect to further control solution flow through the various channels. The solutions can be transported through the various flow channels by pressurizing or pulling a vacuum on the various flow channels or under the action of one or more elastomeric pumps having the design set forth above that are operatively disposed with respect to the different flow channels.

The devices can also include a pair of valves operatively disposed with respect to each of the branch flow channels. The valves can have any of the structures described supra. When these valves are closed, they enclose a volume of solution previously introduced into the branch flow channel and thus are sometimes referred to herein as "storage valves." Solution trapped in the space between the valves, as well as any agents within the solution (e.g., cells), can then be detected by a detector located to monitor the solution in the space between the two valves.

Figure 10:
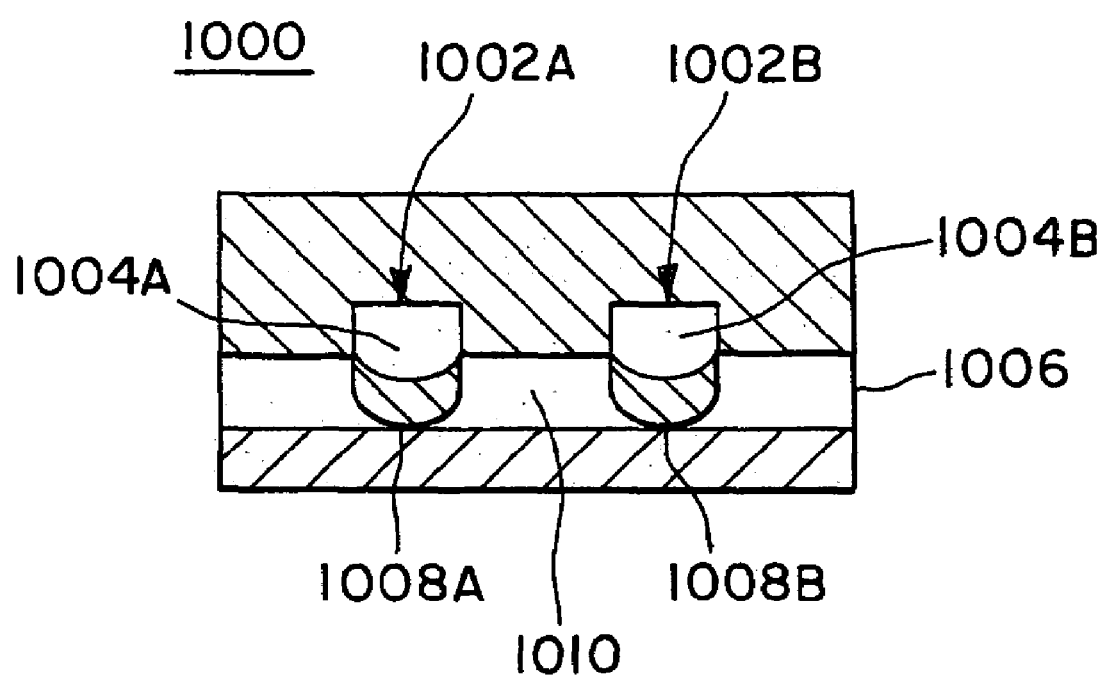
FIG. 10 is a cross-sectional view that illustrates the formation of a holding space within a flow channel upon actuation of valves in the flow channel.

An example of such an arrangement of storage valves is illustrated in greater detail in FIG. 10. This figure depicts an elastomeric block 1000, in which control channels 1002A, 1002B are disposed with respect to one another such that when the membrane sections 1008A, 1008B that separate the control channels 1002A, 1002B from the branch flow channel 1006 are extended into the branch channel 1006 a holding space 1010 is formed in which a volume of solution can be retained. An arrangement such as this in which two valves substantially block solution flow through the holding space is referred to herein as a "pen." As described in greater detail below, various other designs utilize valves having a grated-type structure that allows fluid to pass through the holding area while retaining cells therein.

Figure 19:
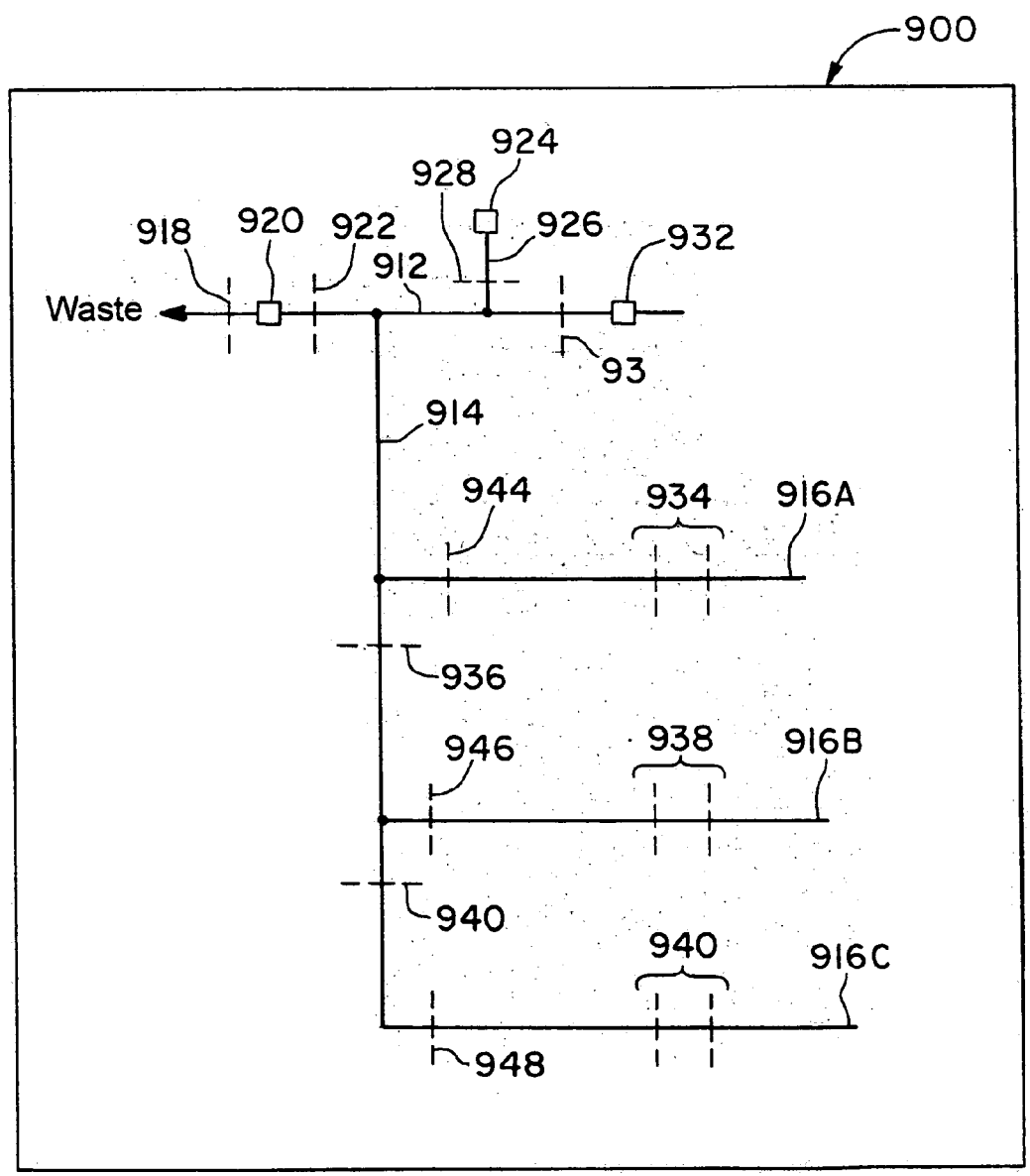
FIG. 19 depicts an exemplary microfluidic device useful for conducting cellular assays among other types of assays.

One particular exemplary configuration that illustrates certain features of microfluidic device that can be utilized to conduct a variety of cell assays is shown in FIG. 19. The device 900 is formed in an elastomeric block and includes an inlet flow channel 912 that is in fluid communication with a main flow channel 914, which in turn is in fluid communication with a plurality of branch flow channels 916A, 916B and 916C. Although FIG. 19 only depicts three branch flow channels, it should be recognized that many more branch flow channels can also be utilized. The inlet flow channel 912 includes a sample inlet 920 adapted to allow for the introduction of a sample containing one or more cells and an additional inlet 932. The inlet flow channel 912 is in fluid communication with an additional inlet flow channel 926 that includes inlet 924. The various inlets 924, 932 can be utilized to introduce a number of different solutions and/or agents into the inlet flow channel 912. Examples of such solutions, include but are not limited to, buffers, culture medium, dyes for staining cells, substrates of cellular enzymes and ligands for cell receptors. Solutions introduced into inlet flow channel 912 via the different inlets can flow into the main flow channel 914 and into the various branch flow channels 916A, 916B, 916C. Solution flow through the inlet flow channels can be regulated utilizing valves 918, 922, 928 and 930.

A plurality of valves 936 and 940 are operatively disposed along main flow channel 914 and positioned adjacent the branch flow channels 916A, 916B to allow solutions to be selectively introduced into the branch flow channels by closing the appropriate valve. The branch flow channels 916A, 916B and 9C each include a set of valves 934, 938 and 940 as described supra to form a holding space for cells introduced into the branch flow channels. The branch flow channels 916A, 916B, 916C also optionally include valves 944, 946, 948.

Figure 11A:
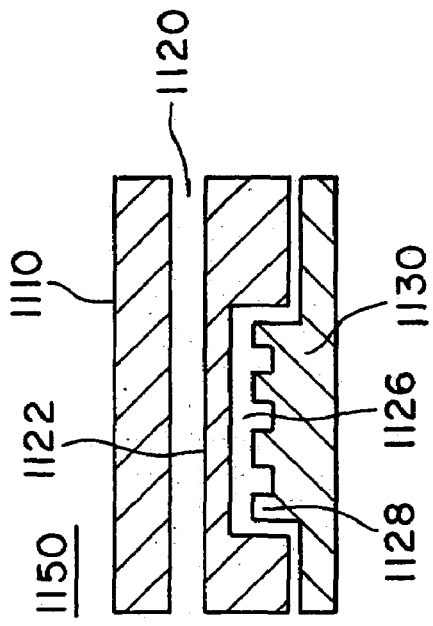
FIGS. 11A-11C depict different specific examples of cage structures.
Figure 11B:
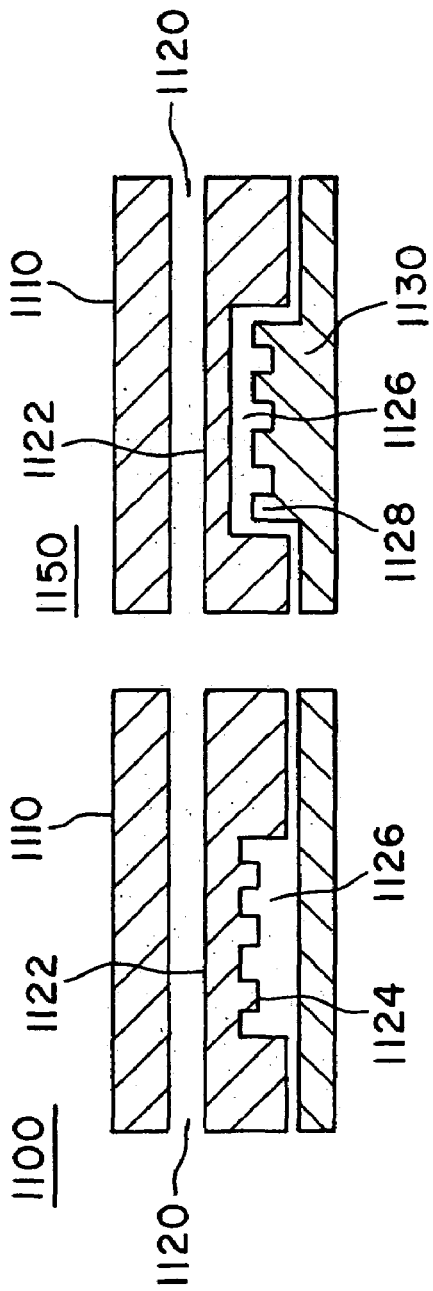
Figure 11C:
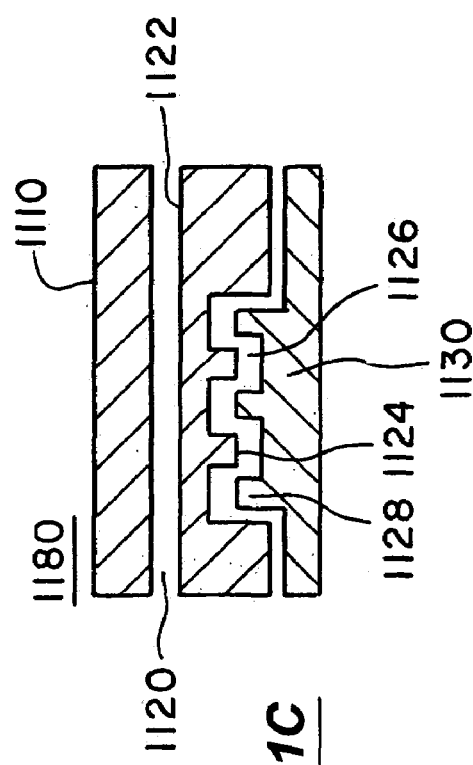

As indicated supra, each valve in the pair of valves 934, 938, 940 located in the branch flow channels 916A, 916B and 916C can have varying designs to facilitate certain, assay methods. For example, as illustrated in the cross section views shown in FIGS. 11A-11C, in some instances the membrane 1122 of the valve 1100 that separates a control channel 1120 and a flow channel 1126 include one or more protrusions 1124. The protrusions 1124 are of an appropriate size and shape and are spaced relative to one another such that when the membrane 1122 is extended into the flow channel 1126 the protrusions 1124 allow solution to pass through the space between protrusions while preventing cells to pass therethrough (FIG. 11A). Alternatively, as illustrated in FIG. 11B, the protrusions 1128 in other valves 1150 are located on a section 1130 of the branch flow channel 1126 opposite the membrane 1122 that separates a control channel 1120 and the branch flow channel 1126. Here, too, the protrusions 1128 are designed to allow for passage of a solution between the protrusions while preventing the passage of cells. Still another option is a valve 1180 utilizing both of the foregoing designs (FIG. 11C). Thus, the membrane 1122 between the control 1120 and branch flow channels 1126 includes elastomeric protrusions 1124 as does the section 1130 of the branch flow channel opposing the membrane (i.e., protrusions 1128). The two sets for protrusions are usually spaced relative to one another such that the protrusions at least partially interlock. However, even when interlocked, solution can flow through the protrusions but cells can not. Arrangements using such valves that allow for solution flow therethrough are referred to herein as "cages."

In operation, the methods generally involve introducing absolution containing cells into the different branch flow channels. The cells introduced in the different branch flow channels can be the same or different. The pair of valves positioned within each of the branch flow channels are then actuated to form the holding spaces (e.g., pens or cages) to trap or retain cells within the holding spaces. A detector (not shown) is typically positioned to monitor cells within the holding spaces. Thus, in screening assays involving cells, often the holding space is positioned within the detection section. Thus, the holding spaces can be utilized to hold cells in order to observe cell development and/or to detect signals generated during an assay (e.g., enzymatic products). This allows one to monitor or detect various cell features (e.g., cytological and toxicology studies) and to determine cell activities (e.g., enzyme activity). Alternatively, substances secreted from the cells can be detected.

Again referring to FIG. 19, an analysis can be initiated by closing valve 922 and opening valve 918 to flush sample through sample inlet 920. Subsequently, sample can be introduced into the main flow channel 914 by closing valve 918 and opening valve 922 such that solution introduced via sample inlet 920 flows into main flow channel 914. Valves 936, 940 can be utilized to control solution flow into the branch flow channels 916A, 916B and 916C. For instance, a solution containing cells can be introduced into all of the branch channels 916A, 916B, 916C by opening all of the valves (e.g., 936 and 940) along the main flow channel 14, as well as valves 944, 946, 948 within the branch flow channels. Alternatively, valves 936, 940 within the main flow channel 914 and the valves 944, 946, 948 within the branch flow channels 916A, 916B, 916C can be selectively actuated to introduce different solutions, and thus potentially different cells, into the different branch flow channels 916A, 916B, 916C.

Solutions other than those containing cells, for example, can be introduced via inlets 924 and 932. Introduction of solution via either of these inlets 924, 932 can be regulated using valves 928 and 930. As with the cell containing solutions, the same or different solutions can be introduced into the different branch flow channels 916A, 916B, 916C using the valves 936, 940 in the main flow channel 914, in combination with the valves 944, 946, 948 in the branch flow channels.

By using valves such as those described above that trap cells within a holding space while allowing for solution flow therethrough (i.e., cages); one can contact the cells in the holding areas with a variety of different solutions and agents while still monitoring the cells within the holding space. The extent to which the valve is closed can be regulated by controlling the extent of pressure within the control channel that actuates the valve.

The branch flow channels can also enable control experiments to be conducted in a facile manner. For instance, a set of test cells can be examined in one branch flow channel, while a population of control cells are treated and examined under similar conditions in an adjacent flow channel.

2. Cells

Essentially any type of cell can be utilized in the microfluidic cell assay devices provided herein. The flow channels utilized in the particular flow device are sized to accommodate the particular cells being utilized. The cells can be either prokaryotic or eukaryotic. The cells can also be from any source including, but not limited to, bacteria, yeast, insect, fungal, plant and animal cells. The animal cells can be from mammals or non-mammals. Exemplary mammalian cells include those typically utilized in the art such as CHO, HeLa, HepG2, BaF-3, Schneider, COS, CV-1, HuTu80, NTERA and 293 cells. The cells can be naturally-occurring cells or can be recombinant cells that harbor vectors including an exogenous gene. In some instances, the cells express a cell surface receptor of interest.

In many assays, the cells are alive and are metabolically functioning. The cells can be contained in tissue, blood and cell cultures, for example. The cells can also be part of cell-containing fluids, including but not limited to, spinal fluid, peritoneal fluid, tissue cell suspensions, samples obtained bone marrow aspirates or lymph nodes such as from a biopsy. With some applications, certain cell types are separated from other cells prior to injection into the microfluidic device. Such separations can be achieved using any of a variety of methods known to those of ordinary skill in the art including differential lysis, differential centrifugation and affinity columns.

Other assays are performed with components from cells. Thus, certain assays are conducted with cell lysates. Still other assays are conducted with vesicles.

3. Solutions/Agents

A wide variety of solutions can be flowed through the cages that retain the cells. In general, such solutions include, but are not limited to, culture medium utilized by the cells for growth, wastes generated by the cells and solutions containing various agents that interact or potentially interact with the cells. The agents can generally include any substance able to interact with the cell in some way. Certain agents are potentially able to generate some type of cellular response. Thus, the agents can include, but are not limited to, agents that potentially bind to a cellular receptor; substrates, cofactors and/or inhibitors of enzymes; dyes able to selectively label certain cells or cellular components; potential toxicants and the like.

4. Variations

The cages can also be utilized to trap cells and then allow agents secreted from the cells to pass from the cage and be detected downstream. Thus, for example, once cells have been retained in a cage, they can be contacted with various test agents. One way to evaluate the response of the cells to the test agent is to monitor agents secreted from the cell which pass through the openings in the cage.

The microfluidic devices are also not limited to performing assays with cells. The microfluidic devices can also be used to conduct assays in which certain assay components (e.g., a test agent) are attached to some type of support. A variety of supports can be utilized in the assays, provided the flow channels are sufficiently large to accommodate the supports. Often the supports are beads manufactured from glass, latex, cross-linked polystyrene or similar polymers (e.g., polyesters and cross linked polyacrylamide). Other supports are manufactured from gold or other colloidal metal particles. The supports can be of a variety of shapes, although typically the supports tend to be roughly spherical.

A variety of other supports can be utilized as well depending upon the particular application. Examples include, but are not limited to, nanoparticles (see, e.g., U.S. Pat. Nos. 5,578,325 and 5,543,158.), molecular scaffolds, liposomes (e.g., Deshmuck, D. S. et al. (1990) Life Sci. 28:239-242; and Aramaki, Y., et al. (1993) Pharm. Res. 10:1228-1231), protein cochleates (stable protein-phospholipid-calcium precipitates; see e.g., Chen, et al. (1996) J. Contr. Rel. 42:263-272) and clathrate complexes. Dendrimers can also be utilized in certain applications and can be synthesized to have precise shapes and sizes and to include a variety of functional groups at the surface to facilitate attachment of various assay agents (see, e.g., Tomalia, D. A. (1990) Angew. Chemie Int. Edn. 29:138-175).

The supports generally include one or more functional groups for the attachment of various assay components. Exemplary functional groups include hydroxyl, amino, carboxyl and sulfhydryl.

Additional discussion of methods and devices for conducting cell assays is set forth in copending and commonly owned application entitled "Apparatus and Methods for Conducting Cell Assays," filed on Apr. 6, 2001, and having attorney docket number 020174-003210US, which is incorporated herein by reference in its entirety for all purposes.

V. Combinatorial Synthesis

A. Methods

Microfluidic devices having the general arrangement of components as described for high throughput assays, particularly as depicted in FIG. 12, can also be utilized to conduct combinatorial or pseudo-combinatorial chemical synthesis. The methods generally parallel those described supra for the high throughput screening, except that instead of assay components and test agents being introduced into the flow channels different reactants are introduced instead. Thus, using certain of the devices provided herein, the test agents to be screened can be prepared.

Thus, with reference once again to FIG. 12, branch flow channel valves 808, 810, 812, 814, 816, 818 are closed and main flow channel valve 806 opened. A first reactant is then introduced into the main flow channel 802 via inlet 804 and allowed to flow into the chambers 82A-C along the main flow channel. Main flow channel valve 806 is then closed and the branch flow channel valves 808, 810, 812, 814, 816, 818 opened to introduce an additional reactant into each of the branch flow channels 842A-C. Reactants within each flow channel 842A-C flow into their chambers 820A-C were they become mixed with the reactant introduced into the main flow channel 802 to form nascent compounds. The resulting mixture in each chamber can then be transferred into the mixer in line with the chamber for further mixing/reaction or into a holding space (e.g., in the detection space 828A-C) within the branch flow channel associated with the chamber.

Additional reagents can be joined to the nascent compounds by various ways. One option is for a single reactant to be introduced into the main flow channel 802 and the chambers 820A-C located therein. Nascent compounds in the various flow channels 842A-C are then transported back to the chambers 820A-C for reaction with the newly introduced reactant introduced via the main flow channel 802. The resulting compounds are again transferred from the chambers 820A-C to their respective branch flow channel 842A-C. This process can be repeated as many times as necessary to obtain the final product.

An alternative to this iterative cycle is for additional reactants to be introduced into the branch flow channels 842A-C and the chambers 820A-C located therein. The nascent compounds in each branch flow channel 842A-C are then transported back to the chambers 820A-C for reaction with the newly introduced reactants. Following mixing within the chambers 820A-C, the mixtures are then transferred once again into the respective branch flow chambers 842A-C. This iterative process can be repeated with additional reactants to generate the desired library of compounds.

Further guidance regarding combinatorial methods is provide in PCT publications WO 93/06121, WO 95/12608, WO 95/35503, WO 94/08051 and WO 95/30642, each of which is incorporated herein by reference.

B. Compounds

The compounds generated by such methods can be composed of any components that can be joined to one another through chemical bonds in a series of steps. Thus, the components can be any class of monomer useful in combinatorial synthesis. Hence, the components, monomers, or building blocks (the foregoing terms being used interchangeably herein) can include, but are not limited to, amino acids, carbohydrates, lipids, phospholipids, carbamates, sulfones, sulfoxides, esters, nucleosides, heterocyclic molecules, amines, carboxylic acids, aldehydes, ketones, isocyanates, isothiocyanates, thiols, alkyl halides, phenolic molecules, boronic acids, stannanes, alkyl or aryl lithium molecules, Grignard reagents, alkenes, alkynes, dienes and urea derivatives. The type of components added in the various steps need not be the same at each step, although in some instances the type of components are the same in two or more of the steps. For example, a synthesis can involve the addition of different amino acids at each cycle, whereas, other reactions can include the addition of amino acids during only one cycle and the addition of different types of components in other cycles (e.g., aldehydes or isocyanates).

Given the diversity of components that can be utilized in the methods of the invention, the compounds capable of being formed are equally diverse. Essentially molecules of any type that can be formed in multiple cycles in which the ultimate compound or product, is formed in a component by component fashion can be synthesized according to the methods of the invention. Examples of compounds that can be synthesized include polypeptides, oligosaccharides, polynucleotide, phospholipids, lipids, benzodiazepines, thiazolidinones and imidizolidinones. As noted above, the final compounds can be linear, branched, cyclic or assume other conformations. The compounds can be designed to have potential biological activity or non-biological activity.

VI. Variations

A. Temperature Controller

With certain assays the ability to regulate temperature is an important feature. For example assays involving denaturation of proteins or thermal cycling reactions during primer extension and nucleic acid amplification reactions require temperature regulation. A number of different options are available for achieving such regulation that vary in degree of sophistication. Utilizing the following options one can regulate temperature throughout the device or to selectively regulate the temperature at particular locations. Furthermore, the temperature can be maintained at a relatively constant level or can be controlled according to a particular temperature profile or cycle.

One specific approach for regulating temperature within the devices is disclosed in U.S. Provisional Patent Application entitled "Nucleic Acid Amplification Utilizing Microfluidic Devices," filed Nov. 16, 2001, and having the disclosure of which is incorporated herein by reference in its entirety.

Another approach for regulating temperature within the devices is to employ external temperature control sources. Examples of such sources include, but are not limited to, heating blocks and water baths. Another option is to utilize a heating element such as a resistive heater that can be adjusted to a particular temperature. Such heaters are typically utilized when one seeks to simply maintain a particular temperature. Another suitable temperature controller include Peltier controllers (e.g., INB Products thermoelectric module model INB-2-(11-4)1.5). This controller is a two stage device capable of heating to 94° C. Such a controller can be utilized to achieve effective thermal cycling or to maintain isothermal incubations at any particular temperature.

In some devices and applications, heat exchangers can also be utilized in conjunction with one of the temperature control sources to regulate temperature. Such heat exchangers typically are made from various thermally conductive materials (e.g., various metals and ceramic materials) and are designed to present a relatively large external surface area to the adjacent region. Often this is accomplished by incorporating fins, spines, ribs and other related structures into the heat exchanger. Other suitable structures include coils and sintered structures. In certain devices, heat exchangers such as these are incorporated into a holding space, chamber or detection regions as described supra. Heat exchangers that can be utilized in certain applications are discussed, for example, in U.S. Pat. No. 6,171,850.

B. Channel Coatings

In certain methods, the flow channels are coated or treated with various agents to enhance certain aspects of the assay. For example, depending upon the nature of the material from which the flow channels are formed, it can be useful to coat the flow channels with an agent that protects against or prevents components of the assay (for example cells, proteins, peptides, substrates, small molecules) from adhering to the walls of the flow channels or to the sides of the wells through which these agents are introduced into the device. One function of these coatings is to help ensure the biological integrity of the introduced sample. Another function is to prevent physical interactions between cells and the walls of the channel that might affect cellular responses or functions in undesired ways. Examples of suitable coating agents include, but are not limited to, TEFLON, parylene, acrylamides, polyethylene glycol, silanes, and other agents to form self assembled monolayers.

Similarly channels can be modified with a variety of agents to achieve other purposes such as separation and sorting functions, with the goal being to prepare the flow channels in accordance with the particular application being conducted. More specifically, by properly selecting the bulk matrix of the flow channel (i.e., the particular choice of elastomers to utilize in constructing the flow channels), surface chemistry (i.e., modification of the properties of microchannels created within the elastomer) and the specific modification of regions of the elastomer surface (e.g., by covalent and/or non-covalent attachment of proteins, peptides, nucleic acids (or their analogs), lipids, carbohydrates) can facilitate the "tuning" of the device to a given application or combination of applications. Methods for modification of elastomer surfaces include, but are not limited to: (1) copolymerization with functional groups during elastomer curing (an example of bulk modification), (2) oxygen plasma treatment (3) modification of plasma treated surfaces with silanizing reagents (e.g., 3-aminopropyltriethoxysilane, N-(2-aminoethyl)-3-aminopropyltrimethoxysilane, dimethylchlorosilane or hexamethyldisilazane) which form self-assembled monolayers on the elastomer surface (which can be used to treat individual flow channels), (4) use of photochemical crosslinking reagents to create patterns of reactive groups on the elastomer surface (e.g., aryl azide derivatives or quinone-based derivatives), (5) passive modification of the elastomer surface by adsorption.

Adsorption also enables one to create secondary or tertiary layers of modification that offer improved properties over primary adsorption. As a specific example, one can use antibodies against an antigen to create a primary, coating of flow channel walls. If antigen is then bound to the bound antibody, one can then create a secondary layer of specifically bound antigen. Antigen bound in this way can be "presented" to the interior of the flow channel in a more appropriate way than as a passively adsorbed primary layer. Schemes for creating a plurality of layers composed of proteins, nucleic acids, lipids or carbohydrates or combinations thereof will be apparent to the skilled practitioner.

Channels can also be coated with materials that specifically bind to assay components and/or reaction products such as products produced by a cell or during an enzymatic assay, for instance. One example of such a coating is one in which the channel is coated with a metal or a metal-derivatized material. Reaction products bearing a metal chelate tag thus become bound to the metal-coated wall or material. Of course, a wide variety of other binding pairs could also be utilized as substitutes for the metal chelating agent and metal. Assays utilizing such metal-derivatized materials is discussed in greater detail infra on the section on enzymatic assays (see also U.S. Pat. No. 6,146,842).

C. Doping Channels with Magnetic Materials

The flow channel elastomeric walls can optionally be doped with magnetic materials or by integration of a preformed magnet or electromagnet into the microfluidic device. Examples of magnetic materials that can be incorporated include magnetically polarizable materials such as iron and permanently magnetized materials. Inclusion of such materials within the flow channel enables magnetic based separations to be performed.

D. Electrodes

The flow channels can also optionally include electrodes to provide an additional type of control over agent and solution transport. Integration of electrodes into the devices permits electrophoretic separations or electroosmotic flow to be integrated with pump-driven transport. Suitable electrodes can be formed by sputtering a thin layer of metal (e.g., gold) onto a surface in a flow channel. Other metallization approaches such as chemical epitaxy, evaporation, electroplating, and electroless plating can also be utilized to form the necessary conductive material. Physical transfer of a metal layer to the surface of the elastomer is also available, for example by evaporating a metal onto a flat substrate to which it adheres poorly, and then placing the elastomer onto the metal and peeling the metal off of the substrate. A conductive electrode can also be prepared by depositing carbon black (e.g., Cabot Vulcan XC72R) on the elastomer surface, either by wiping on the dry powder or by exposing the elastomer to a suspension of carbon black in a solvent which causes swelling of the elastomer, (such as a chlorinated solvent in the case of PDMS).

E. Membrane Integration

1. General

An additional element or module that can be incorporated into the microfluidic devices disclosed herein are elastomeric structures that include semi-permeable membranes that allow certain agents to pass therethrough, while other agents are not. As described in greater detail below, such modules can be used to perform a variety of useful functions. Such functions include, but are not limited to, dialysis to remove unwanted agents, purification and concentration.

2. Membrane Composition

The membranes utilized in the devices can be formed from almost any commercially-available polymer. Suitable commercially-available polymer membranes include, but are not limited to, cellulose, various cellulose esters (in particular cellulose acetate), nitrocellulose, polycarbonate, polyethylene, nylon, polypropylene, polysulfone, polyethersulfone, polystyrene, Teflon PTFE), polyvinylchloride (PVC) and polyvinylidenedifloride (PVDF). Membranes can also be formed from porous inorganic materials, including glass, quartz, and anodically-treated alumina ($Al_2O_3$) or other oxides, for example.

3. Preparation

Two basic methods exist for integrating membranes in elastomer based microfluidic devices: multilayer bonding-based methods and encapsulation-based methods. These methods correspond to multilayer soft lithography (MSL) and sacrificial-layer encapsulation (SLE) methods; these methods are described in detail in PCT Application No. 00/17740, in U.S. application Ser. No. 09/605,520, filed Jun. 27, 2000, and in U.S. application Ser. No. 09/724,784, filed Nov. 28, 2000, each of which is incorporated by reference in its entirety for all purposes. In general, multilayer soft lithography fabricates structures by molding and curing of polymers (elastomers) on micromachined substrates; each layer is cured separately, and then the layers are assembled together and bonded. The chemistry of the layers is chosen and/or manipulated to allow bonding of the cured layers. In the sacrificial layer encapsulation scheme, devices are fabricated by sequentially adding layers of elastomer and curing them, with microfluidic channels defined by patterned sacrificial layers added between layers of elastomer. This method requires care to choose a sacrificial layer compatible with the polymer chosen, but has the advantage that uncured polymer generally forms a good bond to cured polymer even without specific manipulation of the chemistry of the layers.

Different elastomeric layers can be joined using different approaches. In some instances, elastomeric layers are bonded together chemically, using chemistry that is intrinsic to the polymers comprising the patterned elastomer layers. For example, sometimes bonding is accomplished utilizing two component "addition cure" bonding.

In certain approaches, the various layers of elastomer are bound together by a heterogenous bonding in which the layers have a different chemistry. Alternatively, homogenous bonding can be used in which all layers are of the same chemistry. Thirdly, the respective elastomer layers can optionally be glued together by an adhesive. Yet another option if the elastomeric layers are thermoset elastomers is for the layers to be bonded together by heating.

With certain homogeneous bonding approaches, the elastomeric layers are composed of the same elastomer material, with the same chemical entity in one layer reacting with the same chemical entity in the other layer to bond the layers together. In some instances, bonding between polymer chains of like elastomer layers can result from activation of a crosslinking agent due to light, heat, or chemical reaction with a separate chemical species.

In certain heterogenous approaches in contrast, the elastomeric layers are composed of different elastomeric materials, with a first chemical entity in one layer reacting with a second chemical entity in another layer. For example, in certain heterogenous approaches; the bonding process used to bind respective elastomeric layers together involves bonding together two layers of RTV 615 silicone. RTV 615 silicone is two part addition cure silicone rubber. Part A contains vinyl groups and catalyst; part B contains silicon hydride (Si—H) groups. The conventional ratio for RTV 615 is 10A:1B. For bonding, one layer can be made with 30A:1B (i.e., excess vinyl groups) and the other with 3A:1B (i.e., excess Si—H groups). Each layer is cured separately. When the two layers are brought into contact and heated at elevated temperature, they bond irreversibly forming a monolithic elastomeric substrate.

Alternatively, other bonding methods can be used, including activating the elastomer surface, for example by plasma exposure, such that the elastomer layers/substrate bond when placed in contact. For example, one approach to bonding elastomer layers together that are composed of the same material is set forth by Duffy et al. (1998) Analytical Chemistry 70: 4974-4984, incorporated herein by reference in its entirety. Such an approach involves exposing polydimethylsiloxane (PDMS) layers to oxygen plasma to cause oxidation of the surface, with irreversible bonding occurring when the two oxidized layers are placed into contact.

Yet another approach to bonding together successive layers of elastomer is to utilizes the adhesive properties of uncured elastomer. Specifically, a thin layer of uncured elastomer such as RTV 615 is applied on top of a first cured elastomeric layer. Next, a second cured elastomeric layer is placed on top of the uncured elastomerc layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers can be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer creates a bond between the elastomeric layers and results in a monolithic elastomeric structure.

Figure 14:
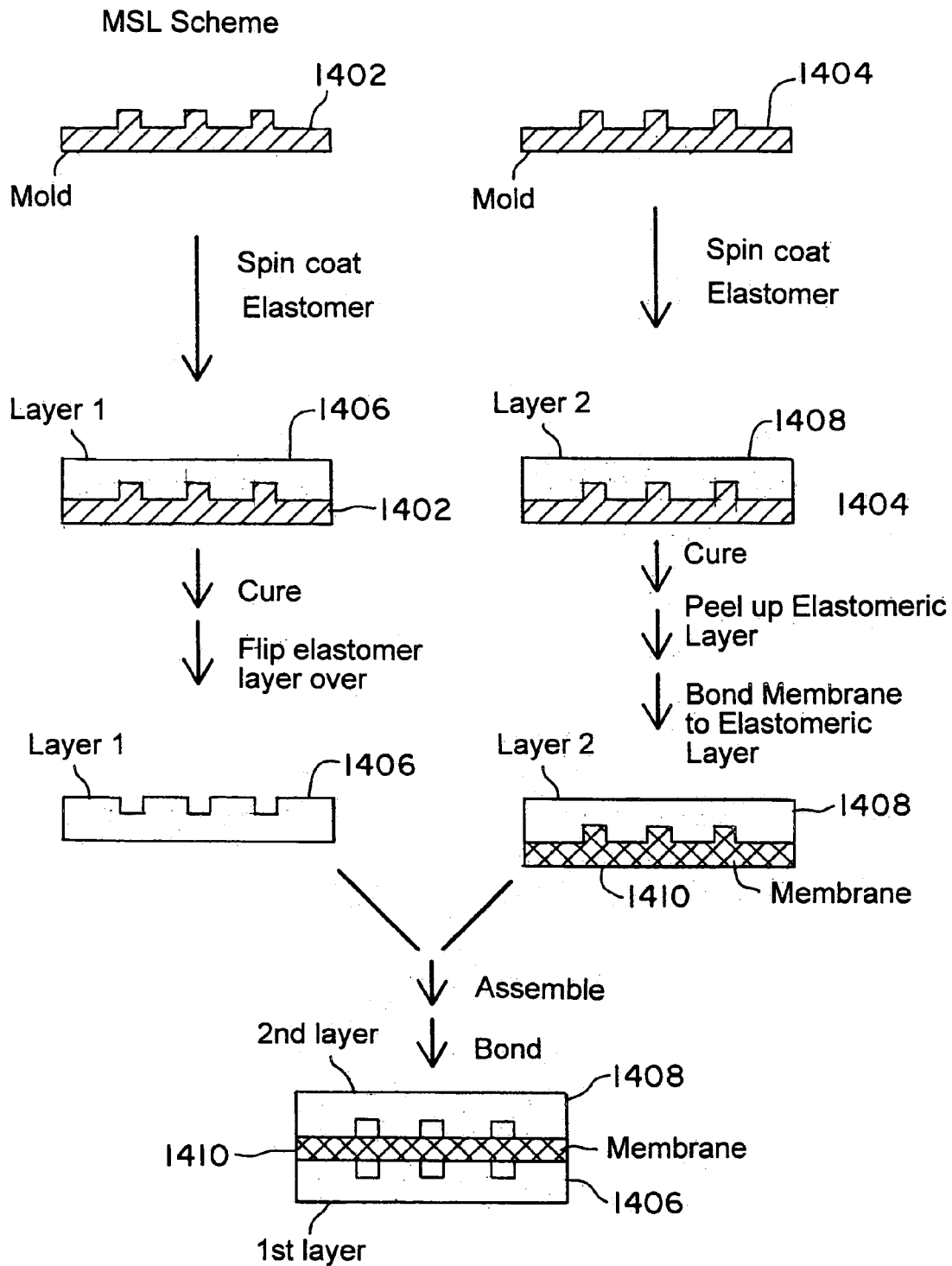
FIG. 14 illustrates a multilayer soft lithography method for incorporating membranes into elastomeric fluidic devices.

Although materials used for membranes typically are not elastomers, the methods used for fabrication of structures with integrated membranes are similar. Thus, for example, and as illustrated in the cross-sectional view shown in FIG. 14, certain multilayer soft lithography methods involve preparing two layers of elastomer 1406, 1408 by soft lithographic techniques in which elastomer is spin coated onto molds 1402, 1404. Membrane 1410 is bonded to one of the elastomer layers 1408 after elastomer layer 1408 has been peeled off of mold 1404 and cured. Elastomer layer 1406 is then turned over and assembled together with the assembly comprising elastomer layer 1408 and membrane 1410, all three elements being bonded together chemically. The chemistry of the elastomer layers 1406, 1408 and membrane 1410 to be chosen to allow bonding of the cured elastomer layers to the membrane. This can be accomplished by either using elastomers compatible with the membrane chemistry or by modifying the chemical groups on the surface of the membrane to allow bonding to the elastomer in use.

An example of the first process is to use a photocurable elastomer (e.g., Ebecryl 270, a urethane available from UCB Chemical) and bond the membrane 1410 to the elastomer 1408 using a photoinitiated reaction. An example of the second process involves modification of a cellulose membrane 1410 to produce a surface reactive towards hydroxyl groups, which groups are present at the sur face of a polyurethane elastomer produced with an excess of the diol component. Techniques for modification of polymer surfaces to allow the attachment of molecules are well known in the art, as these are the basis of solid phase synthesis (see, e.g., Hermanson, G. T., et al. (1992) "Immobilized Affinity Ligand Techniques" Academic Press, San Diego; and Zaragoza, D. F. (2000) "Organic Synthesis on Solid Phase: Supports, Linkers, Reactions," Wiley-VCH, N.Y.). The simplest rendition of membrane devices utilizing MSL techniques involves assembly of both elastomer layers 1406, 1408 with the membrane 1410 such that microfluidic channels face the membrane. This is somewhat different from other MSL schemes in which general layers are assembled "top to bottom" (i.e., with channels on the bottom side of each layer) rather than face-to-face. The technique and intent are the same, however.

Figure 15:
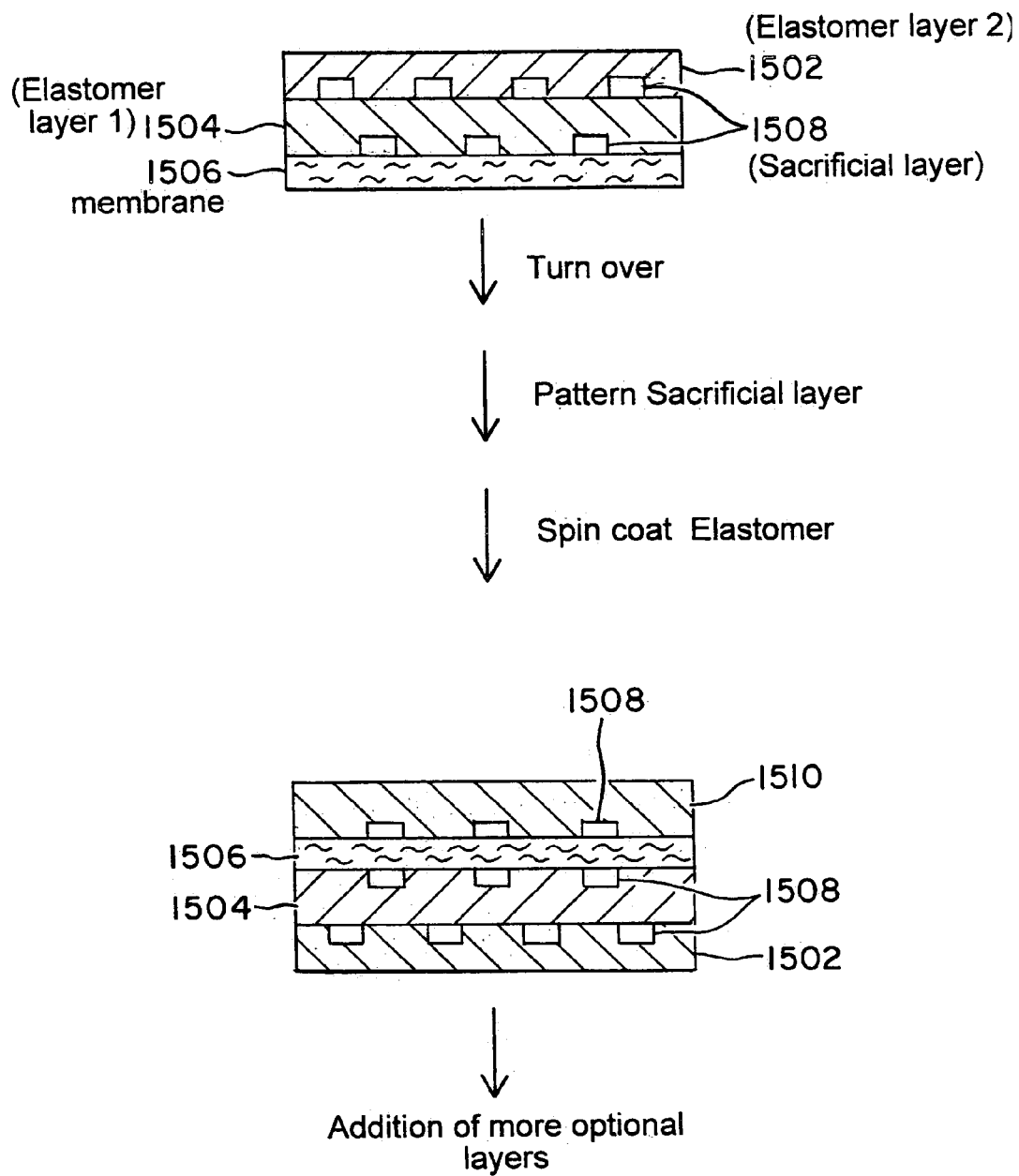
FIG. 15 illustrates a sacrificial layer encapsulation method for incorporating membranes into elastomeric fluidic devices.

An example of an encapsulation scheme is illustrated in FIG. 15. This example shows an assembly including a first elastomer layer 1504 attached to membrane 1506 and overlayed with a second elastomer layer 1502. As shown in this figure, some of the sacrificial layers 1508 are patterned directly on the membrane 1506, the elastomer 1504 coated on top of the sacrificial layer 1508 and cured. Multiple layers of elastomer and sacrificial layer can be added in order to make active elastomeric fluidic devices. The membrane-containing assembly is then turned over, a sacrificial layer 1508 patterned on the other side, and an elastomer layer 1510 built on that side as well. Again, multiple layers can be added. Finally, the sacrificial material is removed, leaving microchannels on both sides of the membrane in fluid communication with one another through the membrane. The advantage of this scheme is that uncured elastomer is very likely to form a chemical bond with the polymer membrane. Even with substrates that form no chemical bond with the elastomer, physical impregnation of the elastomer into the membrane matrix can yield a very strong attachment by this method.

Figure 16A:
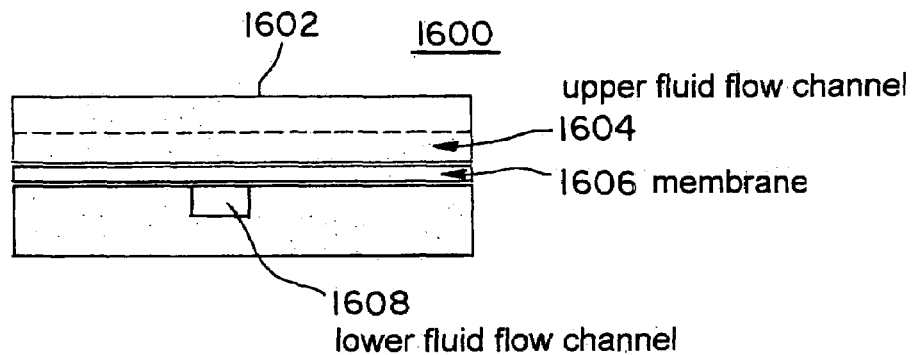
FIGS. 16A and 16B depicts an exemplary microfluidic device incorporating a membrane between flow channels.
Figure 16B:
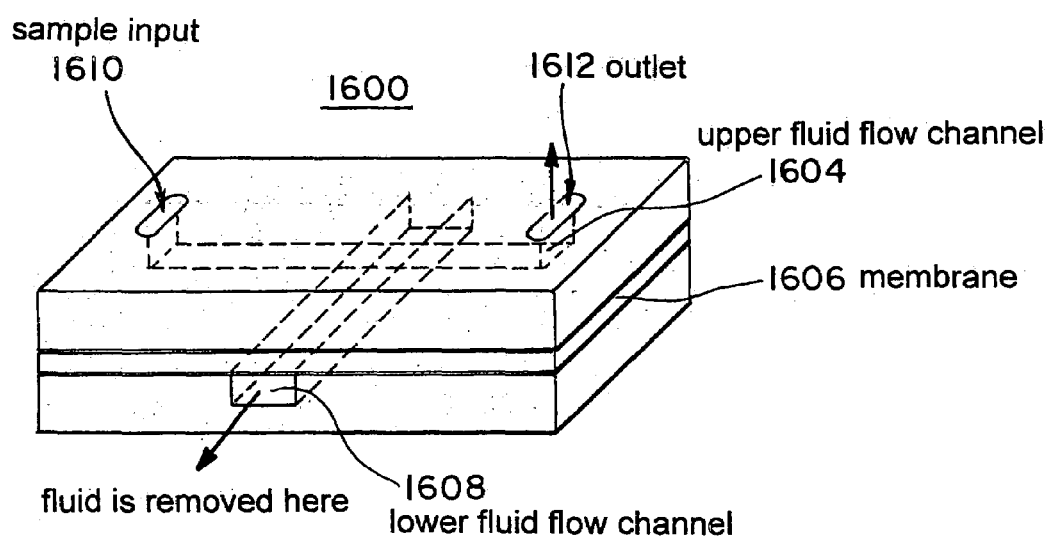

Another example of a device having a membrane component is illustrated in FIG. 16. As can be seen, this particular device 1600 also includes a flow channel 1604 in one layer of elastomer 1602 and a second flow channel 1608 in a second elastomer layer 1610. The two flow channels 1604, 1608 are separated by a membrane 1606. In this device 1600, however, the two flow channels 1604, 1608 are not oriented parallel to one another, but instead cross at an angle. The upper flow channel includes a sample input 1610 and an outlet 1612.

For inert membranes for which no elastomer can be found to form a chemical bond (e.g., Teflon), practical devices can nonetheless be assembled. Assembly follows the MSL scheme described supra, but the bond between the layers is limited to that provided by nonspecific (e.g., Van der Waals) forces. As elastomer microfluidic chips form a hermetic seal with nearly any flat surface, this seal usually is sufficiently strong to allow operation of the device.

4. Exemplary Uses

Figure 17:
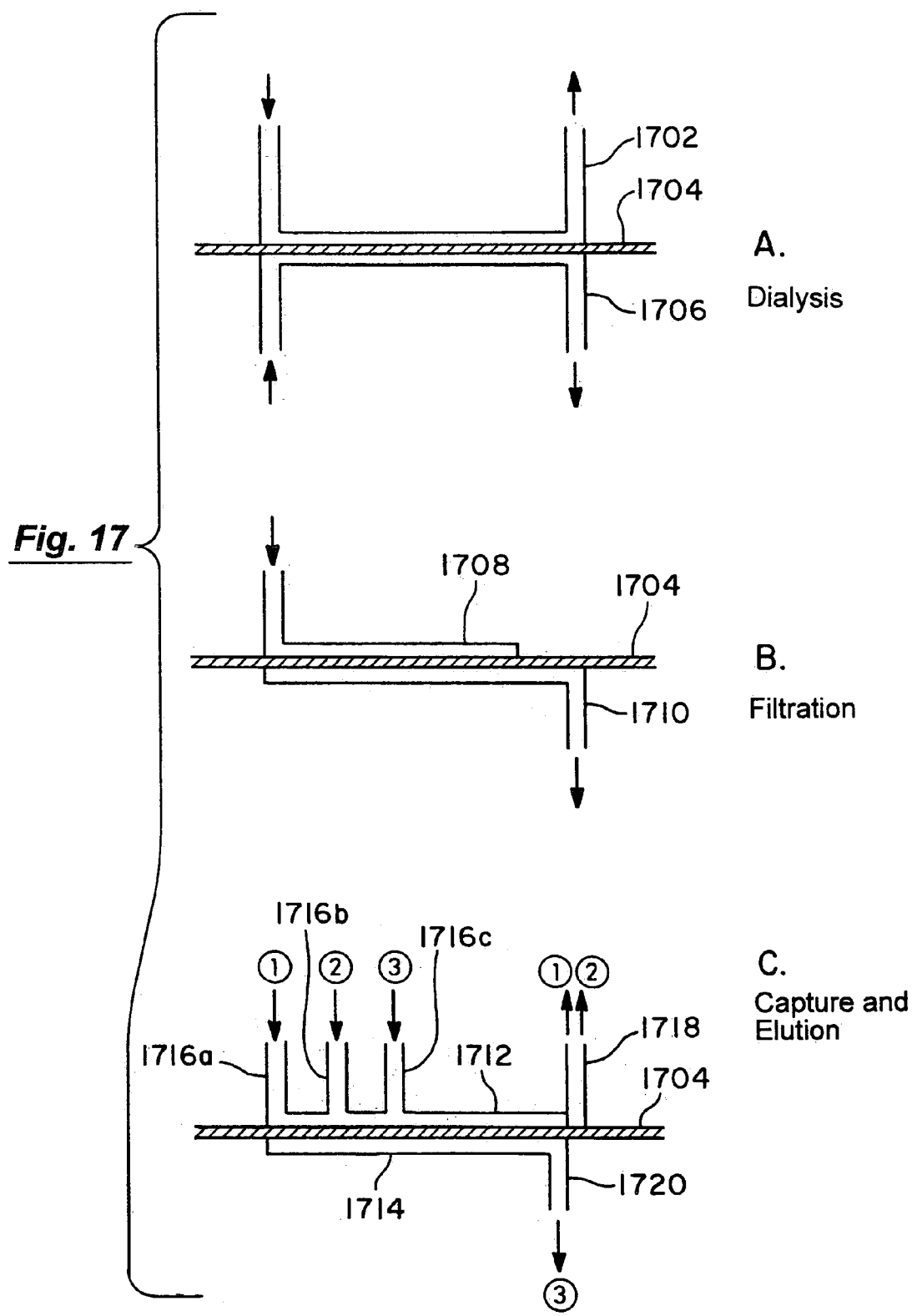
FIGS. 17A-17C show exemplary microfluidic devices incorporating membranes that can be utilized in dialysis, filtration and capture and elution applications.

In general, the devices including a membrane that separates two flow channels can be used in a variety of separation and concentration applications. As illustrated in FIGS. 17A-C. for example, the membrane devices or modules can be utilized to perform a number of different functions. FIG. 17A, shows a device in which two parallel channels 1702, 1706 are separated by a membrane 1704, with a flow of solution in one channel and a slower flow of solution or static fluid in the other channel (solution flow represented by arrows). Such an arrangement is useful for removing small molecules from a mixture. For example, this type of an arrangement can be used in dialysis. A specific application of such a device, is to remove salt from a biological sample (e.g., salt from an enzyme preparation).

FIG. 17B depicts another arrangement in which parallel channels 1708, 1710 (or chambers) are separated by a membrane 1704. In this instance, applying pressure to one channel (e.g., channel 1708) causes solution to flow through the membrane 1704, with particles/molecules larger than a certain size retained on one side (e.g., in channel 1708) and particles/molecules smaller than that size passing through into channel 1710. Such an arrangement can be considered as an ultrafiltration device. This device is useful for removing small particles/molecules from a sample and retaining the larger molecules. The applied pressure allows larger molecules to be concentrated. Typically the applied pressure is some type of gas (e.g., air).

FIG. 17C shows another configuration in which parallel channels 1712, 1714 (or chambers) are separated by a membrane 1704, with a plurality of inlets 1716a, 1716b, 1716c available to flow in a sample and other optional agents. In this particular device, the membrane composition allows binding of a component of the sample to the membrane 1704. Another solution can be flowed into channel 1712 via inlet 1716b to wash away the non-bound components of the mixture; yet another solution can be introduced into channel 1712 (e.g., via inlet 1716c) to release the bound component from the mixture. Released components can be directed to an outlet 1718 in channel 1712 or on the opposite side of the membrane 1704 via outlet 1720.

In some assays, cells are bound to the membrane 1704 (or anywhere along flow channel 1712) and an agent that affects the cell is added into flow channel 1704 via one of the inlets 1716a-c. Small molecular weight compounds produced by the cells pass through the membrane 1704 and are collected through outlet 1720 for further analysis.

F. Separation Module

Figure 18A:
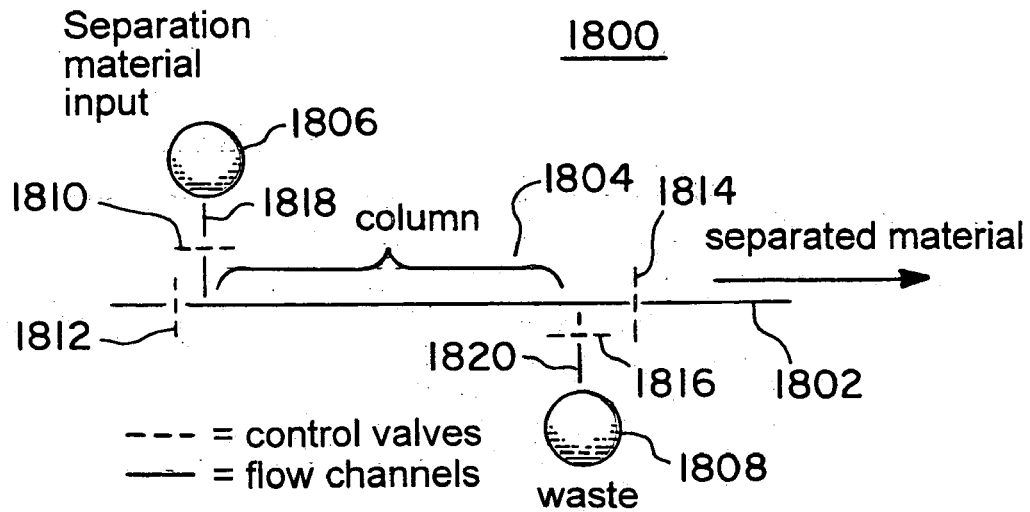
FIG. 18A illustrates elements of a separation module that can be incorporated into microfluidic devices or used as a stand alone microfluidic device.
Figure 18B:
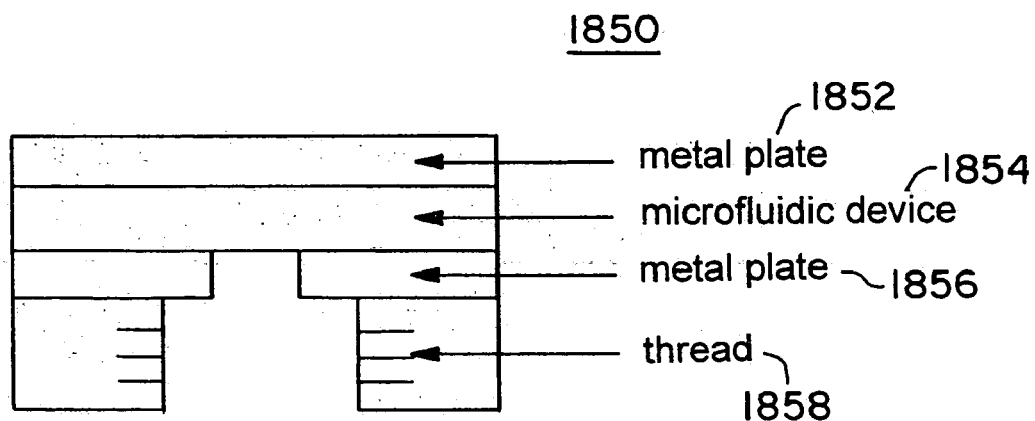
FIG. 18B depicts an arrangement to prevent separation of elastomer layers in a microfluidic device when flow channels are subjected to high pressures.

A separation module or modules can also be incorporated into the present microfluidic devices. Such a module allows components within a solution to be separated, or at least partially separated, from one another. One particular module is illustrated in FIGS. 18A and 18B. In general the module 1800 includes a flow channel 1802, which is in fluid communication with an inlet 1806 for introducing separation material and a waste outlet 1808. The region in which separation material is located is referred to as the column region 1804. Various control valves 1810, 1812, 1814, 1816 can be actuated to regulate introduction of separation material, the exit of waste and flow through the column 1804.

Separation materials packed along the column region 1804 by opening the valve 1810 in the separation material input channel 1818 and the valve 1816 in the waste channel 1820. The column separation material is allowed to flow from the separation material input channel 1818 to the waste collection site 1808. After the column has been packed, the separation material input channel 1818 and the waste channel 1820 are closed using valves 1810 and 1816, respectively. If the separation module is part of a device such as shown in FIGS. 12 or 13, the solution flowing into the column 1804 typically is a solution moving downstream from an upstream location in which various assay components have been added (and often mixed). The separation column 1804 can be used to separate components in an assay solution mixture prior to detection in a detection section. This module can be used as a stand alone device, however, with a separate sample inlet (not shown) in fluid communication with a section of the flow channel 1802 upstream of the column region 1804.

A wide variety of separation materials can be utilized in the column to effect separation. In general, the separation material can include any material that allows separation of components according to affinity, size, mobility, and the like. Specific examples of separation material include, but are not limited to, size exclusion material, ion exchange material, cross-linked polymeric gels (e.g., polyacrylamide) and affinity chromatography material.

Size exclusion materials can be used to separate components based upon size. Such separations can be conducted as part of a desalting operation or to separate similar compounds that differ in size, (e.g., proteins of different molecular weight). Ion exchange chromatographic material can be utilized to separate charged agents and/or to exchange one counterion for another. Affinity chromatography materials can be used to selectively bind certain components.

Certain separation modules are designed to conduct electrophoretic separations. Thus, the column 1804 includes a gel matrix (e.g., polyacrylamide or agarose). Electrodes of the type described supra can positioned at opposing ends of the column and used to apply a voltage across the column 1804.

The amount of pressure required to flow the sample fluid through the column can cause separation of joints within the microfluidic device. To prevent separation of layers or joints, an assembly, 1850 includes a microfluidic device 1854 sandwiched between two metal plates 1852 and 1856. A pressure screw 1858 can be utilized to apply pressure between the two plates 1856 and 1852 to keep the RTV layers of the microfluidic device from separating at high pressure.

Other types of separations systems are described in U.S. provisional patent application entitled "Microfluidic Sample Separation Device," having, which is incorporated by reference herein in its entirety for all purposes.

VII. Exemplary Applications

The microfluidic devices disclosed herein can be utilized to conduct a variety of different assays. Essentially any biological assay or library screening application can be performed with the microfluidic devices that are described herein, provided none of the components of the assay or screen are incompatible with the size of the microfluidic channels. For example, the present high throughput screening devices can be used to screen for any agents that affect the activity of any class of "druggable" targets (i.e., a target that is able to be modulated by a small molecule to produce a desired phenotypic change in cell targets). Potential druggable targets include, but are not limited to, G-protein coupled receptors (GPCRs), coytkines and cytokine receptors, nuclear receptors (ligand-dependent transcription factors), signaling processes (e.g., receptor-ligand interactions, calcium mobilization, kinases and phosphatases, second messengers and transcription factors), proteases, ion channels, and determinants of cytotoxicity (e.g., pro- and anti-apoptotic processes and cell death). These targets can be addressed by the various types of assays described herein, including, for example, fluorescent detection technologies such as fluorescence intensity determinations, fluorescence polarization, fluorescence resonance energy transfer, time-resolved techniques and fluorescence correlation spectroscopy.

The following include a non-exhaustive list of illustrative assays that can be conducted with the microfluidic devices provided herein, and illustrate the nature of the targets that can be investigated and the types of detection schemes that can be utilized.

A. Enrichment of Selected Cells/Cellular Components

1. General

Certain cells and cell components can be selectively enriched within a section of a flow channel. The term "cell component" broadly refers to an agent that is part of the cell, contained within the cell or produced by the cell. Thus, the component can be a structural agent (e.g., a membrane, tubule or protein) a cytoplasmic component or a product generated through a metabolic or catabolic activity of the cell, for instance. The "enrichment" section or zone can be located within a detection section or at other sections of the flow channel system, for example. An enrichment section in general includes an agent that is a member of a binding pair and that selectively interacts with a particular target cell or cellular component of interest that includes the other member of the binding pair. In the case of cells, the agent can be a ligand that interacts with an antiligand (e.g., a receptor) on the cell surface. The interaction between the agent and the selected cells or cell products can be a stable interaction in which the cell or cell component becomes immobilized within the enrichment section or an interaction that simply slows flow of the selected cells or cell products through the enrichment region relative to other cells or cell products.

The enrichment section can be designed to contain agents that specifically interact with a wide variety of molecules on the surface of the target cell or that are part of the cell component. Examples of suitable agents that can function as one member of the binding pair include, but are not limited to, lectins, enzyme cofactors, enzyme inhibitors, ligands for receptors and antibodies that recognize particular cell markers. Such antibodies can be directed toward any of a variety of different markers displayed on the target cell surface. Examples of such markers or antigens include markers for T cells or T cell subsets, B cells, monocytes, leukocytes, myeloid cells, HLA Class II positive cells and stem cells.

2. Coated Channels

One option for presenting the agent to the selected cells is to coat the enrichment section with the agent as described supra in the channel coating section. Thus, for example, a ligand can be attached to the interior surface of the flow channel that binds to an antiligand exposed on the exterior surface of the selected cells. Alternatively, multiple layers can be formed on the flow channel surface. For instance, an antibody that specifically binds to a particular antigen that is recognized by the target cells of interest can be coated onto the flow channel surface. The antigen can then be added as a second layer by contacting the immobilized antibody with the antigen. Thus, the flow channel displays antigen to cells passing through the enrichment region. Cells that bind the antigen (e.g., cells expressing a receptor that binds the antigen) are thus retained within the enrichment zone while other cells can flow through.

3. Coated Supports

Another option for preparing an enrichment region is to utilize supports that are coated with the binding pair member such that target cells or cell components having the other binding pair member become complexed with the coated supports.

Binding pair members can be attached to supports utilizing a number of well established chemistries. For example, tosylactivated forms of the supports can be utilized to custom coat the supports with the agent of choice. Streptavidin coated supports can be conjugated with biotinylated agents.

Supports can be retained within a particular desired region in a number of different ways. For instance, porous class frits or plugs of porous materials (e.g., polymeric gels such agarose gel) can be utilized at the inlet and outlet of the enrichment section. If paramagnetic supports are utilized, coated supports can be retained utilizing applied magnetic fields.

4. Impregnated or Coated Membranes

The enrichment section can also utilize coated or impregnated membranes to selectively enrich particular cells or cell components. These membranes are either coated or impregnated with an agent/binding pair member such as those described supra. The membrane can be utilized to selectively retain certain targets, while allowing other molecules to pass through the membrane and from the enrichment region for transport to another section of the microfluidic device (e.g., a waste outlet). Membranes of this type can be fabricated into the devices described herein as set forth in the membrane integration section supra.

Using such membranes, one can selectively retain molecules above a certain cutoff size (i.e., macromolecules or cells that are larger than the pore sizes within the membrane) and/or retain target cell components. Thus, for example, by utilizing a an appropriate membrane, one can retain cells within the enrichment section by virtue of their size (i.e., they are too large to pass through the membrane), while simultaneously retaining a cell product produced by the cell by virtue of its binding to its binding partner that is impregnated into or coated on the membrane. In this way, one can enhance the ability to detect cell products that are formed at very low levels. A variety of membranes that can be utilized in selective enrichment of certain agents is discussed, for example, by Tomlinson, et al. (1995) J. Cap. Elect. 2:97-104; and Tomlinson, et al. (1995) J. High Res. Chromatogr. 18:381-3.

5. Variations

Of course, the enrichment sections can also be utilized to enrich for agents other than cells or cell components. The detection sections can also or alternatively be designed to enrich any number of other agents. Thus, the enrichment section can be utilized to enrich for a particular assay reagent (e.g., an enzyme substrate) or agent that reacts with a product generated by a cell, for example. Those having ordinary skill in the art will appreciate that a large number of other agents can also be enriched utilizing the devices and according to the methods disclosed herein.

While the above methods have described systems in which one member of a binding pair is utilized to selectively retain target cells or cell components within the enrichment section, the reverse approach can also be utilized in which a binding pair member that is present on cells other than the target cell or cell component is used to retain non-target cells while the target cell or cell component pass through the enrichment sections. The target cells can subsequently be collected and assayed free of other cells.

B. Detecting Presence of Particular Cells

The enrichment methods just described provide some techniques for detecting selected target cells of interest. Various other methods are also available for detecting the presence of target cells. One option is to provide a detection section which permits one to examine cell morphology either directly or more typically by conventional microscopy. Thus, a microscope can be aligned with a section of the microfluidic device in which the target cells are contained (e.g., within a cell pen or cage as described supra or within an enrichment section). Identification of some cells can in some instances be enhanced by applying histological stains that are known in the art to selectively stain the cells of interest.

As discussed above, another strategy is to detect target cells according to particular protein markers that are expressed by the cells of interest. Such markers are typically identified using labeled antibodies that specifically recognize the distinctive cell marker.

Yet another option is to examine the mRNA (or a nucleic acid molecule derived therefrom such as a cDNA) that is transcribed by cells, as different cell types typically have different mRNA profiles. This is particularly true of certain types of cells. Examples of such cells include, but are not limited to, cells infected with bacteria or viruses, cancerous cells which transcribe specific mRNAs, cells transcribing mRNA isoforms that include one or more sites of mutation, keratinocytes (keratin mRNA), and chondrocytes (aggrecan mRNA). One approach for utilizing this approach involves using primer pairs that enable one to distinguish between mRNA and genomic DNA signal. For example, one can select primers that amplify a short segment of mRNA where an intron is present in the corresponding genomic sequence.

Certain assays involve isolating cells within a region of the microfluidic device, such as in a pen or cage as described supra. An assay mixture containing a cell lysing agent or detergent (e.g., TWEEN-20), optionally an RNase inhibitor to inhibit the degradation of the mRNA and the agents necessary to conduct a RT-PCR reaction (e.g., primers and polymerase) are introduced into the microfluidic device and transported to the cells. By utilizing heaters such as described above, one can conduct the cycling steps to perform the RT-PCR. Amplification products can be detected by utilizing labeled primers which thus generate labeled products. In some assays, amplified product can optionally be separated from labeled printer in a separation module as described above.

C. Cell Reporter Assays

A number of different cell reporter assays can be conducted with the provided microfluidic devices. One common type of reporter assay that can be conducted include those designed to identify agents that can bind to a cellular receptor and trigger the activation of an intracellular signal or signal cascade that activates transcription of a reporter construct. Such assays are useful for identifying compounds that can activate expression of a gene of interest. Two-hybrid assays are another major group of cell reporter assays that can be performed with the devices. The two hybrid assays are useful for investigating binding interactions between proteins. These are discussed in greater detail in the following sections.

Often cell reporter assays are utilized to screen libraries of compounds. Although a variety of microfluidic devices including the various components disclosed herein can be used, a device such as that shown in FIG. 9 can be utilized in the high throughput screening of a library of compounds for their ability to activate a receptor or influence binding between binding proteins. In general such methods involve introducing the cells into the main flow channel so that cells are retained in the chambers located at the intersection between the main flow channel and branch channels. Different test agents (e.g., from a library) can then be introduced into the different branch channels where they become mixed with the cells in the chambers.

Alternatively, cells can be introduced via the main flow channel and then transferred into the branch channel, where the cells are stored in the holding areas. Meanwhile, different test compounds are introduced into the different branch flow channels, usually to at least partially fill the chambers located at the intersection of the main and branch flow channels. The cells retained in the holding area can be released by opening the appropriate valves and the cells transferred to the chambers for interaction with the different test compounds. Once the cells and test compounds have been mixed, the resulting solution is returned to the holding space or transported to the detection section for detection of reporter expression. The cells and test agents can optionally be further mixed and incubated using mixers of the design set forth above.

1. Receptor Binding and Gene Activation

The cells utilized in screening compounds to identify those able to trigger gene expression typically express a receptor of interest and harbor a heterologous reporter construct. The receptor is one which activates transcription of a gene upon binding of a ligand to the receptor. The reporter construct is usually a vector that includes a transcriptional control element and a reporter gene operably linked thereto. The transcriptional control element is a genetic element that is responsive to an intracellular signal (e.g., a transcription factor) generated upon binding of a ligand to the receptor under investigation. The reporter gene encodes a detectable transcriptional or translational product. Often the reporter (e.g., an to enzyme) can generate an optical signal that can be detected by a detector associated with a microfluidic device. General cell reporter systems are discussed in U.S. Pat. No. 5,436,128. In addition to their use in identifying compounds that are ligands of receptors that trigger gene activation, the methods can also be used to identify compounds that are agonists or antagonists of receptors of interest.

A wide variety of receptor types can be screened. The receptors often are cell-surface receptors, but intracellular receptors can also be investigated provided the test compounds being screened are able to enter into the cell. Examples of receptors that can be investigated include, but are not limited to, ion channels (e.g., calcium, sodium, potassium channels), voltage-gated ion channels, ligand gated ion channels (e.g., acetyl choline receptors, and GABA (gamma-aminobutyric acid) receptors), growth factor receptors, muscarinic receptors, glutamate receptors, adrenergic receptors, dopamine receptors (see, e.g., U.S. Pat. Nos. 5,401,629 and 5,436,128). Additional receptors include the G-protein coupled receptors, specific examples of which include substance K receptor, the angiotensin receptor, the α- and β-adrenergic receptors, the serotonin receptors, and PAF receptor (see, e.g., Gilman (1987) Ann. Rev. Biochem. 56: 625-649).

A number of different reporters can be used to detect gene activation. Certain reporter gene encode proteins that are inherently detectable. One specific example of such a reporter is green fluorescent protein. Fluorescence generated from this protein can be detected with various commercially available detection systems. Other reporters can be detected by staining. Most commonly, however, the reporter is an enzyme that generates a detectable signal when contacted with an appropriate substrate. Often the reporter is an enzyme that catalyzes the formation of a detectable product. Suitable enzymes include, but are not limited to, proteases, nucleases, lipases, phosphatases and hydrolases. Typically, the reporter encodes an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282:864-869); luciferase (lux); β-galactosidase; LacZ;

β-glucuronidase; and alkaline phosphatase (Toh, et al. (1980) Eur. J. Biochem. 182:231-238; and Hall et al. (1983) J. Mol. Appl. Gen. 2:101), each of which are incorporated by reference herein in its entirety. Other suitable reporters include those that encode for a particular epitope that can be detected with a labeled antibody that specifically recognizes the epitope.

The cells utilized in the cell based assay can include any of those described supra. In general, the cells must express the receptor of interest. The receptor can be an endogenous receptor or a receptor expressed from a heterologous construct that includes the gene that encodes for the receptor of interest. In the latter instance, the cell must be able to transfected with the construct and able to express the heterologous receptor.

2. Two Hybrid Assays

Another general category of cell assays that can be performed is the two hybrid assays. In general, the two-hybrid assays exploit the fact that many eukaryotic transcription factors include a distinct DNA-binding domain and a distinct transcriptional activation domain to detect interactions between two different hybrid or fusion proteins. Thus, the cells utilized in two-hybrid assays include the construct(s) that encode for the two fusion proteins. These two domains are fused to separate binding proteins potentially capable of interacting with one another under certain conditions. The cells utilized in conducting two-hybrid assays contain a reporter gene whose expression depends upon either an interaction, or lack of interaction, between the two fusion proteins.

In standard two-hybrid systems, interaction between the two binding proteins results in expression of the reporter gene (see, e.g., Fields. S. and Song, O (1989) Nature 340:245; Bartel, P. L., and Fields, S. (1995) Methods in Enzymology 254:241-263; Heery, D. M., et al. (1997) Nature 387:733-736; and Bartel, et al. (1993) Biotechniques 14:920). Reverse hybrid systems, in contrast, are designed such that interaction between the two binding proteins suppresses reporter expression. In these systems, reporter expression is triggered when a compound inhibits the interaction between the two binding proteins (see, e.g., PCT publication WO 95/26400). Two-hybrid assays can be utilized to establish interactions between two known proteins or to search a genomic or cDNA library for proteins that interact with a target protein.

D. Binding Assays

1. General

A wide variety of binding assays can be conducted utilizing the microfluidic devices disclosed herein. Interactions between essentially any ligand and antiligand can be detected. Examples of ligand/antiligand binding interactions that can be investigated include, but are not limited to, enzyme/ligand interactions (e.g., substrates, cofactors, inhibitors); receptor/ligand; antigen/antibody; protein/protein (homophilic/heterophilic interactions); protein/nucleic; DNA/DNA; and DNA/RNA. Thus, the assays can be used to identify. agonists and antagonists to receptors of interest, to identify ligands able to bind receptors and trigger an intracellular signal cascade, and to identify complementary nucleic acids, for example. Assays can be conducted in direct binding formats in which a ligand and putative antiligand are contacted with one another or in competitive binding formats well known to those of ordinary skill in the art.

Because the microfluidic devices typically include a plurality of branch flow channels and holding spaces that allow multiple analyses to be conducted at the same time, a large number of assays can be conducted in a short period. Throughput can be increased even further by utilizing additional multiplexing techniques. In this way, different ligands or antiligands can be attached to different supports and a plurality of supports assayed within a single branch flow channel. Active ligands or antiligands can be identified on the basis of the distinguishable supports. For example, assays can be conducted using supports that can be distinguished by physical, chemical, visual or other means. More specifically, supports can be distinguished from one another on the basis of different composition, size, color, shape, magnetic properties, chemical properties, electronic properties, fluorescent emission, for example. Specific examples of supports that can be distinguished on the basis of different fluorescent emissions are Luminex beads (Luminex Corporation) and Quantum dots (Quantum Dot Corporation). Sorting and/or quantitation is based upon support size, wavelength and/or amount of signal generated (e.g., fluorescence).

Binding assays generally involve contacting a solution containing ligands with a solution containing antiligands and allowing the solutions to remain in contact for a sufficient period such that binding partners form complexes. The ligand and/or antiligand is usually labeled. Any of a variety of different labels can be utilized as described above. Ligands and antiligands can be contacted within the main or branch flow channels. More typically, however, contact occurs within the chambers and/or holding spaces (e.g., pens or cages) described supra. Solutions containing the ligands and antiligands can be mixed and/or incubated by pumping solutions back and forth between chambers and holding spaces and/or by using the mixers described supra. Complexes typically are detected within a detection sections along the flow channel. The detection section can include holding spaces (e.g., pens or cages) as described supra. The type of detector and detection method utilized depends upon the type of label used to label the ligand or antiligand.

2. Heterogeneous Formats

Heterogenous binding assays involve a step in which complexes are separated from unreacted agents so that labeled complexes can be distinguished from uncomplexed labeled reactants. Often is achieved by attaching either the ligand or antiligand to a support. After ligands and antiligands have been brought into contact, uncomplexed reactants are washed away and the remaining complexes subsequently detected.

The heterogeneous assays performed with the microfluidic devices disclosed herein generally involve contacting a solution containing a ligand and a solution containing an antiligand with one another under conditions and for a sufficient period of time to allow a ligand/antiligand complex to form. Since the ligand or antiligand is labeled, any complexes formed can be detected on the basis of the label in the complex.

The assays can be conducted in a variety of ways. One approach involves anchoring an antiligand of interest to some type of a solid support and contacting the antiligand with a solution containing ligands. Labeled ligands that do not form complexes are washed away under conditions such that complexes that are formed remain immobilized to the solid support. The detection of complexes immobilized to the support can be accomplished in a number of ways. If the non-immobilized ligand is labeled, the detection of label immobilized on the solid support indicates that a ligand/antiligand complex has been formed. If, however, the non-immobilized ligand is not labeled, complexes can nonetheless be detected by indirect means. For instance, a labeled antibody that specifically binds to the ligand can be utilized to detect complexes anchored to the support.

Alternatively, ligands and antiligands can be contacted in solution. Complexes can then be separated from uncomplexed ligands and antiligands and complexes detected. One approach for conducting such an assay is to contact an antiligand of interest with a test solution potentially containing a ligand that binds to the antiligand. The resulting mixture can then be contacted with any immobilized antibody that specifically binds to the antiligand to immobilize any complexes that have been formed. Labeled antibodies specific for the ligand can then be contacted with any immobilized complexes to detect the presence of such complexes.

A variety of strategies are available for immobilizing complexes. One general approach is to use some type of support that can pass through the flow channels. The support is used to bear the ligand or antiligand during a test. These mobile supports can be immobilized within the cages described supra. The size of the cages is such that the supports are retained within the cage but different solutions can be passed through the limited openings in the cage.

Another immobilization option is to attach a ligand or antiligand (i.e., one member of a binding pair) to the surface of a flow channel. The ligand (antiligand) attached to the flow channel can be attached directly to the flow channel surface or via a linker. In general, the flow channel surface and the ligand (antiligand) being attached to the channel surface need appropriate chemical functionality such that the functional groups borne by these two entities can react with one another and become attached. Often the attachment is achieved by formation of a covalent bond between the binding pair member and surface, although electrostatic, hydrogen bond interactions and hydrophobic interactions can also act to attach the binding pair member and surface.

A variety of linkers can be utilized to attach the ligand (antiligand) to the flow channel wall. A variety of linkers can be utilized. The linkers typically are bifunctional, with a functional group at one end able to react with a functional group on the channel surface and a functional group on the other end able to react with a functional group borne by the ligand (antiligand) to be attached to the flow channel surface. The functional groups at each end of such linkers can be the same or different. Examples of suitable linkers include straight or branched-chain carbon linkers, heterocyclic linkers and peptide linkers. Exemplary linkers that can be employed are available from Pierce Chemical Company in Rockford, Ill. and are described in EPA 188,256; U.S. Pat. Nos. 4,671,958; 4,659,839; 4,414,148; 4,669,784; 4,680,338, 4,569,789 and 4,589,071, Eggenweiler, H. M, Drug Discovery Today 1998, 3, 552.

Other linkers include members of a binding pair. In this arrangement, one binding pair member is attached to the flow channel interior surface. The other member of the binding pair is attached to the ligand (antiligand) one seeks to attach to the channel surface. Exemplary binding pair members include biotin/avidin (or streptavidin) and antigen/antibody.

Depending upon the composition of the flow channel, it sometimes is necessary to derivatize the flow channel inner surface so that the binding pair member can be attached. As described supra in the section on channel coatings, a variety of agents can be coated onto the interior channel surface to introduce functionality. Examples include, but are not limited to, silanizing reagents (e.g., 3-aminopropyltriethoxysilane, N-(2-aminoethyl)-3-aminopropyltrimethoxysilane, dimethylchlorosilane or hexamethyldisilazane) which form self-assembled monolayers on the elastomer surface (which can be used to treat individual flow channels), and photochemical crosslinking reagents to create patterns of reactive groups on the elastomer surface (e.g., aryl azide derivatives or quinone-based derivatives). Elastomer surfaces can also be subjected to oxygen plasma treatment or passively modified by creating multiple layers of agents on the interior surface as described above in the section on channel coatings.

Washing of complexes can also be achieved in a variety of ways. One approach is to trap the complexes within a cage and then flow the wash solution(s) through the cage. Another option is to transfer complexes from a pen to a chamber containing wash solution. After being contacted with the wash solution, the complexes are transported back to the pen and a new wash solution introduced into the chamber. The complexes can then subsequently be returned to the chamber for additional washing. This process can be repeated as many times as necessary.

3. Homogeneous Assays

The binding assays conducted with the microfluidic devices provided herein can also be conducted in homogeneous formats. In the homogeneous formats, ligands and antiligands are contacted with one another in solution and binding complexes detected without having to remove uncomplexed ligands and antiligands.

FP and FRET: Two approaches frequently utilized to conduct homogenous assays are fluorescence polarization (FP) and FRET assays, which are described supra. FP assays can be conducted in a homogenous format because the method is sensitive to tumbling rates of the fluorescently labeled entity. If a labeled ligand is free is solution its tumbling rate is significantly higher than that for a ligand that has become complexed to an antiligand, especially if the antiligand is a macromolecule (see, e.g., Chen et al. (1999) Genome Research 9:492-8; and U.S. Pat. No. 5,593,867 to Walker et al.).

FRET assays can sometimes be performed in a homogenous format because in direct binding assays the donor and acceptor fluorophores borne by the ligands and antiligands initially are generally far enough apart that minimal energy transfer occurs. However, once a ligand/antiligand complex is formed, the donor and acceptor labels are brought sufficiently close to one another such that energy transfer, which transfer can be detected.

Confocal Microscopy: As indicated supra, certain systems utilize a microfluidic device as provided herein utilizing confocal microscopy as a detection method. Such arrangements can be used to conduct binding assays in a homogenous format. Certain of these assays generally involve measuring amounts of bound and free signal utilizing confocal microscopy to distinguish between labeled ligand that is part of a complex and unbound labeled ligand. Confocal microscopy allows this distinction to be made by taking advantage of the fact that with confocal microscopy one can confine detection of an illuminated species to a narrow object plane. Thus, one can essentially view a thin slice of a sample, for example. The same result can be achieved using conventional microscopy (i.e., non-confocal microscopy) by sequentially viewing different depths in the sample, albeit in a less convenient manner.

Hence, in certain assays utilizing the devices described herein test compounds are screened for their ability to inhibit or promote binding between a labeled ligand (e.g., a fluorescently labeled ligand) and a target molecule that is present on the surface of a cell or support. The effect, if any, of the test compound on binding between the labeled ligand and target molecule is monitored by determining the amount of labeled ligand complexed with the cell or support in the presence of the test compound. Unbound ligand appears as a background of relatively constant signal. Ligand that is part of a complex, in contrast, appears as regions of increased fluorescence against such a background. Thus, in assays utilizing fluorescently labeled ligands, for example, the amount of fluorescence associated with individual cells or supports is totaled to obtain a value that is representative of the amount of binding between the labeled ligand and target. This amount is compared to the amount of free fluorescence to obtain a value that is a measure of the inhibitory or enhancing effect of the test compound.

Assays of this type are preferably conducted using laser scanning confocal microscopy. Such microscopes are commercially available from Biometric Imaging Inc. (Mountain View, Calif.), for example. Other confocal microscopes that are suitable in certain applications are described in U.S. Pat. Nos. 5,032,720; 5,120,953; 5,260,578; 5,304,810; 5,283,684; and 5,162,946. The use of confocal microscopy in binding assays is also discussed in U.S. Pat. No. 5,876,946.

Scinitillation Proximity Assays: Other homogenous assays that can be performed with the provided devices utilize supports (e.g., polymeric beads) that are coated or impregnated with scintillant and that beat a ligand that can bind to a radiolabeled target molecule in a sample. Upon binding of the ligand to the target, the radiolabel activates the scintillate such that it emits a detectable signal. The level of the emitted signal is a measure of the amount of ligand complexed with the target in the sample. Assays of this type are described further in U.S. Pat. No. 4,568,649, for example. Beads for conducting such assays are available from Amersham Corp. (Arlington Heights, Ill.).

Europium Cryptate Methods: The microfluidic devices can also be used in binding assays that utilize ligands labeled with an energy-donating label having a long-lived fluorescent state and targets that are labeled with an energy-accepting label that has a short fluorescent excited state. Often such assays are performed using ligands labeled with Europium cryptate (the energy donating label) and a target that is labeled with an energy-accepting protein such as allophycocyanin (the label with the short fluorescent excited state). Energy transfer occurs between these labels once they are brought within close proximity (e.g., less than 7 nm apart) such as occurs upon formation of a complex that contains these two labels. The assay itself involves exciting the Eu-cryptate with a pulsed laser. The fluorescent emission from this label continually re-excites the allophycocyanin. Fluorescence from this protein can be measured utilizing time resolved fluorescent techniques.

4. Assays for Compounds that Inhibit Binding Interactions

The microfluidic devices can also be utilized in a competitive formats to identify agents that inhibit the interaction between known binding partners. Such methods generally involve preparing a reaction mixture containing the binding partners under conditions and for a time sufficient to allow the binding partners to interact and form a complex. In order to test a compound for inhibitory activity, the reaction mixture is prepared in the presence (test reaction mixture) and absence (control reaction mixture) of the test compound. Formation of complexes between binding partners is then detected, typically by detecting a label borne by one or both of the binding partners. The formation of more complexes in the control reaction then in the test reaction mixture at a level that constitutes a statistically significant difference indicates that the test compound interferes with the interaction between the binding partners.

The order of addition of reactants can be varied to obtain different binding information concerning the compounds being tested. For example, test compounds that interfere with the interaction between binding pair members can be identified by conducting the reaction in the presence of the test compound, i.e., by introducing the test compound into the reaction mixture prior to or simultaneously with the binding pair members. Alternatively, test compounds capable of disrupting preformed complexes can be identified by adding the test compound to the reaction mixture after the complexes have been formed. This latter type analysis enables one to identify compounds that have a higher binding constant then one of the members of the binding pair and thus is able to displace that binding pair member from the complex.

5. Immmunological Assays

Immunological assays are one general category of assays that can be performed with the microfluidic devices provided herein. Certain assays are conducted to screen a population of antibodies for those that can specifically bind to a particular antigen of interest. In such assays, a test antibody or population of antibodies is contacted with the antigen. Typically, the antigen is attached to a solid support. The support can be a mobile support such as a bead or the interior wall of a flow channel, for example. If mobile supports are utilized, the supports are typically retained within a holding space during washing and/or detection to facilitate the analysis. If the antigen is attached to a flow channel wall, typically the antigens are attached within the detection region or a holding zone to aid detection. Other assays are conducted to examine a sample to determine if an analyte of interest is present by detecting binding between an antibody that specifically recognizes the analyte and the analyte. In assays such as this, often it is the antibody that is attached to a support (e.g., a mobile support or the wall) and a solution containing potential antigens contacted with the immobilized antibody. In both types of assays, however, either the antigen or antibody can be immobilized. The screens can also be conducted in a homogeneous format in which complexes are formed in solution and detected without further separation. This can be accomplished, for example, by monitoring labeled antigen by fluorescence polarization. Because the tumbling rate of labeled antigen will be considerably faster than the tumbling rate once the antigen is bound by antibody, labeled complexes can be distinguished from labeled antigen.

Immunological assays can be conducted in a variety of different formats. For example, the assays can involve direct binding between antigen and antibody, the so-called sandwich assay, enzyme linked immunosorbent assays (ELISA) and competitive assays. In an ELISA assay, for example, a capture antibody that specifically binds to the analyte of interest is attached to a solid support. As indicated supra, attachment can be to a support or a surface of a flow channel that is located at a position in the flow channel that can be monitored by the detector. A solution potentially containing the analyte of interest is then introduced into a flow channel and contacted with the immobilized capture antibody to form a binary complex. A second antibody (a detection antibody) that recognizes another portion of the analyte than the capture antibody is then contacted with the binary complex to form a ternary complex. The detection antibody includes an assayable enzyme. Thus, formation of the ternary complex can be detected by introducing the appropriate enzyme substrate into the flow channel and allowed to contact any ternary complex. Signal produced in association with the enzyme catalyzed formation of product is detected by the detector.

As discussed supra, capture antibodies can be attached to flow channel interior surfaces via functional groups borne by the antibody (e.g., amino, carboxyl, sulfhydryl, hydroxyl) and complementary groups on the channel surface or introduced by derivatization.

E.4 Enzyme Assays

1. General

Utilizing the microfluidic devices provided herein, a variety of enzymatic assays can be performed. Such enzymatic assays generally involve introducing an assay mixture containing the necessary components to conduct an assay into the various branch flow channels. The assay mixtures typically contain the substrate(s) for the enzyme, necessary cofactors (e.g., metal ions, NADH, NAPDH), and buffer, for example. If a coupled assay is to be performed, the assay solution will also generally contain the enzyme, substrate(s) and cofactors necessary for the enzymatic couple.

Solutions containing the enzyme to be assayed are subsequently mixed with the assay solution. Depending upon the configuration of the microfluidic device, this can be accomplished in a number of different ways. For example, the assay solution can be retained in a holding space and then mixed with enzyme introduced into a branch flow channel. Alternatively, using a device such as that illustrated in FIG. 12 or 19, assay solution can be introduced into a branch flow channel via the main flow channel and a portion retained in the holding space. Different solutions containing enzymes can subsequently be introduced into the different branch flow channels to partially fill the chamber within the branch flow line. The assay solution retained in the holding space can then be transported to the chamber to initiate reactions and the resulting mixture returned to the holding section or to the detection region to monitor enzymatic activity. Assays can also be conducted by first introducing enzyme solutions into the different branch flow channels and then introducing assay solutions into the various branch flow channels. However, it is usually easier to introduce the common reactant, in this case the assay solution, into the main flow channel which allows for the facile diversion of assay solution into each of the branch flow channels, than to separately introduce the common reactant into each branch flow channel.

If a device such as shown in FIGS. 12, 13 or 19 is utilized, common assay reagents can be introduced via the main flow channel(s) and different samples via the branch flow channels.

The mode of detection will vary depending upon the nature of the product generated. Often enzymatic reactions involve monitoring the appearance of a detectable product or the disappearance of a detectable substrate that absorb or emit light at a particular wavelength. In such instances, the detector is able to detect absorption or emission at that wavelength. Fluorescence polarization can also be utilized too conduct enzyme assays. As noted supra, fluorescence polarization involves detecting differences in signals resulting from differential tumbling rates for large and small labeled agents. One strategy is to use a fluorescently labeled substrate that bears a member of a binding pair. The assay solution also includes a macromolecule that bears the other member of the binding pair. In the absence of enzyme, the fluorescently labeled substrate becomes attached to the macromolecule via interaction between the binding pair members. However, if enzyme is present, the substrate, is cleaved, producing a small labeled substrate that produces a significantly different polarization signal then the fluorescent label when attached to the macromolecule (see, e.g., Levine, et al. (1997) Anal. Biochem. 247:83-8).

A variety of screening assays can also be conducted with the microfluidic devices provided herein to identify compounds that modulate.(i.e., activate or inhibit) an enzymatic activity of interest. In general such compounds are generally screened by contacting the enzyme with a substrate in the presence and absence of the compound being screened under conditions conducive to the activity of the enzyme. The resulting reactant mixture is then assayed for the presence of reaction product or a decrease in substrate concentration. In some instances, this amount is compared to a control reaction conducted in parallel with the test reaction. The control reaction can involve contacting the enzyme in the absence of test compound or in the presence of a known inhibitor, for example. In operation, the foregoing methods describing enzyme assays generally apply, except that the assay solution also includes the compound under test. Alternatively, the test compound can also be introduced separately.

Another option is to utilize devices that include the elastomeric mixers described supra. These mixers can be useful for ensuring adequate mixing between assay solution enzyme solution before detection is initiated. Additionally, detection can be continued over time to follow the rate of reaction with time. Such information can be utilized to determine kinetic values.

2. Methods wherein Generated Product is Detected be Optical Means

Heterogeneous Time-Resolved Fluorescence (HTRF). HTRF is one detection scheme that can be used to conduct enzymatic assays. For example, tyrosine kinases can be assayed using HTRF. In such assays, a kinase peptide substrate labeled with a fluorescent acceptor molecule (e.g., XL665 available from Packard Biosciences) is incubated with the kinase and inhibitors. Kinase activity is detected by adding a EuK-labeled anti-phosphotyrosine antibody (available from Packard-Biosciences). Upon binding of the antibody to the phosphotyrosine residue, the acceptor and donor are brought into close contact. Excitation at 337 nm then results in an increase of fluorescence at 665 nm measured 50 µs after excitation, and an increase in the $F_{665}/F_{620}$ ratio.

Such assays can be conducted with the high throughput screening devices disclosed herein. For instance, using the device shown in FIG. 13, common reaction components can be introduced into the main flow channels (i.e., channels A, B and C) in any order, and then mixed with inhibitors. Thus, for example, substrate, inhibitor and antibody can be introduced into the same or different main flow channels. Samples can be introduced into the branch flow channels (i.e., channels 1, 2 and 3). As samples are transported down the branch flow channels, they become mixed with the substrate, inhibitor and antibody located in the chambers. After incubation for a suitable time, the reaction is measured using an HTRF approach with excitation at 337 nm and ratiometric measurement of $F_{665}/F_{620}$. Detection is then performed in the chamber at which all assay components have been added or further downstream in a separate detection section.

Fluorescence resonance energy transfer (FRET). Methods utilizing FRET are another common way to detect enzymatic activity; such methods can be performed with the present microfluidic devices. Certain FRET-based methods utilize fluorescently labeled proteins as part of the detection strategy. For example, FRET can be generated when green fluorescent protein (GFP) and blue fluorescent protein (BFP) are covalently linked together by a short peptide. Cleavage of this linkage by a protease completely eliminates the FRET effect. Such an approach can be used with caspase-3 (CPP32), an important cellular protease activated during programmed cell death, for example. An 18 amino acid peptide containing a CPP32 recognition sequence, DEVD (SEQ ID NO: 1), can be used to link GFP and BFP together. CPP32 activation can be monitored by FRET assay during the apoptosis process (see, e.g., Xu, X., A. L. Gerard, et al. (1998). Nucleic Acids Res 26: 2034-5.

Fluorescence polarization. FP is another useful enzymatic detection method that can be utilized with the devices and assay methods described herein. As indicated supra, FP can be used to study a variety of ligand/antiligand interactions. For example, this approach can be used to study receptor-ligand interactions (surface and nuclear receptors, cytokine & chemokines and their receptors) as well as enzymatic reactions (e.g. serine/threonine and tyrosine kinases and hydrolytic reactions such as proteases and hydrolases). As a specific example, the activity of Protein Kinase C (PKC) family members (phosphorylation of serine and threonine residues) can be assayed with the present microfluidic devices. The activity of Protein Kinase C (PKC) family members is critical to the normal regulation of many biological mechanisms, including the modulation of membrane structure and skeletal reorganization, receptor desensitization, transcriptional control, cell growth and differentiation, and mediation of immune response. PKCs also play a role in memory, learning and long-term potentiation.

An example of a specific PCK assay is a competition assay in which a fluorescent phosphopeptide tracer and the nonfluorescent phosphopeptides generated during a PKC reaction compete for binding to an antiphosphoserine antibody. In a reaction mixture containing no phosphopeptide product, the fluorescent tracer is bound by the antibody and the emission signal is polarized. However, in a reaction mixture containing phosphopeptide product, the fluorescent tracer is displaced from the antibody and the emission signal becomes depolarized. Using a microfluidic device such as depicted in FIGS. 12 and 13, components of the reaction, including the fluorescent and competitive substrates and inhibitors, can be introduced via the main flow channel(s) and mixed rapidly with potential inhibitors introduced into the branch flow channels. Sequestration of reactions in rotary mixers enables aliquots to be withdrawn, quenched, as necessary and moved into a detection region for determination of polarization. Sampling of aliquots allows kinetic measurements to be measured.

3. Capture of Enzyme Product

The devices can be arranged to include a material that selectively binds to an enzymatic product that is produced. In some instances, the material has specific binding affinity for the reaction product itself. Somewhat more complicated systems can be developed for enzymes that catalyze transfer reactions. Certain assays of this type, for example, involve incubating an enzyme that catalyzes the transfer of a detectable moiety from a donor substrate to an acceptor substrate that bears an affinity label to produce a product bearing both the detectable moiety and the affinity label. This product can be captured by material that includes a complementary agent that specifically binds to the affinity label. This material typically is located in a detection region such that captured product can be readily detected. In certain assays, the material is coated to the interior channel walls of the detection section; alternatively, the material can be a support located in the detection region that is coated with the agent.

One specific example of such an approach is one in which the affinity label is a metal chelating agent (e.g., a plurality of histidine residues) and the capture material is a metal-derivatized material. Even more specifically, in certain assays, the detectable moiety that is transferred is radiolabeled such that the reaction product bears the radiolabel and the metal chelating agent. The capture material in this particular assay is also coated or impregnated with scintillant. Thus, once the reaction product becomes bound to the metal-derivatized capture material via the metal chelating agent, the radiolabel causes the scintillant to emit a signal that can be detected. Systems utilizing such an approach are discussed further, for example, in U.S. Pat. No. 6,146,842. One advantage of this particular assay but also other assays of this general type is that they often can be conducted in a homogenous format, thus allowing detection to proceed without the need to remove other reactants.

Using assays of this type, test compounds can also be included in the assay mixtures to determine their ability to enhance or inhibit the transfer activity.

F. Receptor Activation and Second Messenger Assays

1. Ligand-Receptor FCS Assays

Certain assays utilizing the present devices are conducted with vesicles rather than cells. Once example of such an assay is a G-protein coupled receptor assay utilizing fluorescent correlation spectroscopy (FCS). Membrane vesicles constructed from cells that over-express the receptor of interest are introduced into a main flow channel. Vesicles can either be premixed with inhibitor and introduced via branch flow channels or via one of the main flow channels prior to being mixed with a fluorescent natural ligand which is also introduced by a main flow channel. Components are allowed to incubate for the desired time and fluorescent signals analyzed directly in the flow chamber using an FCS reader such as the Evotec/Zeiss Confocor (a single or dual photon counting device).

2. Ligand-Receptor FRET Assays

FRET assays can also be utilized to conduct a number of ligand-receptor interactions using the devices disclosed herein. For example, a FRET peptide reporter can be constructed by introducing a linker sequence (corresponding to an inducible domain of a protein such as a phosphorylation site) into a vector encoding for a fluorescent protein composed of blue- and red- shifted GFP variants. The vector can be a bacterial (for biochemical studies) or a mammalian expression vector (for in vivo studies). For instance, a FRET peptide reporter composed of a region in the cAMP-responsive element binding protein (CREB) designated KID (kinase-inducible domain) can be utilized (see, e.g., Nagai, Y. et al. (2000) Nat. Biotechnol. 18:313-316). The linase-inducible domain contains a phosphorylation site at Ser100 for protein kinase A (PKA). Upon phosphorylation, there is a fluorescence-activated energy transfer (FRET) between donor (Blue GFP) and acceptor (green GFP). cAMP induced, PKA-mediated phosphorylation of KID on SER133 leads to a conformational change that decreases FRET between the donor and acceptor. The ratio between the emissions at 450 nm and 510 nm is increased in response to KID phosphorylation. A control peptide containing the fluorescent protein without the linker sequence can be utilized in control reactions.

For an in vitro assay, the FRET peptide reporter fusion protein is purified from bacteria and a standard biochemical assay (i.e. kinase assay) is performed using the device in FIG. 13 or 19, for example. For an in vivo, assay, a mammalian expression vector that encodes the FRET peptide reporter is transfected into mammalian cells as described in Nagai et al. (Nat. Biotechnol. 18:-313-316-(2000)).

3. Nuclear Receptors

FRET Assays: Assays of nuclear receptors can also be performed with the present microfluidic devices. For example, FRET-based assays for co-activator/nuclear receptor interaction can be performed. As a specific example, such assays can be conducted to detect FRET interactions between: (a) a ligand binding domain of a receptor tagged with CFP (cyan fluorescent protein, a GFP derivative), and (b) a receptor binding protein (a coactivator) tagged with the Yellow fluorescent protein (YFP). Interaction between these components that are abolished by receptor antagonists can be detected by the loss of FRET. Further details of such methods are provided by Llopis et al. (2000) Proc. Natl. Acad. Sci. USA 97:4363-8.

Such cell-based assays can be implemented in the present microfluidic devices such as that shown in FIGS. 12 and 13. Cells transfected with constructs in which the relevant coactivator and nuclear receptor ligand binding domain are tagged with acceptor CFP and donor BFP. Cells are incubated with potential inhibitors and ratiometric measurements at each of the emission maxima of the donor and acceptor are made.

Fluorescence polarization (FP): FP can be utilized to develop high throughput screening (HTS) assays for nuclear receptor-ligand displacement and kinase inhibition. Because FP is a solution-based, homogeneous technique, there is no requirement for immobilization or separation of reaction components. In general, the methods involve using competition between a fluorescently labeled ligand for the receptor and related test compounds. Examples of such assays are discussed by Parker, G. J., T. L. Law, et al. (2000) J Biomol Screen 5:77-88.

G. Cell Reporter Assays

A number of different cell reporter assays can be conducted with the provided microfluidic devices. One common type of reporter assay that can be conducted include those designed to identify agents that can bind to a cellular receptor and trigger the activation of an intracellular signal or signal cascade that activates transcription of a reporter construct. Such assays are useful for identifying compounds that can activate expression of a gene of interest. Two-hybrid assays are another major group of cell reporter assays that can be performed with the devices. The two-hybrid assays are useful for investigating binding interactions between proteins. These are discussed in greater detail in the following sections.

Often cell reporter assays are utilized to screen libraries of compounds. Although a variety of microfluidic devices including the various components disclosed herein can be used, a device such as that shown in FIG. 12 can be utilized in the high throughput screening of a library of compounds for their ability to activate a receptor or influence binding between binding proteins. In general such methods involve introducing the cells into the main flow channel so that cells are retained in the chambers located at the intersection between the main flow channel and branch channels. Different test agents (e.g., from a library) can then be introduced into the different branch channels where they become mixed with the cells in the chambers.

Alternatively, cells can be introduced via the main flow channel and then transferred into the branch channel, where the cells are stored in the holding areas. Meanwhile, different test compounds are introduced into the different branch flow channels, usually to at least partially fill the chambers located at the intersection of the main and branch flow channels. The cells retained in the holding area can be released by opening the appropriate valves and the cells transferred to the chambers for interaction with the different test compounds. Once the cells and test compounds have been mixed, the resulting solution is returned to the holding space or transported to the detection section for detection of reporter expression. The cells and test agents can optionally be further mixed and incubated using mixers of the design set forth above.

1. Receptor Binding and Gene Activation

The cells utilized in screening compounds to identify those able to trigger gene expression typically express a receptor of interest and harbor a heterologous reporter construct. The receptor is one which activates transcription of a gene upon binding of a ligand to the receptor. The reporter construct is usually a vector that includes a transcriptional control element and a reporter gene operably linked thereto. The transcriptional control element is a genetic element that is responsive to an intracellular signal (e.g., a transcription factor) generated upon binding of a ligand to the receptor under investigation. The reporter gene encodes a detectable transcriptional or translational product. Often the reporter (e.g., an enzyme) can generate an optical signal that can be detected by a detector associated with a microfluidic device. General cell reporter systems are discussed in U.S. Pat. No. 5,436,128. In addition to their use in identifying compounds that are ligands of receptors that trigger gene activation, the methods can also be used to identify compounds that are agonists or antagonists of receptors of interest.

A wide variety of receptor types can be screened. The receptors often are cell-surface receptors, but intracellular receptors can also be investigated provided the test compounds being screened are able to enter into the cell. Examples of receptors that can be investigated include, but are not limited to, ion channels (e.g., calcium, sodium, potassium channels), voltage-gated ion channels, ligand-gated ion channels (e.g., acetyl choline receptors, and GABA (gamma-aminobutyric acid) receptors), growth factor receptors, muscarinic receptors, glutamate receptors, adrenergic receptors, dopamine receptors (see, e.g., U.S. Pat. Nos. 5,401,629 and 5,436,128). Additional receptors include the G-protein coupled receptors, specific examples of which include substance K receptor, the angiotensin receptor, the α- and β-adrenergic receptors, the serotonin receptors; and PAF receptor (see, e.g., Gilman (1987) Ann. Rev. Biochem. 56: 625-649).

A number of different reporters can be used to detect gene activation. Certain reporter gene encode proteins that are inherently detectable. One specific example of such a reporter is green fluorescent protein. Fluorescence generated from this protein can be detected with various commercially-available fluorescent detection systems. Other reporters can be detected by staining. Most commonly, however, the reporter is an enzyme that generates a detectable signal when contacted with an appropriate substrate. Often the reporter is an enzyme that catalyzes the formation of a detectable product. Suitable enzymes include, but are not limited to, proteases, nucleases, lipases, phosphatases and hydrolases. Typically, the reporter encodes an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282:864-869); luciferase (lux); β-galactosidase; LacZ; β-glucuronidase; and alkaline phosphatase (Toh, et al. (1980) Eur. J. Biochem. 182:231-238; and Hall et al. (1983) J. Mol. Appl. Gen. 2:101), each of which are incorporated by reference herein in its entirety. Other suitable reporters include those that encode for a particular epitope that can be detected with a labeled antibody that specifically recognizes the epitope.

The cells utilized in the cell based assay can include any of those described supra. In general, the cells must express the receptor of interest. The receptor can be an endogenous receptor or a receptor expressed from a heterologous construct that includes the gene that encodes for the receptor of interest. In the latter instance, the cell must be able to transfected with the construct and able to express the heterologous receptor.

2. Two Hybrid Assays

Another general category of cell assays that can be-performed is the two hybrid assays. In general, the two-hybrid assays exploit the fact that many eukaryotic transcription factors include a distinct DNA-binding domain and a distinct transcriptional activation domain to detect interactions between two different hybrid or fusion proteins. Thus, the cells utilized in two-hybrid assays include the construct(s) that encode for the two fusion proteins. These two domains are fused to separate binding proteins potentially capable of interacting with one another under certain conditions. The cells utilized in conducting two-hybrid assays contain a reporter gene whose expression depends upon either an interaction, or lack of interaction, between the two fusion proteins.

In standard two-hybrid systems, interaction between the two binding proteins results in expression of the reporter gene (see, e.g., Fields, S. and Song, O. (1989) Nature 340:245; Bartel, P. L., and Fields,, S. (1995) Methods in Enzymology 254:241-263; Heery, D. M., et al. (1997) Nature 387:733-736; and Bartel, et al. (1993) Biotechniques 14:920). Reverse hybrid systems, in contrast, are designed such that interaction between the two binding proteins suppresses reporter expression. In these systems, reporter expression is triggered when a compound inhibits the interaction between the two binding proteins (see, e.g., PCT publication WO 95/26400). two-hybrid assays can be utilized to establish interactions between two known proteins or to search a genomic or cDNA library for proteins that interact with a target protein.

H. Monitoring Cell Membrane Potential

A variety of methods to assay for cell membrane potential can be conducted with the microfluidic devices disclosed herein. In general, methods for monitoring membrane potential and ion channel activity can be measured using two alternate methods. One general approach is to use fluorescent ion shelters to measure bulk changes in ion concentrations inside cells (see below). The second general approach is to use of FRET dyes sensitive to membrane potential (see. e.g., U.S. Pat. Nos. 6,124,128 and 5,981,200). Ion channel measurements are typically conducted with whole cells that encode endogenous ion channel components or expressing heterologous constructs that encode ion-channel components. A discussion of such assay is provided by Takahashi, et al. (1999) Physiol. Rev. 79:1089-125; and Gonzalez et al. (1997) Chem. Biol. 4:269-77

As a specific example of such methods that can be utilized with the present devices, certain fluorescence-based assays involve the detection of cell membrane potentials based on the transfer of fluorescence, resonance energy between fluorescently labeled phospholipids. The measurement of changes in membrane potential depends upon the disruption of FRET from coumarin-labeled donor lipids to oxonol acceptors that electrophorese from one face of the membrane to the other in response to membrane potential. For instance, certain assays utilize a coumarin-labeled phosphatidylethanolamine donor and a bis(1,3-dihexyl-2-thiobarbiturate)trimethineoxonol acceptor. This particular combination is highly sensitive (fluorescence ratio change >50% per 100 mV). Response can also be speeded several-fold by lengthening the mobile dye to the pentamethineoxonol analog.

In operation with the present devices, cells are preloaded with FRET dyes and introduced through a common reagent port. Potential inhibitors are loaded through branch flow channels. Cells can be trapped in a pen and flushed with the inhibitors. The ion channel is then stimulated to open by the application of an appropriate stimulus (ligand or ion). FRET measurements are made at appropriate wavelengths.

I. Cell Proliferation Assays

The microfluidic devices disclosed herein can be utilized to conduct a variety of different assays to monitor cell proliferation. Such assays can be utilized in a variety of different studies. For example, as described further infra, the cell proliferation assays can be utilized in toxicological analyses, for example. Cell proliferation assays also have value in screening compounds for the treatment of various cell proliferation disorders including tumors. Compounds identified as having activity as inhibitors of cell proliferation can be utilized to inhibit mitogenesis, inhibit angiogenesis and to activate the complement pathway, including activation of killer cells.

The ability to conduct assays of angiogenesis is of value because angiogenesis refers to the formation of blood and lymph vessels. Angiogenesis plays an important role in a number of different physiological processes including embryonic development, wound healing and the development of the endometrium after menstruation. Abnormal angiogenesis is correlated with a number of diseases including, for example, diabetic retinopathy, rheumatoid arthritis, hemangiomas and the growth of solid tumors. It can also be involved in coronary artery disease and restenosis following angioplasty. Thus, compounds identified as inhibitors can serve as candidates in the treatment of these diseases, as well as various dermatological disorders such as psoriasis that have an angiogenic component.

One approach for rapidly screening for compounds that modulate cell proliferation is to determine acid phosphatase levels, as the activity of this enzyme is indicative of cell proliferation and/or cell survival. Any of a number of established phosphatase assays can be utilized to conduct cell proliferation assays. One example of such assays are fluorogenic enzyme assays that utilize fluorescently labeled substrates that generate a fluorescent signal upon cleavage by a phosphatase. One category of suitable substrates are various benzothiazole substrates which when hydrolyzed by acid phosphatase generate a fluorescent product that can be detected. Such substrates are described, for example, in U.S. Pat. Nos. 5424,440 and 5,972,639.

Hence, certain assay methods of this type involve retaining cells within a cell cage as described supra. A lysing agent is then introduced into the microfluidic device and pumped to the cell cage to lyse the captured cells. The substrates for the phosphatase enzyme such as the fluorescently labeled benzothiazole compounds described above can be introduced together with the lysing agent or separately after the cells have been lysed. Fluorescence can be detected within the cell pen or at another detection section located elsewhere.

J. Toxicology/Cell Death Assays

The microfluidic devices disclosed herein can be utilized to perform a variety of different assays designed to identify toxic conditions, screen agents for potential toxicity, investigate cellular responses to toxic insults and assay for cell death. A variety of different parameters can be monitored to assess toxicity. Examples of such parameters include, but are not limited to, cell proliferation, monitoring activation of cellular pathways for toxicological responses by gene or protein expression analysis, DNA fragmentation; changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis. Specific examples of such assays follow.

1. Cell Proliferation; and Morphological and Permeability Changes

Cell Proliferation: Certain toxicology assays involve monitoring cell proliferation. A variety of different assays can be conducted to assess cell proliferation. One specific method involves irreversibly labeling cell-surface and intracellular proteins with a fluorescent dye specific for such proteins. Daughter cells generated during cell proliferation have only half the amount of irreversibly bound dye as the parent. Thus, cell proliferation is characterized by a diminution of cellular fluorescence intensity. Examples of suitable fluorescent dyes to use in such assays include, but are not limited to, carboxyfluoresceindiacetate succinimidyl ester, SNARF-1 and Marina Blue (available from Molecular Probes, Inc.).

Morphological Changes: Apoptosis in many cell types is correlated with altered morphological appearances. Examples of such alterations include, but are not limited to, plasma membrane blebbing, cell shape change, loss of substrate adhesion properties. Such changes are readily detectable with a light microscope. Cells undergoing apoptosis can also be detected by fragmentation and disintegration of chromosomes. These changes can be detected using light microscopy and/or DNA or chromatin specific dyes.

Altered Membrane Permeability: Often the membranes of cells undergoing apoptosis become increasingly permeable. This change in membrane properties can be readily detected using vital dyes (e.g., propidium iodide and trypan blue). Similarly, dyes can be used to detect the presence of necrotic cells. For example, certain methods utilize a green-fluorescent LIVE/DEAD Cytotoxicity Kit #2, available from Molecular Probes. The dye specifically reacts with cellular amine groups. In necrotic cells, the entire free amine content is available to react with the dye, thus resulting in intense fluorescent staining. In contrast, only the cell-surface amines of viable cells are available to react with the dye. Hence, the fluorescence intensity for viable cells is reduced significantly relative to necrotic cells (see, e.g., Haugland, 1996 Handbook of Fluorescent Probes and Research. Chemicals, 6th ed., Molecular Probes, OR and http://www.probes.com).

In the foregoing assays that require observation by light microscopy, the inverted optical microscope described supra can be utilized to monitor cell morphology, for example. If desired, the cells can be contained within a holding space during detection. Assays requiring addition of dyes can be conducted in a variety of ways. For example, the cells to be assayed can be introduced into branch flow channels and then retained in a holding space. By holding the cells in a cage through which fluids can flow, the necessary dyes can be flowed through the space in which the cells are trapped. Test and control cells can be examined in separate branch flow channels. Of course, cells can be mixed with the necessary dyes in the chamber and mixer units and then transferred to a detection section or holding space for observation.

2. Dysfunction of Mitochondrial Membrane Potential

Mitochondria are the maim energy source in cells of higher organisms. These organelles provide direct and indirect biochemical regulation of diverse cellular processes. These process include the electron transport chain activity, which drives oxidative phosphorylation to produce metabolic energy in the form of adenosine triphosphate (i.e., ATP). Altered or defective mitochondrial activity can result in mitochondrial collapse called the "permeability transition" or mitochondrial permeability transition. Proper mitochondrial functioning requires maintenance of the membrane potential established across the membrane. Dissipation of the membrane potential prevents ATP synthesis and thus halts or restricts the production of a vital biochemical energy source.

Consequently, a variety of assays designed to assess toxicity and cell death involve monitoring the effect of a test agent on mitochondrial membrane potentials or on the mitochondrial permeability transition. One approach is to utilize fluorescent indicators(see, e.g., Haugland, 1996 Handbook of Fluorescent Probes and Research Chemicals, 6th ed., Molecular Probes, OR, pp. 266-274 and 589-594). Various non-fluorescent probes can also be utilized (see, e.g., Kamo et al. (1979) J. Membrane Biol.,49:105). Mitochondrial membrane potentials can also be determined indirectly from mitochondrial membrane permeability (see, e.g., Quinn (1976) The Molecular Biology of Cell Membranes, University Park Press, Baltimore, Md., pp. 200-217). Further guidance on methods for conducting such assays is provided in PCT publication WO 00/19200 to Dykens et al.

In those instances in which fluorescent probes are utilized, the necessary dyes can be contacted with the cells or mitochondrial membrane preparations in a number of different ways utilizing the present microfluidic devices. For example, the dyes can be flowed through a cage in which cells or organelles are retained. Alternatively, cells and dyes can be mixed in one of the chambers or mixers, with detection occurring subsequently within a detection region or within a cage.

3. Caspase Activation

Apoptosis is the term used to refer to the process of programmed cell death and involves the activation of a genetic program when cells are no longer needed or have become seriously damaged. This process occurs in the cells of most higher eukaryotes and is necessary for normal development and the maintenance of homeostasis. It also serves as a defense mechanism, as it provides a means by which the body is able to rid itself of unwanted and potentially dangerous cells including, for example, cells infected with viruses, tumor cells and self-reactive lymphocytes.

Apoptosis involves a cascade of biochemical events and is under the regulation of a number of different genes. One group of genes act as effectors of apoptosis and are referred to as the interleukin-1.beta.converting enzyme (ICE) family of genes. These genes encode a family of cysteine proteases whose activity is increased in apoptosis. Thus, inhibitors of these enzymes can inhibit apoptosis. The ICE family of proteases is generically referred to as caspase enzymes. The "c" in the name reflects the fact that the enzymes are cysteine proteases, while "aspase" refers to the ability of these enzymes to cleave after aspartic acid residues.

Consequently, some assays for apoptosis are based upon the observation that caspases are induced during apoptosis. Induction of these enzymes can be detected by monitoring the cleavage of specifically-recognized substrates for these enzymes. A number of naturally occurring and synthetic protein substrates are known (see, e.g., Ellerby et al. (1997) J. Neurosci. 17:6165; Kluck, et al. (1997) Science 275:1132; Nicholson et al. (1995) Nature 376:37; and Rosen and Casciola-Rosen (1997) J. Cell Biochem., 64:50). Methods for preparing a number of different substrates that can be utilized in these assays are described in U.S. Pat. No. 5,976,822. This patent also describes assays that can be conducted using whole cells that are amendable to certain of the microfluidic devices described herein.

Certain caspase assays utilize FRET methodologies. In particular, a substrate is prepared in which a donor fluorophore and an acceptor fluorophore are separated by an amino acid sequence that includes a cleavage recognition site for the caspase protein of interest. Since different caspase cleave at different sequences, specific substrates can be prepared for the particular caspase(s) of interest. Prior to cleavage, the donor and acceptor fluorophore are sufficiently close, that energy transfer occurs. However, upon cleavage, the two labels are no longer in an energy transfer relationship. The change in donor and/or acceptor fluorescence emissions can be detected as described supra. Further guidance on such an approach is discussed by Mahajan, et al. (1999) Chem. Biol. 6:401-9; and Xu, et al. (1998) Nucl. Acids. Res. 26:2034-5. A specific example of a caspase assay is also provided intra in Example I.

4. Cytochrome c Release

In healthy cells, the inner mitochondrial membrane is impermeable to macromolecules. Thus, one indicator of cell apoptosis is the release or leakage of cytochrome c from the mitochondria. Detection of cytochrome c can be performed using spectroscopic methods because of the inherent absorption properties of the protein. Thus, one detection option with the present devices is to place the cells within a holding space and monitor absorbance at a characteristic absorption wavelength for cytochrome c. Alternatively, the protein can be detected using standard immunological methods (e.g. ELISA assays) with an antibody that specifically binds to cytochrome c (see, e.g., Liu et al. (1996) Cell86:147). Detection in such instances can be accomplished as set forth above in the section on immunological methods in the binding assay section.

5. Assays for Cell Lysis

The microfluidic devices disclosed herein can also be utilized to perform assays to detect cell lysis. Such assays are related to apoptosis assays in that the final stage of cell death is typically lysis of the cell. These assays can be utilized in a variety of studies to examine the effects of agents or particular conditions on cells or in investigating the effect of particular compounds on cell health.

When cells die they typically release a mixture of chemicals, including nucleotides, and a variety of other substances (e.g., proteins and carbohydrates) into their surroundings. Some of the substances released include ADP and ATP, as well as the enzyme adenylate cyclase which catalyzes the conversion of ADP to ATP in the presence of excess ADP. Thus, certain assays involve providing sufficient ADP in the assay medium to drive the equilibrium towards the generation of ATP which can subsequently be detected via a number of different means. One such approach is to utilize a luciferin/luciferase system that is well known to those of ordinary skill in the art in which the enzyme luciferase utilizes ATP and the substrate luciferin to generate a photometrically detectable signal.

Thus, the devices disclosed herein can be utilized to introduce test compounds to cells to determine whether they cause the cells to lyse and thus have potential therapeutic value. For example, using tumor cell lines, one can contact the cells with agents to screen for anti-tumor agents. Alternatively, test compounds can be introduced into the devices and contacted with normal cells to assess the toxicity of such compounds. Thus, assays conducted with the devices can also be utilized to conduct toxicological evaluations. Further details regarding certain cell lysis assays that can be performed with some of the microfluidic devices described herein are set forth in PCT publication WO 00/70082.

K. Antimicrobial Assays

By contacting various microbial cells with different test compounds, one can also utilize the devices provided herein to conduct antimicrobial assays, thereby identifying potential antibacterial compounds. The term "microbe" as used herein refers to any microscopic and/or unicellular fungus, any bacteria or any protozoan. Some antimicrobial assays involve retaining a cell in a cell cage and contacting it with at least one potential antimicrobial compound. The effect of the compound can be detected as any detectable change in the health and/or metabolism of the cell. Examples of such changes, include but are not limited to, alteration in growth, cell proliferation, cell differentiation, gene expression, cell division and the like.

One approach for detecting an effect that a compound has on a cell involves utilizing a cell in which the natural promoter is replaced with a heterologous, regulatable promoter. This promoter also typically is operably linked to a reporter gene (see supra). Replacement of the natural promoter can be accomplished by homologous recombination or insertional mutagenesis, for example. Thus, the level of metabolism after a cell has been contacted with a test compound can be assessed by adding an inducer that activates the inserted promoter to trigger expression of the linked reporter gene. Further discussion of antimicrobial assays that can be conducted with whole cells which are amenable the devices described herein is provided by PCT publication WO 99/14311 and WO 01/07061.

L. Cell-Based Model Systems

The devices described herein are not limited to use in applications in which cells flow through channels. For some applications, certain flow channels are segments thereof are coated with a matrix that promotes cell adhesion and growth on the walls and floor of the channel. Suitable coatings include, but are not limited to, poly-lysine, polyornithine, fibronectin, laminin and collagen. Coating with certain types of cells allows different types of assays to be performed. Thus for example, the human vascular system contains capillaries that have approximately 200 μm internal diameter. A model of this capillary system can be created by promotion of the coating of channels with human vascular epithelial cells (HUVECs). Using elastomeric pump devices such as described supra to create fluid flow through such coated channels (which is impossible with electrically-driven microfluidic devices), this in vitro model provides a system that is analogous to the in vivo system. Such a system enables one to assay for a number of important activities, such as cell adhesion in response to chemotactic activities, receptor-ligand binding assays, cell activation and the like.

M. SNP Analysis

1. General

Relatively minor changes in the genome of an organism, including changes as small as a single nucleotide, can result in substantially different phenotypes. For example, these changes or mutations can be responsible for a variety of different diseases, influence the efficacy of different therapeutic treatments and alter the pathogenicity of a microorganism or change the resistance of a microorganism to therapeutics directed towards it. Often such effects are the result of alteration of a single nucleotide. Such alterations are generally referred to as single nucleotide polymorphisms, or simply SNPs. The site at which an SNP occurs is referred to as a polymorphic site or an allelic site. A number of SNPs have been correlated with various human diseases (see, e.g., Publication WO 93/02216 which provides an extensive list of such SNPs). Because SNPs appear regularly throughout the genome, they also serve as useful genetic markers.

The ability to detect specific nucleotide alterations or mutations in DNA sequences has a number of medical and non-medical utilities. For example, methods capable of identifying nucleotide alterations provide a means for screening and diagnosing many common diseases that are associated with SNPs. Such methods are also valuable in identifying individuals susceptible to disease, those who could benefit from prophylactic measures, and thus obtaining information useful in patient counseling and education. Methods for detecting alterations and mutations have further value in the detection of microorganisms, and making correlations between the DNA in a particular sample and individuals having related DNA. This latter capability can be useful in resolving paternity disputes and in forensic analysis.

2. Methods

Certain of the microfluidic devices provided herein can be utilized to conduct mini-sequencing reactions or primer extension reactions to identify the nucleotide present at a polymorphic site in a target nucleic acid. In general, in these methods a primer complementary to a segment of a target nucleic acid is extended if the reaction is conducted in the presence of a nucleotide that is complementary to the nucleotide at the polymorphic site. Often such methods are single base pair extension (SBPE) reactions. Such method typically involve hybridizing a primer to a complementary target nucleic acid such that the 3' end of the primer is immediately adjacent the polymorphic site, or is a few bases upstream of the polymorphic site. The extension reaction is conducted in the presence of one or more labeled non-extendible nucleotides (e.g., dideoxynucleotides) and a polymerase. Incorporation of a non-extendible nucleotide onto the 3' end of the primer prevents further extension of the primer by the polymerase once the non-extendible nucleotide is incorporated onto the 3' end of the primer.

More specifically, if one of the added non-extendible nucleotides is complementary to the nucleotide at the polymorphic site, then a labeled nucleotide is incorporated onto the 3' end of the primer to generate a labeled extension product. If, however, the non-extendible nucleotide is not complementary to the nucleotide at the polymorphic site, then labeled nucleotide is not incorporated and there is no primer extension. Because the incorporated nucleotide is complementary to the nucleotide at the polymorphic site, extended primers provide an indication of which nucleotide is present at the polymorphic site of target nucleic acids.

As noted supra, primers are chosen to have a sequence that will hybridize to the target nucleic acid such that the 3' end of the primer is adjacent to the polymorphic site of the target. Preferably, the 3' end of the primer is immediately adjacent (but does not span) the polymorphic site (i.e., the 3' end hybridizes to the nucleotide just upstream of the polymorphic site). In some instances, methods can be performed with primers that simply hybridize adjacent to the polymorphic site but the 3' end is several nucleotides upstream of the polymorphic site. This is possible so long as none of the nucleotides on the target nucleic acid located between the 3' end of the primer and the polymorphic site are the same as the nucleotide at the variant site. The extension reaction mixture in such instances must also include nucleotides complementary to those nucleotides positioned between the 3' primer end and the polymorphic site.

Additional details and optional methods for conducing genotyping experiments using primer extension reactions are discussed, for example, in U.S. Pat. Nos. 5,981,176; 5,846,710; 6,004,744; 5,888,819; 5,856,092; 5,710,028; and 6,013,431; and in PCT publication WO 92/16657, each of which is incorporated by reference in its entirety.

With the microfluidic devices disclosed herein, genotyping analyses can be conducted in a variety of different formats. For example, using a high throughput screening device such as shown in FIG. 13, the assay components needed to conduct an assay (e.g., buffer, primer, polymerase, and labeled dideoxynucleotide(s) ddNTPs) are introduced into the main flow channel(s) (e.g., channels A, B and/or C in FIG. 13) and into the chambers located along the main flow channel. Different samples containing target nucleic acid (e.g., samples from different individuals) can be introduced into the branch flow channels (e.g., channels 1, 2 and 3 in FIG. 13) where they become mixed with the assay components. Each of the resulting mixtures can then be transported through their respective branch flow channel and optionally into a mixer or holding area. The mixer or holding area can be positioned adjacent a temperature regulator to optimize the temperature for the extension reaction (if any). Following incubation, incorporation of fluorescent label into the an extended primer can be detected in the detection section; the detection section can include the mixer or holding area or be at some other location along the branch flow channel.

Other methods generally track the method just described, but in this instance, the same sample is investigated in a plurality of branch flow channels. Thus, samples can be introduced into one of the main flow channels (e.g., channel A in FIG. 13). However, in this instance, a different labeled non-extendible nucleotide is introduced into the different branch flow channels that include sample from the same individual. Thus, for example, if a SNP is biallelic, one labeled non-extendible nucleotide complementary to one of the nucleotides potentially at the polymorphic site, is introduced into one branch flow channel (e.g., channel 1 in FIG. 13); a non-extendible nucleotide complementary to the other potential nucleotide at the polymorphic site is introduced into a second branch flow channel (e.g., channel 2 in FIG. 13) that contains sample from the same individual. Of course, if a SNP is tetra allelic or if the nature of the SNP is uncertain, non-extendible nucleotides for all four bases (e.g., ddATP, ddTTP, ddCTP, ddGTP) can be run in separate branch flow channels. Using a microfluidic device of the type illustrated in FIG. 13, different assay components can be individually introduced through the plurality of main flow channels.

In some instances, the microfluidic device will include a separation module such as described supra to separate extension products from unextended primers and other reactants. In one configuration, each branch flow channel includes a section that includes a separation matrix able to separate nucleic acids according to size. If the separation section includes electrodes as described above, then separation can be by gel electrophoresis. Another option is to transfer the reaction mixture to another analytical device such as an HPLC or a nucleic acid analyzer such as the MegaBACE analyzer from Molecular Dynamics.

N. Amplification Reactions

Related to the methods just described, the present devices can also be utilized to amplify and subsequently identify target nucleic acids in multiple samples using amplification techniques that are well established in the art. In general such methods involve contacting a sample potentially containing a target nucleic acid with forward and reverse primers that specifically hybridize to the target nucleic acid. The reaction includes all four dNTPs and polymerase to extend the primer sequences.

The devices disclosed herein such as those shown in FIGS. 12 and 13 can be used to conduct amplification reactions as follows. Common reactants such as primers, dNTPs and polymerase are introduced into the main flow channel(s) (e.g., channel A in FIG. 13). Different samples are introduced into the branch flow channels (e.g., channels 1, 2 and 3 in FIG. 13). As described in the SNP screening section, the devices can include a variety of optional modules to further facilitate analysis. For example, branch flow channels can include mixers to adequately mix the amplification mixtures and a temperature controller to regulate temperature. This is particularly important with the amplification reactions which undergo thermal cycling to allow for disassociation and reannealing of primers to target sequences.

Devices used in such amplification reactions can also include a separation module. Often such separation modules are designed to separate amplicons according to size. Thus, certain modules can include electrodes to allow for electrophoretic separations.

The present devices can be utilized in a wide variety of amplification reactions. Examples of amplification reactions that can be conducted with the device disclosed herein include, but are not limited to, (1) polymerase chain reaction (PCR) (see generally, PCR Technology: Principles and Applications for DNA Amplification (H. A. Erlich, Ed.) Freeman Press, New York, N.Y. (1992); PCR Protocols: A Guide to Methods and Applications (Innis, et al., Eds.) Academic Press, San Diego, Calif. (1990); Mattila et al. (1991) Nucleic Acids Res. 19: 4967; Eckert et al., PCR Methods and Applications 1: 17(1991); PCR (McPherson et al. Ed.), IRL Press, Oxford; and U.S. Pat. Nos. 4,683,202 and 4,683,195, each of these being incorporated by reference in its entirety); (2) ligase chain reaction (LCR) (see, e.g., Wu and Wallace (1989) Genomics 4:560 and Landegren et al.:(1988) Science 241:1077); (3) transcription amplification (see; e.g., Kwoh et al. (1989) Proc. Natl. Acad. Sci. USA 86:1173); (4) self-sustained sequence replication (see, e.g., Guatelli et al. (1990) Proc. Natl. Acad. Sci. USA, 87:1874 (1990); and (5) nucleic acid based sequence amplification (NABSA) (see, e.g., Sooknanan, R. and Malek, L.,(1995) Bio Technology 13: 563-65), each of which are incorporated by reference in their entirety. Further guidance regarding nucleic sample preparation is described in Sambrook, et al., Molecular Cloning: A Laboratory Manual, 2nd Ed., Cold Spring Harbor Laboratory Press, (1989), which is incorporated herein by reference in its entirety.

The following examples are provided to further illustrate certain aspects of the invention, but are not to be construed so as to limit the scope of the invention.

EXAMPLE 1

Caspase Activity

I. Background

Caspase-3 (also known as CPP32, apopain and Yama), a member of the interleukin-1β converting enzyme, is one of the cysteine proteases most frequently activated during the process of programmed cell death (apoptosis) Caspase-3 is essential for normal brain development, and has been suggested to contribute to the molecular pathogenesis of several neurological diseases. Thus, development of caspase inhibitors can be used as potential therapeutic approaches for chronic neurodegenerative disorders. However, the assay model is not limited to this protein.

II. Experimental Design

Using the PC12 pheochromocytoma cell line, a well-characterized model of neuronal apoptotic cell death (see, e.g., Rukenstein et al. (1991) J. Neurosci. 11:2552-2563; and Batistatou and Greene (1991) J. Cell Biol. 115:461-71), inhibitors of caspase-3 activity can be screened. Many other cell lines known in the art can be used as well.

Screens are conducted, for example, using the device illustrated in FIG. 13 according to the following steps. In should be recognized, however, a wide variety of other devices can be utilized as well.

1. PC 12 cells are introduced through main flow channel A and into the chambers. Potential inhibitors are introduced into the branch flow channels 1, 2 and 3 and incubated with the cells in the chambers for 10 minutes at 5% $CO_2$ and 37° C. to allow for inhibitor/enzyme interaction.

2. Fluorogenic substrate (PhiPhiLux™, available from CalBiochem) and stimulant (C2-Ceramide, available from Biomol Research Laboratories, hc.) are added to channels B and C, respectively. PhiPhiLux™ is a peptide substrate for caspase-3 that has been conjugated to two fluorophores. The substrate contains the sequence GDEVDGI (SEQ ID NO:2) (caspase cleavage site is underlined). The cleaved PhiPhiLux™ substrate has a green fluorescence with the following fluorescence peak characteristics: $\lambda_{ex}$ =505 nm and $\lambda_{em}$ =530 nm. When the folded peptide is cleaved, the fluorophores provide a high intensity fluorescent signal at a visible wavelength.

3. After 10 minutes, the cells are pumped into the chambers Positioned along main flow channel B and mixed with the cell permeable Caspase-3 fluorogenic substrate PhiPhiLux™ at a concentration of 10 μM and incubated for 20 minutes.

4. After 20 minutes, the cells are Pumped further down their respective flow channels to main flow channel C and mixed with an apoptotic agent such as C2-Ceramide, a cell permeable ceramide analog.

5. Caspase activity is assessed at several time points (e.g., 30 sec, 1 min, 5 min, etc.). After time t, fluorescent signals are detected using an air-cooled argon laser with excitation at 488 nm and detection at 515 nm.

Assays such as this can be used to screen libraries of compounds for inhibitors or agonists of various enzymes. One can also use such a model for multiparametric analysis of signaling elements downstream of the target.

EXAMPLE 2

Screening NGF Agonists in PC12 Cells

I. Background

Screens to identify agonists of receptors of interest can be performed using the present devices. This example describes a method to screen for agonists of nerve growth factor receptor in PC12 cells (described supra). Docking of TrkA with the NGF receptor initiates receptor dimerization, catalytic phosphorylation of cytoplasmic residues on the receptor, and a cascade of signaling events (see, e.g., Kaplan and Stephens (1994) J. Neurobio. 25:1404-1417). Upon TrkA activation, the PI-3K/Akt pathway is activated which results in phosphorylation of Akt (see, e.g., Andjelkovic M. et al (1998) Eur. J. Biochem. 25:195-200). Simultaneously, the MAP kinase pathway is activated which results in phosphorylation of Erk (Kaplan and Stephens, 1994).

II. Experimental Design

Although screens can be conducted with variety of different devices, the following method is described with reference to the microfluidic device depicted in FIG. 13.

1. Cells expressing FRET reporters for TrkA, Erk and Akt are added via main flow channel A. Thus, the cells express a TrkA receptor that upon activation will generate a FRET a signal different from that of the Erk and Akt FRET reporters.

2. Potential agonists are added via branch channels 1, 2, 3, etc.

3. After addition of the potential agonist:
   a. Receptor activation is assessed at various time intervals (30 sec, 1 min, 5 min, etc.). A hit is a compound that acts like NGF and stimulates the NGF receptor and the downstream signaling elements (kinetics of the reaction should be the similar).
   b. If the receptor is activated (phosphorylated), the kinetics of receptor activation will be monitored (tyrosine phosphorylation of the Trk receptor) via fluorescence. The cells express proteins that FRET upon phosphorylation. Each protein (TrkA, Erk and Akt) produces a FRET a specific signal different from one another.
   c. Simultaneously, activation of the downstream signaling elements are assessed and monitored. Activation of the downstream elements (Akt, Erk) can be monitored via fluorogenic substrates or FRET peptide reporters. Thus, for each hit, a profile of activated elements (Trk receptor, Erk, Akt) can be obtained, the profile including the duration and amplitude of the signal.

4. After the cell is restored to its "normal" state, an inhibitor can be added to demonstrate specificity. For example, the TrkA inhibitor K252a or AG879 (available from Biomol Research Laboratories, Inc.) can be used to demonstrate that the agonist is working via the TrkA receptor. If the agonist is specifically targeted to the TrkA receptor, it should not work in the presence of a TrkA inhibitor.

EXAMPLE 3

Screening for G-Protein Coupled Receptor (GPCR) Agonists

I. Background

The calcium ion is a very important messenger in cells. The concentration of free $Ca^{2+}$ is extremely low ($10^{-7}$ M) in the cytpsol compared to the extracellular fluid ($10^{-3}$ M) or to the endoplasmic reticulum. A variety of reactions such as receptor-ligand interactions mediate changes in the concentration of free intracellular calcium ($[Ca^{2+}]i$). The change in intracellular calcium occurs rapidly.

II. Experimental Design

The Fluo-3AM (Molecular Probes Cat. No.1241) absorption spectrum is compatible with excitation at 488 nm by argon-ion laser sources. Upon $Ca^{2+}$ binding, there is a large increase in fluorescence intensity. Fluo-3 AM is cell permeant. A variety of cell types can be utilized including, CHO-K1, HEK-293 and COS.

Assays are conducted as follows:

1. Cells (introduced via inlet A.a), and 2 µM Fluo-3 calcium indicator (introduced via inlet A.b) are added to main flow channel A; such that there is one cell per "chamber".

2. Incubate cells and fluo-3 for 30 minutes in main flow channel A. Conditions for incubations are 5% $CO_2$ and 37° C.

3. After 30 minutes, the cells are pumped to main flow channel B and washed with an indicator-free medium in chambers along channel B to remove any dye that is non-specifically associated with the surface, and then incubated for an additional 30 minutes.

4. After 30 minutes, potential agonists are added via branch flow channels 1, 2, 3, to the cells in main flow channel B.

5. Calcium mobilization is assessed at several time points (e.g., 1 sec, 5 sec, and 30 sec, etc.). After-time t, fluorescent signals are detected using an air-cooled argon laser with excitation at 488 nm and detection at 526 nm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

What is claimed is:

1. A method of treating a cell, comprising:
   (a) providing a microfluidic device comprising:
   (i) a flow channel comprising a detection region;
   (ii) a plurality of control channels; and
   (iii) a pair of storage valves operatively disposed with respect to the flow channel, wherein each storage valve comprises one of the control channels, which control channel is separated from the flow channel by an elastomeric membrane, the elastomeric membrane being deflectable into the flow channel in response to an actuation force applied to the control channel, the two control channels of the storage valves being disposed relative to one another such that deflection of the elastomeric membrane of the respective control channels into the flow channel forms a holding space within the flow channel;
   (b) introducing a sample containing one or more cells into the flow channel;
   (c) actuating the storage valves to hold at least one of the cells within the holding space; and
   (d) contacting the cell or cells within the holding space with a solution containing one or more agents.

2. The method of claim 1, wherein the elastomeric membranes of the storage valves each comprise one or more protrusions, the protrusions adapted to allow for solution to flow through the holding space once the elastomeric membranes are deflected into the flow channel while retaining the cell(s) within the holding space.

3. The method of claim 1, wherein the flow channel is formed within an elastomeric material and a segment of the flow channel opposite the elastomeric membrane of the storage valves comprises one or more elastomeric protrusions, the protrusions adapted to allow for solution to flow through the holding space once the elastomeric membranes are deflected into the flow channel while retaining the cell(s) within the holding space.

4. The method of claim 1, wherein the flow channel is formed within an elastomeric material; the elastomeric segments of the storage valves comprise one or more protrusions; a segment of the flow channel opposite the elastomeric membrane of each storage valve comprises one or more protrusions, and wherein the protrusions of the elastomeric membrane and the protrusions of the branch flow channel are adapted to allow for solution to flow through the holding space once the elastomeric membranes are deflected into the branch flow channel while retaining the cell(s) within the holding space.

5. The method of claim 1, wherein the microfluidic device further comprises a chamber adapted for storing solution in fluid communication with the flow channel and the method further comprises transporting solution and/or cells back and forth between the chamber and the holding space.

6. The method of claim 1, wherein the flow channel is in communication with a pump, and wherein the sample is transported through the flow channel under the action of the pump.

7. The method of claim 6, wherein the pump comprises at least three of the control channels, each formed within an elastomeric material and separated from the flow channel by an elastomeric membrane, each membrane being deflectable into the flow channel in response to an actuation force, whereby sample is transported along the flow channel.

8. The method of claim 1, wherein the flow channel comprises a cell enrichment section that selectively retains cells of interest, and the method further comprises transporting the sample through the enrichment section.

9. The method of claim 8, wherein the enrichment section contains a ligand that specifically binds to a receptor on target cells.

10. The method of claim 1, further comprising detecting an event and/or agent within the detection region with a detector.

11. The method of claim 10, wherein the detection region includes the holding space.

12. The method of claim 10, wherein the detection region is located at a section of the flow channel other than the holding space.

13. The method of claim 10, wherein the detector detects an optical signal within the detection region.

14. The method of claim 13, wherein the detector detects a fluorescence emission, fluorescence polarization or fluorescence resonance energy transfer.

15. The method of claim 13, wherein the detector is an optical microscope, a confocal microscope or a laser scanning confocal microscope.

16. The method of claim 10, wherein the detector is a non-optical sensor selected from the group consisting of a temperature sensor, a conductivity sensor, a potentiometric sensor and an amperometric sensor.

17. The method of claim 1, wherein the assay step comprises flowing a solution through the holding spaces after the storage valves have been actuated.

18. The method of claim 17 wherein the solution flowed through the holding spaces is culture medium for the cells within the holding space.

19. The method of claim 17, wherein the solution comprises a cellular stain.

20. The method of claim 1, further comprising detecting cellular morphology.

21. The method of claim 1, further comprising conducting a cell reporter assay.

22. The method of claim 1, further comprising detecting binding between a ligand and a cell receptor.

23. The method of claim 1, further comprising measuring cell membrane potential.

24. The method of claim 1, further comprising detecting a toxic effect on cells.

25. The method of claim 24, wherein the effect is cell proliferation, dysfunction of mitochondrial membrane potential, caspase activation, or cytochrome c release from cells.

26. The method of claim 1, wherein the treatment is cell lysis.

27. The method of claim 1, further comprising conducting an antimicrobial assay.

28. A method of treating a cell, comprising:
 (a) providing a microfluidic device comprising:
  (i) a main flow channel;
  (ii) a plurality of branch flow channels, each branch flow channel being in fluid communication with the main flow channel;
  (iii) a plurality of control channels; and
  (iv) a plurality of storage valves, wherein a pair of storage valves are operatively disposed with respect to each of the branch flow channels, and wherein, each of the storage valves comprises an elastomeric segment that separates one of the branch flow channels and one of the control channels and that is deflectable, into or retractable from the flow channel upon which the valve operates in response to an actuation force applied to the control channel, the storage valves of a pair being disposed with respect to one another such that when the elastomeric segment of each storage valve of the pair extends into the branch flow channel a holding space is formed between the segments in which one or more cells can be retained;
 (b) introducing a solution containing one or more cells into each of the branch flow channels;
 (c) actuating the storage valves within each of the branch flow channels to form the holding space to hold at least one of the cells, within the sample introduced into the branch flow channel; and
 (d) contacting the cell or cells within the holding space with a solution containing one or more assay agents.

29. The method of claim 28, wherein different cells are introduced into different branch flow channels and the contacting step comprises contacting the cells within each branch flow-channel with the same solution.

30. The method of claim 28, wherein cells of the same type are introduced into each of the flow channels and the contacting step comprises contacting the cells within different branch flow channels with different assay solutions.

31. A method for conducting an assay, comprising:
 (a) providing a microfluidic device comprising:
  (i) a main flow channel;
  (ii) a plurality of branch flow channels, each in fluid communication with the main flow channel and comprising a detection region;
  (iii) a plurality of control channels; and
  (iv) a plurality of valves operatively disposed with respect to the main flow channel and/or the plurality of branch flow channels to regulate flow of the first and second solutions therethrough, wherein each of the valves comprises one of the control channels and an elastomeric segment that is deflectable into or retractable from the main or branch flow channel upon which the valve operates in response to an actuation force applied to the control channel, the elastomeric segment when positioned in the flow channel restricting solution flow therethrough;
 (b) introducing a first assay solution into the main flow channel and a second assay solution into each of the plurality of branch flow channels;
 (c) actuating one or more of the valves to control flow of the first and second assay solutions through the main and branch flow channels, whereby the first and second assay solutions are brought into contact with one another to form an assay solution mixture; and
 (d) monitoring each of the assay solution mixtures for a desired property within the detection region.

32. The method of claim 31, wherein the control channel of each valve is separated from the flow channel in which the valve operates by the elastomeric segment.

33. The method of claim 32, wherein:
 the method is a method for screening a plurality of target agents for the desired property;
 the first assay solution is a solution comprising one or more assay agents and the second assay solution is a solution composing one of the test compounds;
 the introducing step comprises introducing a different test compound into each of the plurality of branch flow channels; and
 the monitoring step comprises identifying at least one test compound having the desired activity.

34. The method of claim 32, wherein the microfluidic device further comprises a first inlet in fluid communication with the main flow channel and a second inlet for each branch flow channel, and wherein the first assay solution is introduced via the first inlet and the second assay solution introduced via the second inlet.

35. The method of claim 32, wherein the microfluidic device further comprises a plurality of pumps, each pump being operatively disposed with respect to one of the branch flow channels, and wherein the method further comprises actuating the pump of each branch channel to transport the first and/or second assay solution through the branch flow channel.

36. The method of claim 35, wherein each of the plurality of pumps comprises a at least three control channels each formed within an elastomeric material and separated from one of the branch flow channels by a section of an elastomeric membrane, the membrane being deflectable into the branch flow channel from which it is separated in response to an actuation force.

37. The method of claim 33, wherein the microfluidic device further comprises a plurality of mixers, each mixer being operatively disposed with respect to one of the branch flow channels, and wherein the method further comprises mixing the first assay solution and the second assay solution with the mixer to form the assay solution mixture prior to the assaying step.

38. The method of claim 37, wherein the mixer comprises
   (i) an inlet section and an outlet section
   (ii) a looped flow channel in fluid communication with the inlet and outlet section; and
   (iii) two sets of control channels, each set comprising at least three control channels, and each control channel separated from the looped flow channel by an elastomeric membrane that is deflectable into the looped flow channel in response to an actuation force, and wherein the mixing step comprises transporting the first and second assay solution into the mixer via the inlet section and mixing the first and second solution in the looped flow channel by applying the actuation force to the control channels within a set as part of a repeating sequence.

39. The method of claim 33, wherein the microfluidic device further comprises a plurality of temperature controllers, each temperature controller being operatively disposed with respect to one of the branch channels, and the method further comprises actuating the temperature controller to regulate the temperature of the first assay solution, the second assay solution and/or the assay solution mixture.

40. The method of claim 39, wherein the temperature controller is disposed to regulate the temperature of the assay solution mixture within the detection region.

41. The method of claim 39, wherein the microfluidic device further comprises a plurality of mixers, each mixer being operatively disposed with respect to one of the branch flow channels, and wherein the method further comprises mixing the first assay solution and the second assay solution with the mixer to form the assay solution mixture prior to the assaying step and wherein the temperature controller is disposed to regulate the temperature of the assay solution mixture within the mixer.

42. The method of claim 33, wherein the microfluidic device further comprises a plurality of separation units, each separation unit being positioned within one of the branch flow channels, and wherein the method further comprises
   (e) transporting a mixture of the first and second assay solutions through the separation unit whereby one or more unwanted compounds are removed to form the assay solution mixture; and
   (f) transporting the assay solution mixture to the detection region.

43. The method of claim 33, wherein the microfluidic device further comprises a plurality of mixers and a plurality of separation units, each mixer being operatively disposed with respect to one of the branch flow channels, and each separation unit being positioned within one of the branch flow channels, and wherein the method further comprises (e) mixing the first assay solution and the second assay solution with the mixer; (f) transporting the mixture of the first and second assay solutions through the separation unit whereby one or more unwanted compounds are removed to form the assay solution mixture; and (g) transporting the assay solution mixture to the detection region.

44. The method of claim 43, wherein each separation unit comprises a semi-permeable membrane that separates one of the branch flow channels and a collection channel, the membrane allowing passage of certain agents in the first or second assay solution or a mixture thereof flowing through the branch flow channel to pass through the membrane and into the collection flow channel.

45. The method of claim 43, wherein the separation unit comprises a separation material that separates molecules on the basis of affinity, size, charge or mobility.

46. The method of claim 33, wherein the microfluidic device further comprises a detector operatively disposed with respect to at least one of the detection regions, and the monitoring step comprises detecting an event or agent within the detection region.

47. The method of claim 46, wherein the detection step comprises detecting an optical signal.

48. The method of claim 47, wherein the detector detects a fluorescence emission, fluorescence polarization or fluorescence resonance energy transfer.

49. The method of claim 48, wherein the detector performs time-resolved fluorescence measurements.

50. The method of claim 48, wherein the detector performs fluorescence correlation spectroscopy.

51. The method of claim 47, wherein the detector is an optical microscope, a confocal microscope or a laser scanning confocal microscope.

52. The method of claim 46, wherein the detector is a non-optical sensor selected from the group consisting of a temperature sensor, a conductivity sensor, a potentiometric sensor and an amperometric sensor.

53. The method of claim 33, wherein the desired property is the ability of the at least one test agent to promote or inhibit binding between a ligand and an antiligand.

54. The method of claim 53 wherein the antiligand is a protein receptor and the ligand is the receptor's cognate ligand.

55. The method of claim 53, wherein the ligand is an antigen and the antiligand is an antibody that specifically binds to the antigen.

56. The method of claim 53, wherein the antiligand is an enzyme and the ligand is an enzyme substrate or inhibitor of the enzyme.

57. The method of claim 53, wherein the ligand is a nucleic acid and the antiligand is a nucleic acid binding protein.

58. The method of claim 33, wherein the desired property is the ability of the at least one test agent to trigger a signal transduction pathway.

59. The method of claim 33, wherein the desired property is the ability of the at least one test agent to inhibit microbial growth.

60. The method of claim 33, wherein the desired property is the ability of the at least one test agent to trigger cell death.

61. The method of claim 33, wherein the desired property is the ability of the at least one test agent to trigger apoptosis in a cell.

62. The method of claim 55, where the monitoring comprises monitoring inhibition of cell proliferation, monitoring mitochondrial membrane function, monitoring caspase activation, or monitoring cytochrome c release from a cell.

63. The method of claim 33, wherein the monitoring step is in a homogenous format.

64. The method of claim 33, wherein the monitoring step is in a heterogenous format.

* * * * *

UNITED STATES PATENT AND TRADEMARK OFFICE
CERTIFICATE OF CORRECTION

PATENT NO. : 7,378,280 B2
APPLICATION NO. : 10/416418
DATED : May 27, 2008
INVENTOR(S) : Stephen R. Quake et al.

It is certified that error appears in the above-identified patent and that said Letters Patent is hereby corrected as shown below:

Column 1, lines 19-23, delete "The U.S. Government has a paid-up license in this invention and the right in limited circumstances to require the patent owner to license others on reasonable terms as provided for by the terms of Grant No. HG-01642-02, awarded by the National Institutes of Health." and insert --This invention was made with government support under Grant No. HG-01642-02 awarded by the National Institute of Health. The government has certain rights in the invention.--

Signed and Sealed this

Twenty-first Day of April, 2009

JOHN DOLL
*Acting Director of the United States Patent and Trademark Office*

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:caspase-3
                        (CPP32) recognition sequence

<400> SEQUENCE: 1

Asp Glu Val Asp
  1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:sequence
                        contained in peptide substrate with caspase
                        cleavage site

<400> SEQUENCE: 2

Gly Asp Glu Val Asp Gly Ile
  1               5
```